United States Patent
Wu et al.

(10) Patent No.: US 10,836,761 B2
(45) Date of Patent: Nov. 17, 2020

(54) CINCHONINE-DERIVED CATALYSTS AND METHODS OF USING SAME

(71) Applicant: BRANDEIS UNIVERSITY, Waltham, MA (US)

(72) Inventors: Yongwei Wu, Waltham, MA (US); Li Deng, Waltham, MA (US)

(73) Assignee: Brandeis University, Waltham, MA (US)

( * ) Notice: Subject to any disclaimer, the term of this patent is extended or adjusted under 35 U.S.C. 154(b) by 65 days.

(21) Appl. No.: 16/063,078

(22) PCT Filed: Dec. 16, 2015

(86) PCT No.: PCT/US2015/066121
§ 371 (c)(1),
(2) Date: Jun. 15, 2018

(87) PCT Pub. No.: WO2017/105439
PCT Pub. Date: Jun. 22, 2017

(65) Prior Publication Data
US 2020/0048243 A1  Feb. 13, 2020

(51) Int. Cl.
*C07D 453/04* (2006.01)
*C07F 7/18* (2006.01)

(52) U.S. Cl.
CPC .......... *C07D 453/04* (2013.01); *C07F 7/1804* (2013.01)

(58) Field of Classification Search
CPC ..................... C07D 453/04; C07D 401/14
USPC .................. 546/135, 134; 544/319
See application file for complete search history.

(56) References Cited

U.S. PATENT DOCUMENTS 5,554,753 A   9/1996 O'Donnell et al.

FOREIGN PATENT DOCUMENTS

WO   2013050301 A1   4/2013

OTHER PUBLICATIONS

Wu, Y. et al.: Catalytic asymmetric umpolung reactions of imines. Nature, vol. 523, pp. 445-450, 2015.*
Shioiri, T. et al.: Imp[ortance of the hydroxymethyl-quinuclidine fragment in the catalytic asymmetric aldol reactions utilizing quaternary ammonium fluorides derived from cinchona alkaloids. Heterocycles, vol. 42, pp. 93-97, 1996.*
Provencher, B. et al.: Structural study-guided development of versatile phase-transfer catalysts for asymmetric conjugate additions of cyanide. Angewandte Chemie, intern. Ed., vol. 50, pp. 10565-10569, 2011.*
Baiker, et al., "Crucial aspects in the design of chirally modified noble metal catalysts for asymmetric hydrogenation of activated ketones," Chem. Soc. Rev., vol. 44, pp. 7449-7464 (2015).
Ooi et al., "Recent Advances in Asymmetric Phase-Transfer Catalysis," Angew Chem. Int. Ed., vol. 46, pp. 4222-4266 (2007).
PubChem—CID-20728932, Create Date: Dec. 5, 2007: p. 3, Fig.
International Search Report and Written Opinion in corresponding PCT/US15/66121, dated May 3, 2016, (9 pages).

* cited by examiner

Primary Examiner — Charanjit Aulakh
(74) Attorney, Agent, or Firm — Danielson Legal LLC

(57) ABSTRACT

The present invention includes certain conchinine-derived phase-transfer catalysts of formula (I), compositions comprising the same, and methods of promoting asymmetric addition reactions using the same.

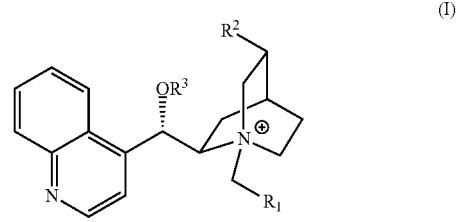

(I)

21 Claims, 13 Drawing Sheets

C-13

C-14 to 21b

PYR:

| Entry | T (°C) | Catalyst | Conversion (%) | 9/4; 9/10 | d.r. of 9 | e.e. of 9 (%) |
|---|---|---|---|---|---|---|
| 1 | RT | C-13 | 41 | 2/98; ND | ND | ND |
| 2 | RT | C-14 | 18 | 11/89; ND | ND | ND |
| 3 | -20 | C-14 | 58 | 37/63; >95/5 | 82/18 | 39 |
| 4 | -20 | C-15 | 54 | 36/64; >95/5 | 67/33 | 18 |
| 5 | -20 | C-16 | 84 | 34/66; >95/5 | 76/24 | 40 |
| 6* | -20 | C-16 | 41 | 32/68; >95/5 | 74/26 | 39 |
| 7* | -20 | C-17 | 14 | 67/33; >95/5 | 87/13 | 68 |
| 8* | -20 | C-18 | 40 | 74/26; >95/5 | 86/14 | 77 |
| 9* | -20 | C-19 | 39 | 45/55; >95/5 | 96/4 | 55 |
| 10* | -20 | C-20 | 66 | 68/32; >95/5 | 91/9 | 85 |
| 11* | -20 | C-21a | 88 | 94/6; >95/5 | 91/9 | 91 |
| 12* | -20 | C-21b | 99 | 99/1; >95/5 | 93/7 | 96 |
| 13* | -20 | C-21b | 97 | 99/1; >95/5 | 93/7 | 95 |
| 14* | -20 | TBAB | 31 | 4/96; ND | ND | ND |

FIG. 4B

Scope of β-substituted enals in reactions with imine 1A

| Entry | R² | Time (h); conversion (%) | 9/4; 9/10 | d.r. of 9 | Yield (%)* | e.e. (%)† |
|---|---|---|---|---|---|---|
| 7 | CH₃CH₂; 8b | 5; 99 | 89/11; >95/5 | >95/5 | 64 (22Ab) | 95 |
| 8 | CH₃(CH₂)₅; 8c | 12; 93 | 86/14; >95/5 | >95/5 | 51 (22Ac) | 96 |
| 9 | Ph; 8d | 8; 93 | >95/5; 68/32 | >95/5 | 51 (22Ad) | 91 |

Scope of imines in reactions with acrolein (8e, R² = H)

| Entry | R¹ | Time (h); conversion (%) | 9/4; 9/10 | Yield (%)* | e.e. (%)† |
|---|---|---|---|---|---|
| 10‡ | H₃C–⌇ 1A | 3; 95 | >95/5; >95/5 | 89 (22Ae) | 92 |
| 11‡ | ⌇ 1B | 3; 99 | >95/5; >95/5 | 82 (22Be) | 91 |
| 12‡ | Br⁀⁀⌇ 1D | 3; 97 | >95/5; >95/5 | 84 (22De) | 91 |
| 13‡ | Cy⁀⌇ 1F | 3; 99 | >95/5; >95/5 | 90 (22Fe) | 92 |
| 14 | Ph; 1G | 3; 99 | 94/6; >95/5 | 71 (23Ge) | 94 |
| 15 | p-MeOC₆H₄; 1H | 3; 94 | 92/8; >95/5 | 67 (23He) | 94 |
| 16 | p-CF₃C₆H₄; 1I | 3; 99 | 88/12; >95/5 | 78 (23Ie) | 92 |
| 17 | Ph⌇ 1J | 1; 99 | >95/5; >95/5 | 90 (23Je) | 93 |

CINCHONINE-DERIVED CATALYSTS AND METHODS OF USING SAME

STATEMENT OF RIGHTS TO INVENTIONS MADE UNDER FEDERALLY SPONSORED RESEARCH

This invention was made with government support under grant No. NIH GM-61591 awarded by the National Institutes of Health. The government has certain rights in the invention.

CROSS-REFERENCE TO RELATED APPLICATIONS

This application is the U.S. national phase application, pursuant to 35 U.S.C. § 371, of PCT international application Ser. No.: PCT/US2015/066121, filed Dec. 16, 2015, designating the United States and published in English.

BACKGROUND OF THE INVENTION

Umpolung, or polarity inversion, in organic chemistry refers to the chemical modification of a functional group with the aim of the reversal of polarity of that group. This modification allows secondary reactions of this functional group that would otherwise not be possible under its standard polarity, and thus allows for the development of new reactions of distinct bond connections.

A classic example of the umpolung reaction is the cyanide-catalyzed condensation of two aromatic aldehydes to provide a benzoin derivative. The successful development of numerous C—C bond-forming umpolung reactions with carbonyls as acyl anion equivalents has greatly expanded the repertoire of organic synthesis. The power of carbonyl umpolung reactions has been tapped for asymmetric synthesis through the successful development of efficient chiral catalysts for enantioselective Stetter reactions (which are 1,4-additions of an aldehyde to an α,β-unsaturated compound, catalyzed by cyanide or a thiazolium salt) and other asymmetric reactions. In contrast, C—C bond-forming umpolung reactions of imines are rarely reported.

There is a need in the art to identify novel catalysts that can be used to promote asymmetric umpolung reactions. The present invention meets this need.

SUMMARY OF THE INVENTION

As described below, the present invention generally provides phase-transfer catalysts that can be used to promote carbon-carbon formation using 2-azaallyl anions in a highly chemoselective, regioselective and enantioselective manner. In certain embodiments, the catalysts of the present invention allow for the asymmetric preparation of chiral amines.

In one aspect, the invention provides certain compounds that may be used as phase-transfer catalysts.

In certain embodiments, the invention provides a compound, or a salt, N-oxide, tautomer, enantiomer or diastereoisomer thereof, of formula (I):

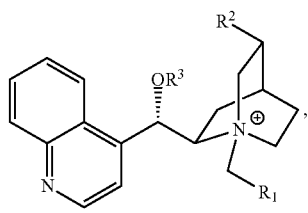

(I)

wherein:
$R^1$ is

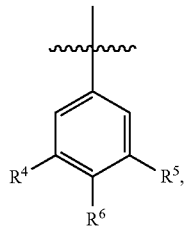

$R^4$ and $R^5$ are independently selected from the group consisting of H, alkyl, alkoxy and aryl, where each occurrence of aryl in $R^4$ or $R^5$ is independently optionally substituted with at least one substituent selected from alkyl, alkoxy, aryloxy, —S-alkyl, —S(aryl), —OSiR$_3$ and —NR$_2$;

$R^6$ is selected from the group consisting of H, alkyl, alkoxy, aryloxy, —S(alkyl), —S(aryl), —OSiR$_3$ and —NR$_2$, and each occurrence of R is independently selected from alkyl and aryl;

$R^2$ is selected from the group consisting of optionally substituted alkyl, optionally substituted alkenyl and optionally substituted alkynyl, where each optional substituent is independently selected from the group consisting of alkyl, alkoxy, aryloxy, —S-alkyl, —S(aryl), —OSiR$_3$ and —NR$_2$; and $R^3$ is selected from the group consisting of optionally substituted aryl and optionally substituted heteroaryl, where each optional substituent is independently selected from the group consisting of alkyl, alkoxy, and acyl.

The invention further provides a kit comprising at least one compound of the invention, and instructions for using the at least one compound to catalyze an asymmetric coupling reaction between an imine of formula (II) and a Michael acceptor substrate, and/or to catalyze the enantioselective or diastereoselective isomerization of an imine of formula (II):

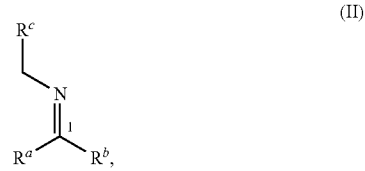

(II)

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S-alkyl, —S(aryl), —OSiR$_3$ and —NR$_2$; or (b) $R^a$ is H, and $R^b$ is selected from the group consisting of optionally substituted aryl, optionally substituted heteroaryl, optionally substituted vinyl, and optionally substituted alkynyl, where each optional substituent is independently selected from the group consisting of alkyl, alkoxy, aryloxy, —S-alkyl, —S(aryl), —OSiR$_3$ and —NR$_2$; and $R^c$ is selected from the group consisting of optionally substituted alkyl, optionally substituted alkenyl, optionally substituted aryl and optionally substituted heteroaryl, where each optional substituent is independently selected from the group consisting of alkyl, alkoxy, aryloxy, —S-alkyl, —S(aryl), —OSiR$_3$ and —NR$_2$.

In certain embodiments, the method comprises contacting the imine, the Michael acceptor substrate and at least one compound of the invention, wherein the imine comprises formula (II):

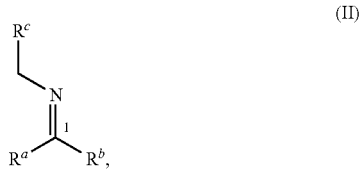

(II)

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S-alkyl, —S(aryl), —OSiR$_3$ and —NR$_2$; or
(b) $R^a$ is H, and $R^b$ is selected from the group consisting of optionally substituted aryl, optionally substituted heteroaryl, optionally substituted vinyl, and optionally substituted alkynyl, where each optional substituent is independently selected from the group consisting of alkyl, alkoxy, aryloxy, —S-alkyl, —S(aryl), —OSiR$_3$ and —NR$_2$; and $R^c$ is selected from the group consisting of optionally substituted alkyl, optionally substituted alkenyl, optionally substituted aryl and optionally substituted heteroaryl, where each optional substituent is independently selected from the group consisting of alkyl, alkoxy, aryloxy, —S-alkyl, —S(aryl), —OSiR$_3$ and —NR$_2$.

The invention further provides methods of isomerizing an imine. In certain embodiments, the imine comprises formula (II):

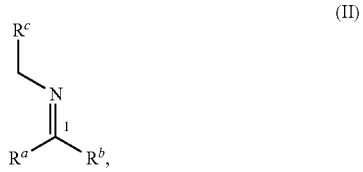

(II)

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S-alkyl, —S(aryl), —OSiR$_3$ and —NR$_2$; or
(b) $R^a$ is H, and $R^b$ is selected from the group consisting of optionally substituted aryl, optionally substituted heteroaryl and optionally substituted vinyl, where each optional substituent is independently selected from the group consisting of alkyl, alkoxy, aryloxy, —S-alkyl, —S(aryl), —OSiR$_3$ and —NR$_2$; and $R^c$ is selected from the group consisting of optionally substituted alkyl, optionally substituted alkenyl, optionally substituted aryl and optionally substituted heteroaryl, where each optional substituent is independently selected from the group consisting of alkyl, alkoxy, aryloxy, —S-alkyl, —S(aryl), —OSiR$_3$ and —NR$_2$.

The invention provides phase-transfer catalysts, compositions comprising the same, and methods of promoting asymmetric addition reactions. Compositions and articles disclosed herein can be isolated or otherwise manufactured in connection with the examples provided below. Other features and advantages of the invention will be apparent from the detailed description and from the claims.

BRIEF DESCRIPTION OF THE DRAWINGS

The following detailed description of exemplary embodiments of the invention can be better understood when read in conjunction with the appended drawings. It should be understood, however, that the invention is not limited to the precise arrangements and instrumentalities of the embodiments shown in the drawings.

FIGS. 3A-3B are a set of compounds (FIG. 3A) and table (FIG. 3B) illustrating results from studies with chiral phase-transfer catalysts. Conditions: 10 mol % catalyst, 10 mol % KOH (aq.), 16 h. TBAB (tetra-n-butylammonium bromide). ND, not determined; d.r., diastereomeric ratio; e.e., enantiomeric ratio. *1.0 mol % catalyst, 10 mol % KOH (aq.), 2 h. †0.2 mol % of C-21b used, 5 h.

FIGS. 4A-4B are a set of reactions and tables illustrating an exemplary substrate scope for umpolung reactions of trifluoromethyl imines with enals. Conditions: imine 1 (0.2 mmol), aldehyde 8 (0.4 mmol), C-21b (0.2 mol %), KOH (2.2 ml, 50 wt % aq., 10 mol %), PhMe (2.0 ml). Conversion, regioselectivity (9/10) and d.r. of 9 were determined by $^1$H NMR analysis of the crude umpolung reaction mixture. Chemoselectivity (9/4) was determined by $^{19}$F NMR analysis. *Overall yield for the transformation of imine 1 to either 22 or 23. †e.e. of 22 or 23, determined by HPLC analysis. Reaction was performed at −10° C.

FIG. 5A: Gram-scale catalytic asymmetric umpolung reaction of imine 1A (1.5 g) with 0.01 mol % of C-21b (0.6 mg) and its application for the syntheses of amino-alcohol 23Aa and pyrrolidine 24Aa. FIG. 5B: Synthetic application of catalytic asymmetric umpolung reaction of imine 1G for the syntheses of amine 9Ge and pyrrolidine 24Ge.

FIG. 6A: Left, 2-azaallyl anion 26 derived from deprotonation of phenyl imine 25; right, 2-azaallyl anion 28 derived from deprotonation of alkenyl imine 27. FIG. 6B: Catalyst optimization for the umpolung reaction of phenyl imine 25A with enal 8e.

Figure 8:
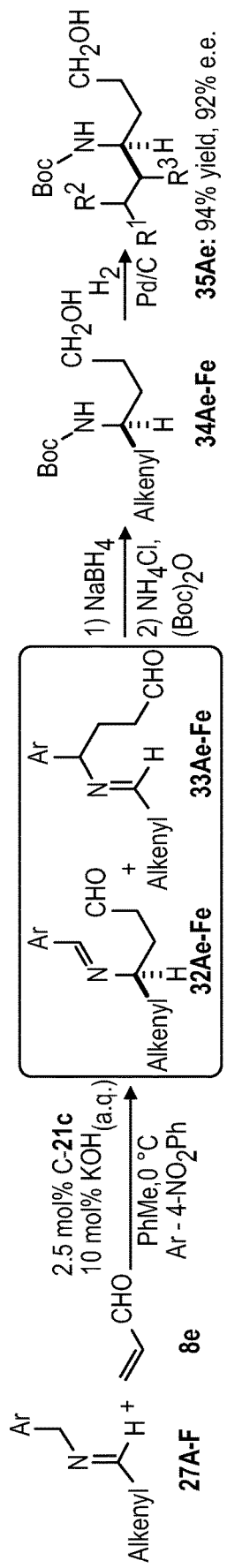

FIG. 8 is a set of reactions and table illustrating an exemplary substrate scope for umpolung reactions of alkenyl aldimines with acrolein (8e). Conditions: reactions were performed with 27 (0.20 mmol), 8e (0.40 mmol), C-21c (2.5 mol %) and KOH (2.2 ml, 50 wt % aq., 10 mol %) in PhMe (2.0 ml) until full conversion. Regioselectivity (32/33) was determined by $^1$H analysis of the crude umpolung reaction mixture. *Overall yield for the transformation of imine 27 to 34. †Determined by HPLC analysis. ‡5.0 mol % C-21c used. § Overall yield for a four-step transformation of (E)-3-bromobut-2-enal to 34Fe.

Figure 9:
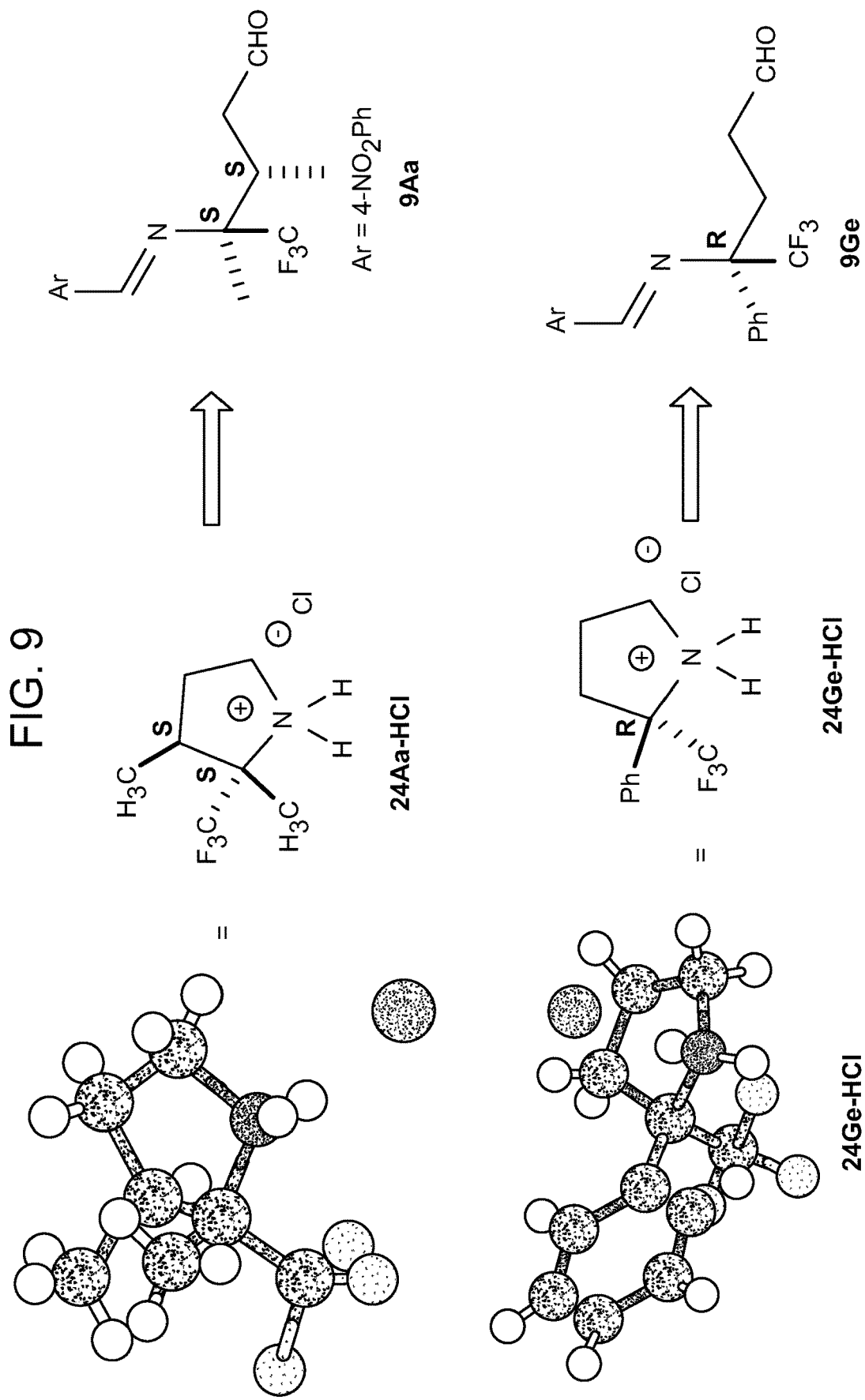

FIG. 9 illustrates certain compounds of the invention.

DETAILED DESCRIPTION OF THE INVENTION

The present invention relates to the unexpected discovery of phase-transfer catalysts that can be used to promote carbon-carbon formation using 2-azaallyl anions. Such reactions proceed in a highly chemoselective, regioselective and enantioselective manner. In certain embodiments, the catalysts of the present invention allow for the asymmetric preparation of chiral amines. The present invention further comprises compositions comprising one or more of the catalysts contemplated within the invention, and methods of preparing certain organic compounds using catalysts of the present invention.

The present disclosure describes the discovery and development of chiral phase-transfer catalysts that promote the highly efficient asymmetric umpolung reactions of imines with the carbon electrophile enals. These catalysts mediate the deprotonation of imines and direct the 2-azaallyl anions thus formed to react with enals in a highly chemoselective, regioselective, diastereoselective and enantioselective fashion. The reaction tolerates a broad range of imines and enals, and can be carried out in high yield with as little as about 0.01 mole percent catalyst with a moisture- and air-tolerant operational protocol. These umpolung reactions provide a practical and efficient approach to chiral amino compounds.

Figure 1:
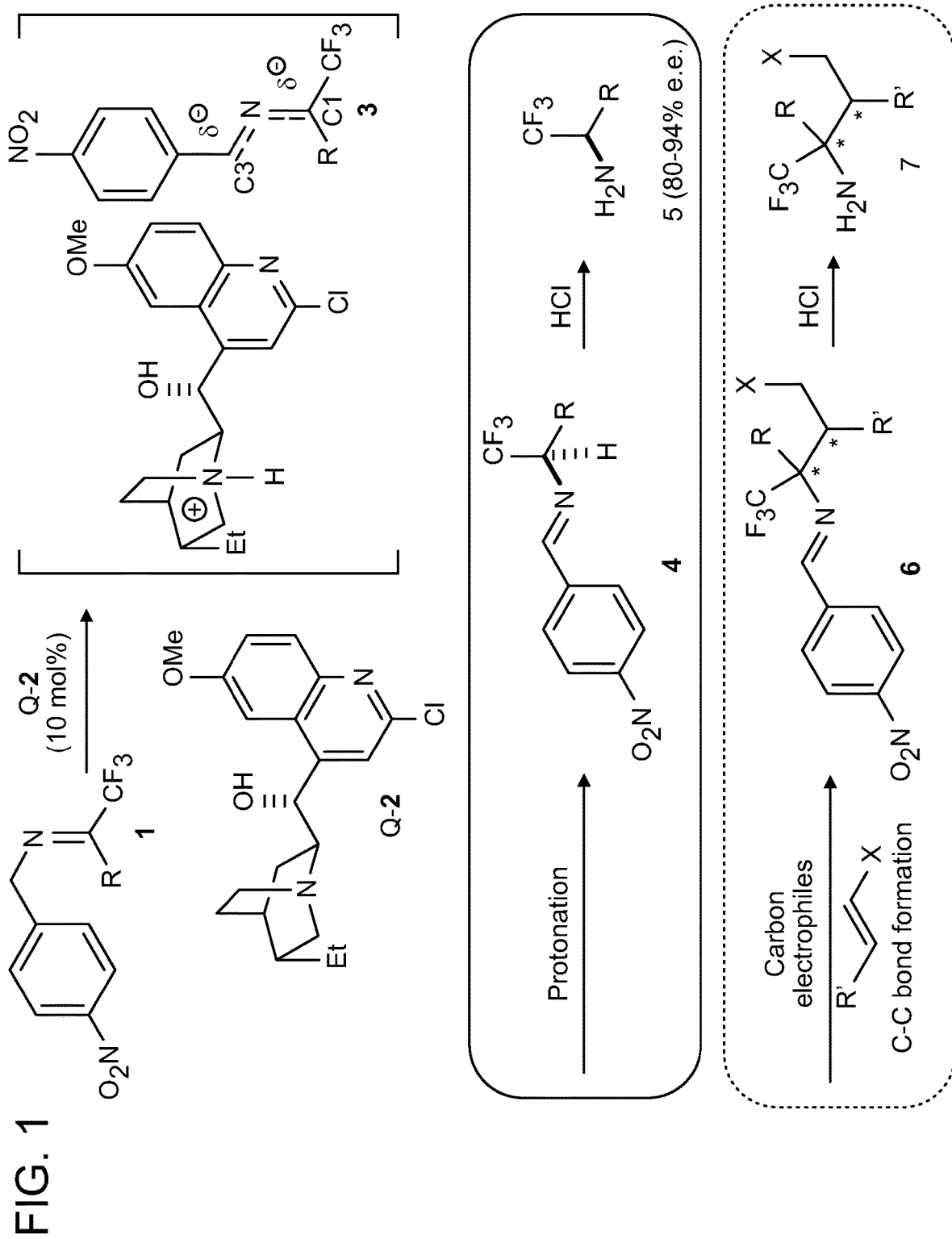
FIG. 1 is a schematic illustration of a non-limiting design of a catalytic C—C bond-forming an umpolung reaction of imines.

Modified cinchona alkaloids such as the quinine-derived (Q) catalyst Q-2 can promote highly enantioselective isomerization of trifluoromethyl imines such as 1 (FIG. 1). Without wishing to be limited by any theory, this reaction may proceed through the initial formation of the 2-azaallyl anion 3, and then a highly enantioselective protonation of 3. If the 2-azaallyl anion 3 reacts with carbon electrophiles in a stereoselective manner, novel CC bond-forming asymmetric reactions transforming imines 1 into enantio-enriched amines may be realized (FIG. 1).

Figure 2:
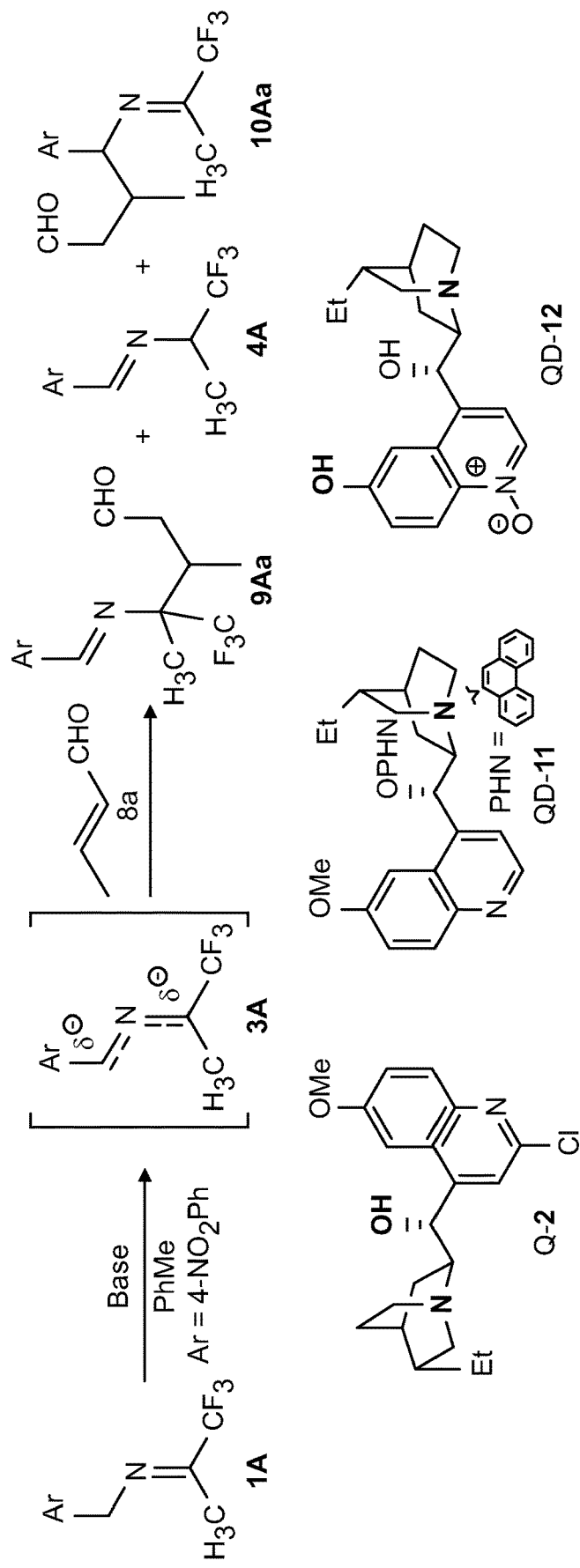
FIG. 2 is a set of reactions and table illustrating results from studies with chiral base catalysts. Conditions: room temperature (RT), 10 mol % catalyst, 16 hours.

Quinine- and quinidine-derived (QD) organocatalysts Q-2, QD-11 and QD-12 were investigated for the reaction of imine 1A and crotonaldehyde 8a (FIG. 2). None of the catalysts produced detectable amounts of the umpolung C—C bond-forming reaction; only the isomerized imine 4A was detected. These catalysts promoted the deprotonation of trifluoromethyl imine 1A to form the 2-azaallyl anion 3, but appeared to be unable to direct the conjugate addition of 3 to crotonaldehyde. In certain embodiments, the protonated cinchona alkaloids formed on deprotonation of 1A, which rapidly protonated 3 to form 4A. As the 2-azaallyl anion 3 engages in protonation in the presence of a proton donor, this disclosed class of catalysts affords the required chemoselectivity, in favor of the C—C bond formation over the protonation.

Chiral phase-transfer catalysts were then explored. Under phase-transfer catalysis conditions, stronger bases can be explored for the deprotonation of imine 1 to form 2-azaallyl anion 3. Furthermore, in the absence of a protonated cationic species, 3 should be less prone to protonation, and thus more likely to engage in addition to 8a. A cinchonine-derived (C) phase-transfer catalyst C-13 was investigated to promote the reaction of 1A and 8a in toluene and aqueous KOH at room temperature. The expected amine 9Aa was formed, albeit in low yield (entry 1, FIG. 3B). The chemoselectivity for the C—C bond formation was improved with catalyst C-14 bearing PYR, a bulky heteroaryl group (FIG. 3A), although both the reaction conversion and the chemoselectivity remained moderate (entry 2, FIG. 3B). A reaction at lower temperature afforded significantly improved conversion and chemoselectivity. The absence of 10Aa, which would be formed by conjugate addition from the other end of the 2-azaallyl anion, was noted. However, amine 9Aa was formed with moderate diastereoselectivity and poor enantioselectivity.

Without wishing to be limited by any theory, a cinchonine-derived phase-transfer catalyst bearing a properly located aromatic group with suitable electronic properties may interact with 2-azaallyl anion 3A via both ionic and π-π interactions, thereby mediating the disclosed umpolung reaction in a highly chemo-, regio-, diastereo- and enantioselective fashion. Analogues C-15 and C-16 bearing electron-withdrawing and electron-donating N-benzyl substituents, respectively, were examined. C-16 afforded only improved conversion rather than selectivity as well, whereas C-15 was lower yielding than C-14 (entries 4-5, FIG. 3B). A decrease in the loading of C-16 did not affect the catalytic selectivities negatively (entry 6 vs. 5, FIG. 3B). The catalyst loading was thus decreased from 10 mol % to 1 mol % in subsequent catalyst screening and optimization studies. C-17, an analogue containing a biphenyl group, was also studied. C-17 afforded substantially improved chemo-, diastereo- and enantioselectivity, thereby allowing amine 9Aa to be formed as the major product (entry 7 vs. 6, FIG. 3B).

Figure 3A:
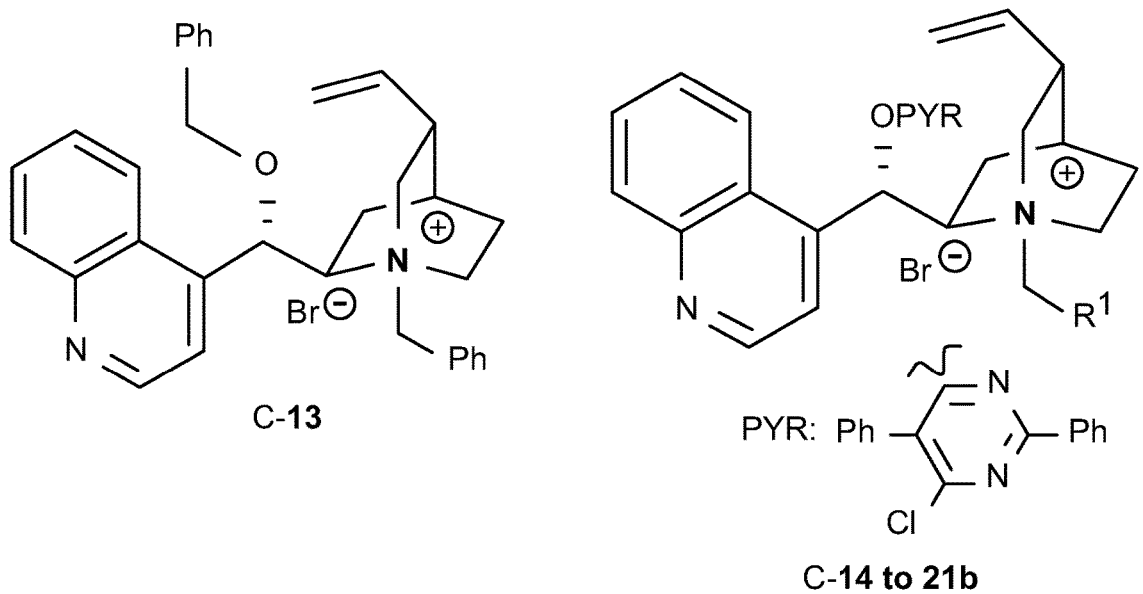
Figure 3A:
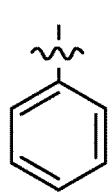
Figure 3A:
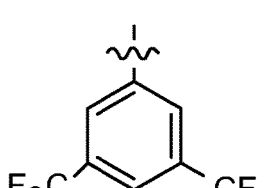
Figure 3A:
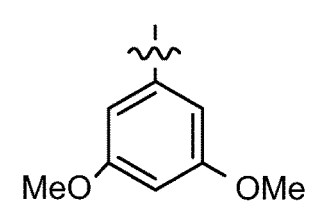
Figure 3A:
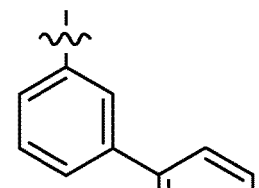
Figure 3A:
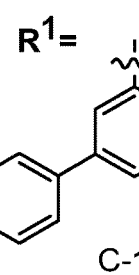
Figure 3A:
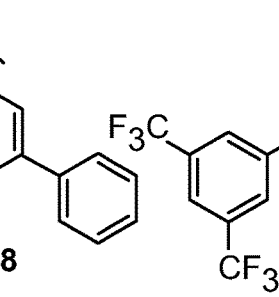
Figure 3A:
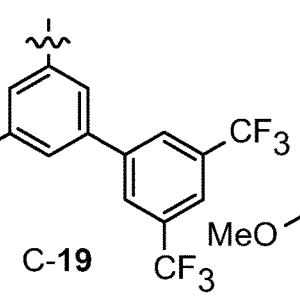
Figure 3A:
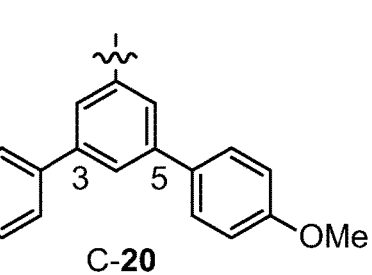
Figure 3A:
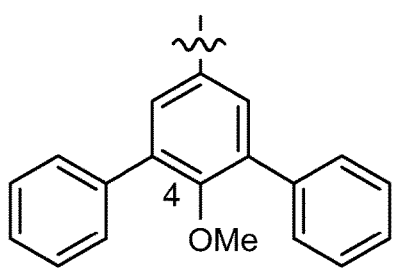

Catalyst C-18 was prepared and studied (FIG. 3A). Without wishing to be limited by any theory, the presence of the C2-symmetric terphenyl moiety may render C-18 a more efficient catalyst than C-17. Indeed, C-18 showed improved performance in catalytic activity as well as chemo- and enantioselectivity (entry 8 vs. 7, FIG. 3B). Further tuning of the terphenyl moiety was attempted by introducing electron-withdrawing and electron-donating groups on the 3- and 5-phenyl groups. Catalyst C-20 (entry 10, FIG. 3B) bearing an electron-rich terphenyl group performed better than C-19 (entry 9), which contained an electron-deficient terphenyl moiety. C-20 furnished higher stereoselectivity but lower chemoselectivity than those produced by C-18 (entry 10 vs. 8, FIG. 3B).

Catalyst C-21a (FIG. 3A) was designed to create an electron-rich terphenyl moiety with an electron-donating substituent in a position not causing obstructive steric interference between the catalyst and 2-azaallyl anion 3. C-21a not only was a much more active catalyst, but also afforded 9Aa with synthetically useful chemo-, regio-, diastereo- and enantioselectivity (entry 11, FIG. 3B). Catalyst C-21b with a more electron-donating and bulky tert-butyldimethylsilyl ether (OTBS) group was more active and selective; a loading of only 0.2 mol % produced imine 9Aa rapidly with very high chemoselectivity and stereoselectivity (entry 13, FIG. 3B). Without wishing to be limited by any theory, the increased performance of C-21b over C-21a may be explained by at least two factors resulting from the substitution of the 4-methoxy with the 4-OTBS group: the terphenyl moiety is more electron rich due to the presence of the more electron-donating 4-OTBS group; and the terphenyl moiety has less conformational flexibility due to steric hindrance of the rotation of the 3,5-phenyl rings by the bulky 4-OTBS group. Both factors may reinforce the π-π interaction between 3A and the catalyst C-21b.

Only a trace of 9Aa was formed from 1A and 8a using tetrabutylammonium bromide (TBAB) as the quaternary ammonium salt (entry 14, FIG. 3B), which may indicate that the structural characteristics of C-21b were responsible for both the catalytic activity and the selectivity observed for the umpolung reaction between imine 1A and enal 8a. Consistent with the observation that 2-azaallyl anion 3 apparently originated only from imine 1 rather than also from the isomerized imine 4, no reaction occurred between 4A and 8a under the optimized conditions. Amine 9Aa could also form via a [3+2] cycloaddition between 1A and 8a followed by a retro-Mannich reaction. However, the formation of the [3+2] adduct was not detected when monitoring the reaction by $^1$H and $^{19}$F NMR analyses.

Figure 4A:
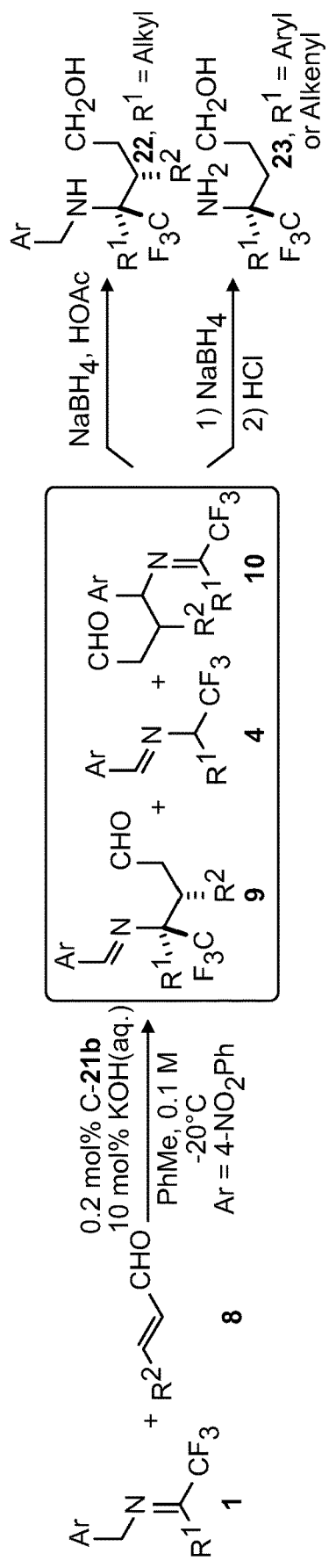

Investigation of the substrate scope began with the reaction of 1A and 8a with 0.2 mol % of C-21b (entry 1, FIG. 4A). The reaction proceeded to detectably full conversion within 5 h with high chemo-, regio-, diastereo- and enantioselectivities. The optically active amine 9Aa was then converted to the more stable N-benzyl amino-alcohol 22Aa by reducing first the aldehyde with $NaBH_4$, and then the imine with $NaBH_4$ and acetic acid, which could be readily isolated as a high diastereomeric excess and in good yield. Reactions of 8a with a series of trifluoromethyl imines (1B-1E, FIG. 4A) bearing simple and functionalized linear alkyl substituents consistently proceeded in high yield, chemoselectivity and stereoselectivity. The reaction tolerated an imine bearing a β-branched alkyl substituent (1F). The reaction accepted larger β-alkyl groups on the enal (entries 7-8, FIG. 4B). Cinnamaldehyde (8d) reacted with 1A to give a 68:32 mixture of the desirable amine 9Ad and the regioisomer 10Ad. 9Ad was produced with high chemo-, diastereo- and enantioselectivity in synthetically useful yield (entry 9, FIG. 4B).

The reactions of trifluoromethylated imines 1 with acrolein (8e) were examined. At −10° C. the reaction between 1A and 8e proceeded without significant levels of side products and in a highly enantioselective fashion to furnish the corresponding amine 9Ae as the only detectable product by NMR analysis of the crude reaction mixture. The reactions of acrolein (8e) with trifluoromethyl imines 1 bearing a variety of alkyl, aryl and alkenyl substituents were equally successful, affording the corresponding trifluoromethylated amines 9 containing a tetrasubstituted stereocenter in high optical purity (entries 11-17, FIG. 4B). Alkyl trifluoromethylated amines (9Ae-9Fe) were converted to N-benzyl amino-alcohols 22 (entries 10-13, FIG. 4B). Aryl and alkenyl amines 9Ge-9Je were converted to amino-alcohols 23 by reduction of the aldehyde with $NaBH_4$ and hydrolysis of the imine with aqueous HCl (entries 14-17, FIG. 4B). In all these cases, the amino-alcohols 22 and 23 were obtained in good yields and high optical purity.

Figure 5A:
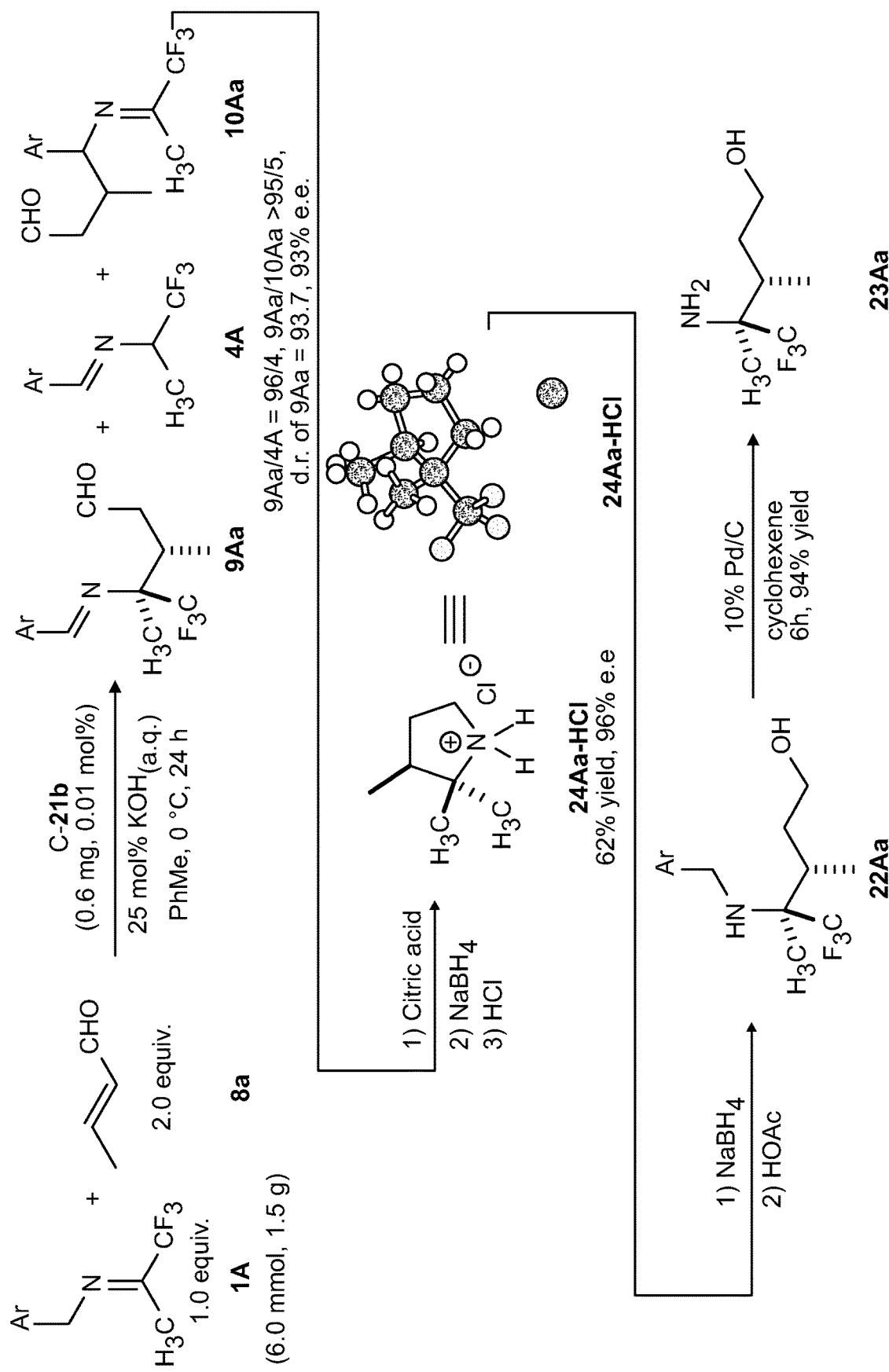
FIGS. 5A-5B illustrate gram-scale reactions and synthetic applications of catalysts of the invention.
Figure 5B:
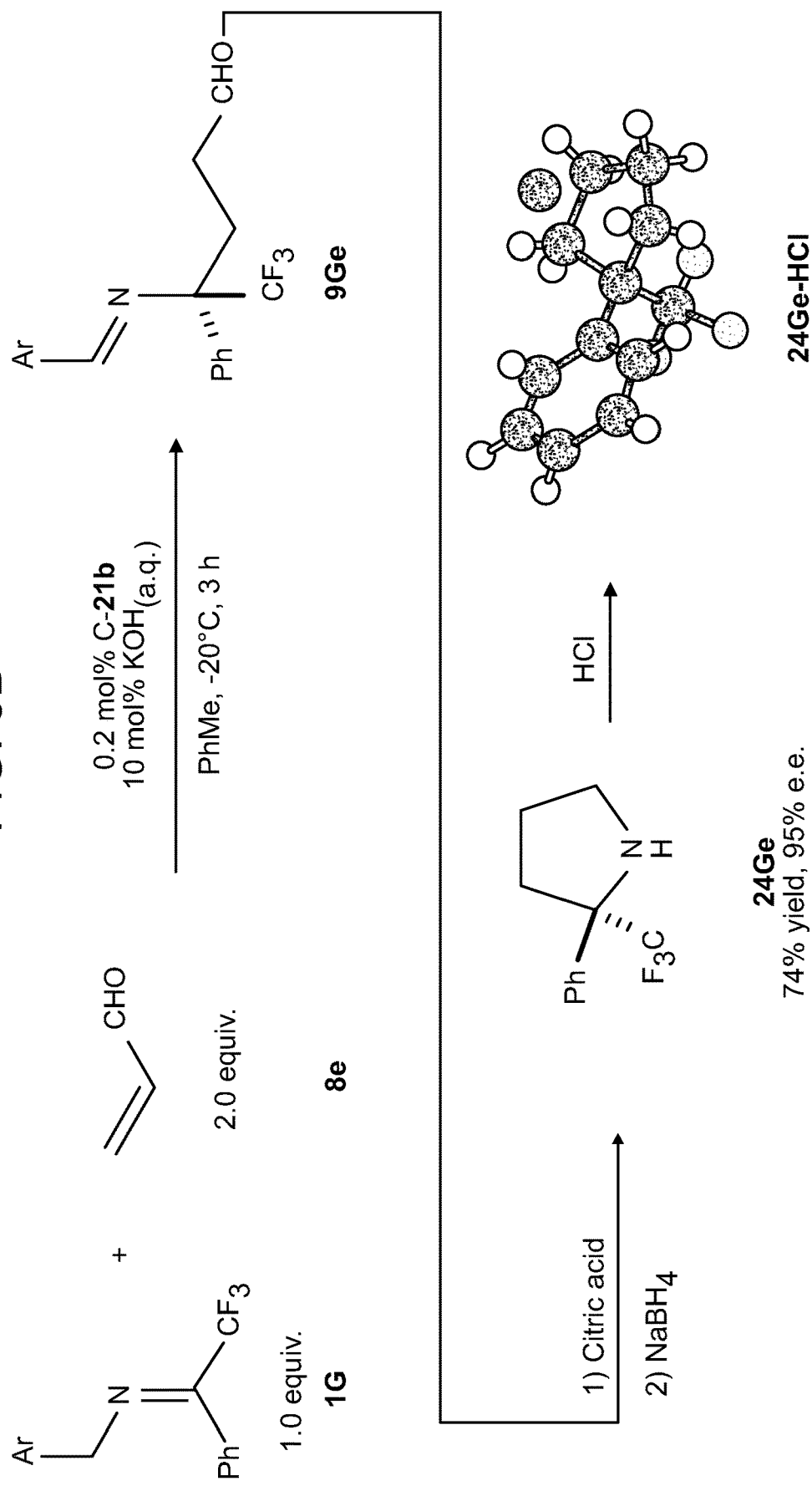

A gram-scale reaction of 1A with 8a with 0.01 mol % of C-21b proceeded in high yield without deterioration in selectivity (FIG. 5A). This catalytic efficiency indicates the utility of this new reaction in preparative-scale organic synthesis. To demonstrate the synthetic versatility of this reaction, chiral amino-aldehyde 9Aa was converted to amino-alcohol 23Aa and pyrrolidine 24Aa (FIG. 5A). Similarly, the phenyl substituted product 9Ge was converted to pyrrolidine 24Ge (FIG. 5B). The absolute configurations of 24Aa and 24Ge were determined by X-ray crystallography.

Figure 6A:
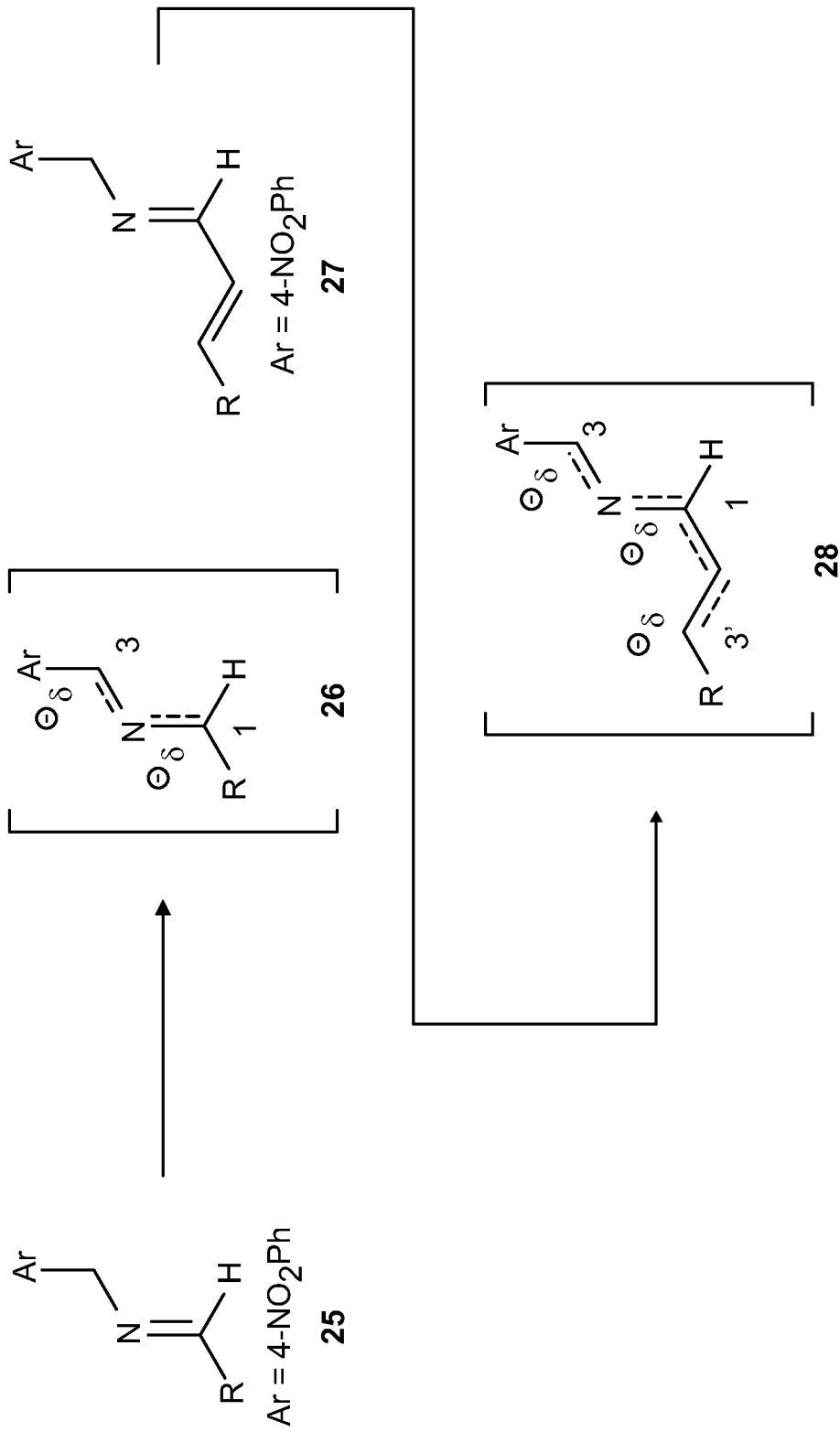
FIGS. 6A-6B illustrates asymmetric umpolung reactions of aryl and unsaturated aldimines.
Figure 6B:
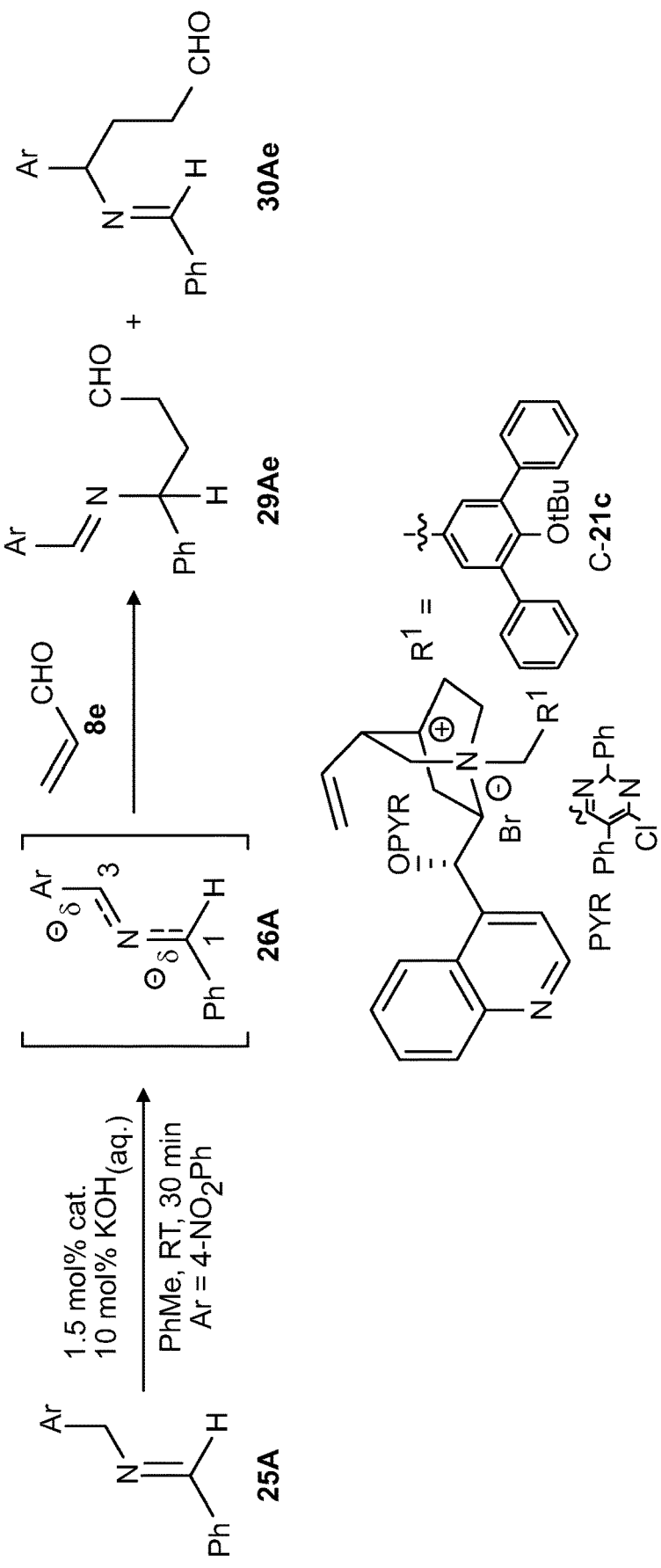

The use of the present reaction with simple imines was investigated. 2-Azaallyl anions 26 derived from aryl imines 25 (FIG. 6A) are less stable than those derived from the corresponding trifluoromethyl imines 1. Without wishing to be bound by any theory, the regioselectivity control obtained in the electrophilic reaction with an unsymmetrically substituted 1,3-diaryl-2-azaallyl anion 26 might prove difficult (FIG. 6A). In certain non-limiting embodiments, deprotonation of phenyl imine 25A may form 2-azaallyl anion 26A, which is flanked by the phenyl and the 4-nitrophenyl rings (FIG. 6B). Thus, there may be an electronic bias for an electrophile to react with 26A by attacking preferentially the more electron-rich C3. In certain non-limiting embodiments, the catalytic activity and efficiency of C-21b may overcome this substrate bias, while still affording the expected stereoselectivity for an efficient asymmetric imine umpolung reaction.

Figure 7:
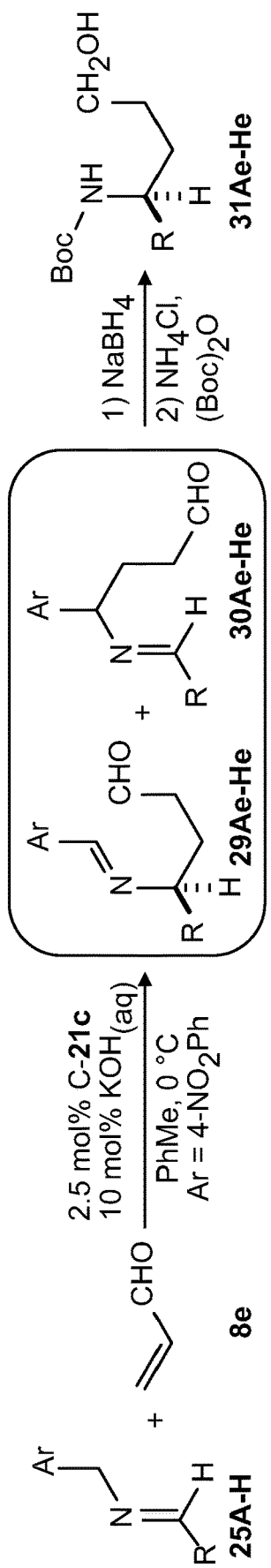
FIG. 7 is a set of reactions and table illustrating substrate scope for umpolung reactions of aryl aldimines with acrolein (8e). Conditions: reactions were performed with 25 (0.20 mmol), 8e (0.40 mmol), C-21c (2.5 mol %) and KOH (2.2 ml, 50 wt % aq., 10 mol %) in PhMe (2.0 ml) until full conversion. Regioselectivity (29/30) was determined by $^1$H analysis of the crude umpolung reaction mixture. *Overall yield for the transformation of imine 25 to 31. †Determined by HPLC analysis. ‡Reaction was performed in PhMe/CH$_2$Cl$_2$=2/1 solution (3.0 ml). § 15.0 mol % C-21c used.

The reaction of phenyl imine 25A with acrolein (8e) was investigated applying the conditions established with trifluoromethyl imines 1. As expected, 25A was less reactive than 1A; only a small amount of the product 29Ae was detected. With an increased catalyst loading (entry 1, FIG. 6B), the reaction progressed to high conversion and enantioselectivity. A catalyst bearing a 4-OtBu group (C-21c) was more active and afforded better enantioselectivity (entry 2, FIG. 6B); this clean reaction occurred in high yield at 0° C. in very high enantioselectivity with 2.5 mol % of C-21c (entry 3, FIG. 6B). Amine 29Ae was converted to the Boc-protected amino-alcohol 31Ae in high optical purity and good yield in three steps (entry 1, FIG. 7). The umpolung reaction tolerated a broad range of aryl and heteroaryl aldimines of varying steric and electronic properties (entries 2-8, FIG. 7). Electron-rich aryl imines such as 25H appeared to be less active, but the umpolung reaction with C-21c still gave a very high yield with high chemoselectivity, regioselectivity and enantioselectivity.

Owing to the synthetic versatility of the olefin and amine functionalities, chiral allylic amines can be useful chiral building blocks. Without wishing to be bound by any theory, the 2-azaallyl anions 28 derived from α,β-unsaturated imines 27 were expected to be even less stable than those derived from arylaldimines. Furthermore, the conjugation of an azaallyl anion with an olefin may render 28 a less active nucleophile to provide catalytic control of regioselectivity (FIG. 6A). C-21c provided highly selective catalysis to efficiently promote the umpolung reaction of 27A and 8e (entry 1, FIG. 8). In some embodiments, the efficiency of C-21c remained steady for reactions involving a variety of α,β-unsaturated imines bearing di- and trisubstituted olefins (entries 2-6, FIG. 8). As a number of methods are known for hydrogenating allylic amines to the corresponding aliphatic amines (FIG. 8), the imine umpolung reaction disclosed herein is a useful method for the asymmetric synthesis of both chiral allylic and aliphatic amines.

Provided herein is a new class of tunable chiral phase-transfer catalysts which promote C—C bond-forming reactions with 2-azaallyl anions in a highly chemoselective, regioselective, diastereoselective and enantioselective fashion. These catalysts enable imines to act as nucleophiles, thereby allowing the realization of catalytic asymmetric umpolung reactions of imines, and providing a new approach towards chiral amino compounds. With an accessible operational protocol and low catalyst loading, the transformations disclosed herein also provide a practical method for organic synthesis.

Definitions

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, such as ±5%, such as ±1%, and such as ±0.1% from the specified value, as such variations are appropriate to perform the disclosed methods.

As used herein, the term "alkyl", by itself or as part of another substituent means, unless otherwise stated, a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, iso-propyl, n-butyl, iso-butyl, sec-butyl, and tert-butyl. The term "$C_1$-$C_4$ n-alkyl" refers to straight chain hydrocarbon moieties that have 1, 2, 3, or 4 carbon atoms including methyl, ethyl, n-propyl, and n-butyl.

As used herein, the term "alkenyl" by itself or as part of another substituent means, unless otherwise stated, a straight or branched hydrocarbon chain radical group consisting solely of carbon and hydrogen atoms, containing at least one double bond, and having from two to ten carbon atoms (i.e., $C_{2-10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methylprop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like, and the higher homologs and isomers. A non-limiting functional group representing an alkene is exemplified by —$CH_2$—CH=$CH_2$.

As used herein, the term "alkoxy" by itself or as part of another substituent means, unless otherwise stated, an —O-alkyl group, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. In some embodiments, an alkoxy group can have one to six carbons denoted $C_1$-$C_3$. In some embodiments, $C_{1-4}$ alkoxy is an alkoxy group which encompasses both straight and branched chain alkyls of from 1 to 4 carbon atoms. In some aspects, the alkoxy group is a ($C_1$-$C_3$)alkoxy, such as, but not limited to, ethoxy and methoxy.

As used herein, the term "alkynyl" employed alone or in combination with other terms means, unless otherwise stated, a stable straight chain or branched chain hydrocarbon group with a triple carbon-carbon bond, having the stated number of carbon atoms (i.e., $C_2$-$C_{10}$ means two to ten carbon atoms, $C_2$-$C_6$ means two to six carbon atoms). Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "aromatic" refers to a carbocycle or heterocycle with one or more polyunsaturated rings and having aromatic character, i.e. having (4n+2) delocalized π (pi) electrons, where n is an integer.

In one embodiment, sites on, for example, the aromatic ring portion of compounds of the invention are susceptible to various unwanted transforming reactions. Incorporation of appropriate substituents on the aromatic ring structures may reduce, minimize or eliminate these pathways. In one embodiment, the appropriate substituent to decrease or eliminate the susceptibility of the aromatic ring to unwanted transformations is, by way of example only, a deuterium, a halogen, or an alkyl group.

As used herein, the term "aryl" or "arene" employed alone or in combination with other terms means, unless otherwise stated, a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like.

As used herein, the term "arylalkyl" by itself or as part of another substituent means, unless otherwise stated, a functional group wherein a one to three carbon alkylene chain is attached to an aryl group, e.g., —CH$_2$CH$_2$-phenyl or —CH$_2$-phenyl (benzyl). The term "substituted aryl-(C$_1$-C$_3$)alkyl" means an aryl-(C$_1$-C$_3$)alkyl functional group in which the aryl group is substituted. Non-limiting examples include aryl-CH$_2$— and aryl-CH(CH$_3$)—. In one aspect, the arylalkyl group is a substituted aryl(CH$_2$)—. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. In one aspect, the heteroarylalkyl group is a heteroaryl-(CH$_2$)—. The term "substituted heteroaryl-(C$_1$-C$_3$)alkyl" means a heteroaryl-(C$_1$-C$_3$)alkyl functional group in which the heteroaryl group is substituted. In one aspect, the heteroarylalkyl group is a substituted heteroaryl-(CH$_2$)—.

As used herein, the term "cycloalkyl" by itself or as part of another substituent means, unless otherwise stated, a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., C$_3$-C$_{13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a C$_3$-C$_8$ cycloalkyl radical. In some embodiments, it is a C$_3$-C$_6$ cycloalkyl radical. Illustrative examples of cycloalkyl groups include, but are not limited to the following moieties: C$_{3-6}$ carbocyclyl groups include, without limitation, cyclopropyl (C$_3$), cyclobutyl (C$_4$), cyclopentyl (C$_5$), cyclopentenyl (C$_5$), cyclohexyl (C$_6$), cyclohexenyl (C$_6$), cyclohexadienyl (C$_6$) and the like. Examples of C$_{3-7}$ carbocyclyl groups include norbornyl (C$_7$). Examples of C$_{3-8}$ carbocyclyl groups include the aforementioned C$_{3-7}$ carbocyclyl groups as well as cycloheptyl(C$_7$), cycloheptadienyl (C$_7$), cycloheptatrienyl (C$_7$), cyclooctyl (C$_8$), bicyclo[2.2.1]heptanyl, bicyclo[2.2.2]octanyl, and the like. Examples of C$_3$-C$_{13}$ carbocyclyl groups include the aforementioned C$_{3-8}$ carbocyclyl groups as well as octahydro-1H indenyl, decahydronaphthalenyl, spiro[4.5]decanyl and the like.

As used herein, the term "δ" refers to delta (ppm).

As used herein, the term "DMSO" refers to dimethylsulfoxide.

As used herein, the term "halo" or "halogen" employed alone or as part of another substituent means, unless otherwise stated, a fluorine, chlorine, bromine, or iodine atom, such as fluorine, chlorine, or bromine, further such as, fluorine or chlorine.

As used herein, the term "heteroalkyl" by itself or in combination with another term means, unless otherwise stated, a stable straight or branched chain alkyl group which have one or more skeletal chain atoms selected from an atom other than carbon, e.g., oxygen, nitrogen, sulfur, phosphorus or combinations thereof. A numerical range can be given, e.g., C$_1$-C$_4$ heteroalkyl which refers to the chain length in total, which in this example is 4 atoms long. For example, a —CH$_2$OCH$_2$CH$_3$ radical is referred to as a "C$_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. In some aspects, the heteroalkyl group has one or two heteroatoms selected from the group consisting of O, N, and S. Exemplary heteroalkyl groups include, without limitation, ethers such as methoxyethanyl (—CH$_2$CH$_2$OCH$_3$), ethoxymethanyl (—CH$_2$OCH$_2$CH$_3$), (methoxymethoxy)ethanyl (—CH$_2$CH$_2$OCH$_2$OCH$_3$), (methoxymethoxy) methanyl (—CH$_2$OCH$_2$OCH$_3$) and (methoxyethoxy)methanyl (—CH$_2$OCH$_2$CH$_2$OCH$_3$) and the like; amines such as (—CH$_2$CH$_2$NHCH$_3$, —CH$_2$CH$_2$N(CH$_3$)$_2$, —CH$_2$NHCH$_2$CH$_3$, —CH$_2$N(CH$_2$CH$_3$)(CH$_3$)) and the like. Other examples include —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$ S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "heterocycle", by itself or as part of another substituent means, unless otherwise stated, an unsubstituted or substituted, stable, mono- or multi-cyclic heterocyclic ring system that consists of carbon atoms and at least one heteroatom. A heterocycle refers to any 3- to 18-membered non-aromatic radical monocyclic or polycyclic moiety comprising at least one heteroatom selected from nitrogen, oxygen, phosphorous and sulfur. In some aspects, the heteroatom(s) are chosen from N, O, and S. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e] [1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

As used herein, the term "heteroaryl" or "heteroaromatic", by itself or as part of another substituent means, unless otherwise stated, a 5-18 membered monocyclic or polycyclic (e.g., bicyclic or tricyclic) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms.

For example, an N-containing "heteroaryl" or "heteroaromatic" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo [h]quinazolinyl, 5,6-dihydrobenzo[h]cinnolinyl, 6,7-dihydro-5H benzo[6,7]cyclohepta[ 1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d] pyridazinyl, 5,6,7,8,9,10 hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimdinyl, 6,7,8,9-tetrahydro-5H-cyclohepta[4,5]thieno [2,3-d]pyrimidinyl, 5,6,7, 8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl).

Further examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. The aforementioned listings of heterocyclyl and heteroaryl moieties are intended to be representative and not limiting.

As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

As used herein, the term "isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ----- which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

ee=(90−10)/100=80%.

Thus, a composition containing 90% of one enantiomer and 10% of the other enantiomer is said to have an enantiomeric excess of 80%. Some compositions described herein contain an enantiomeric excess of at least about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has a —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, Enantiomers, Racemates and Resolutions (Jacques, Ed., Wiley Interscience, New York, 1981); Wilen et al., Tetrahedron 33:2725 (1977); Stereochemistry of Carbon Compounds (E. L. Eliel, Ed., McGraw-Hill, NY, 1962); and Tables of Resolving Agents and Optical Resolutions p. 268 (E. L. ElM, Ed., Univ. of Notre Dame Press, Notre Dame, Ind. 1972).

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}F$, and $^{35}S$. In one embodiment, substitution with heavier isotopes such as deuterium affords greater stability (for example, increased half-life or reduced loading requirements). Isotopically-labeled compounds are prepared by any suitable method or by processes using an appropriate isotopically-labeled reagent in place of the non-labeled reagent otherwise employed.

As used herein, the term "instructional material" includes a publication, a recording, a diagram, or any other medium of expression that may be used to communicate the usefulness of the compounds, compositions and methods of the invention. In some instances, the instructional material may be part of a kit useful for promoting asymmetric reactions. The instructional material of the kit may, for example, be affixed to a container that contains the compounds or compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

As used herein, the term "salt" refers to a salt of a compound contemplated within the invention, including inorganic acids, organic acids, inorganic bases, organic bases, solvates, hydrates, or clathrates thereof. As used herein, the term "salt" embraces addition salts of free acids or free bases that are compounds useful within the invention. In some cases, undesired salts may nonetheless possess properties such as high crystallinity, which may have utility in the practice of the present invention, such as, for example, utility in process of synthesis or purification of compounds useful within the methods of the invention.

Suitable acid addition salts may be prepared from an inorganic acid or an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy-ethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzyl-ethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "substituted" means that an atom or group of atoms has replaced hydrogen as the substituent attached to another group. Unless stated otherwise, any group recited within the invention may be substituted.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic, such as straight.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

Compounds

In one aspect, the invention provides certain compounds that may be used as phase-transfer catalysts.

In certain embodiments, the invention provides a compound, or a salt, N-oxide, tautomer, enantiomer or diastereoisomer thereof, of formula (I):

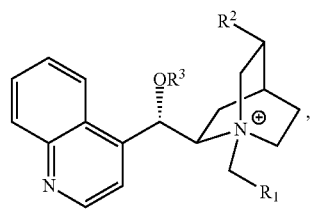

(I)

wherein:
$R^1$ is

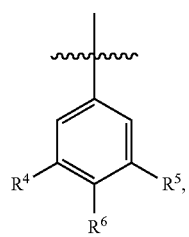

$R^4$ and $R^5$ are independently selected from the group consisting of H, alkyl, alkoxy and aryl, where each occurrence of aryl in $R^4$ or $R^5$ is independently optionally substituted with at least one substituent selected from alkyl, alkoxy, aryloxy, —S-alkyl, —S(aryl), —OSiR$_3$ and —NR$_2$;

$R^6$ is selected from the group consisting of H, alkyl, alkoxy, aryloxy, —S(alkyl), —S(aryl), —OSiR$_3$ and —NR$_2$, and each occurrence of R is independently selected from alkyl and aryl;

$R^2$ is selected from the group consisting of optionally substituted alkyl, optionally substituted alkenyl and optionally substituted alkynyl, where each optional substituent is independently selected from the group consisting of alkyl, alkoxy, aryloxy, —S-alkyl, —S(aryl), —OSiR$_3$ and —NR$_2$; and $R^3$ is selected from the group consisting of optionally substituted aryl and optionally substituted heteroaryl, where each optional substituent is independently selected from the group consisting of alkyl, alkoxy, and acyl.

In certain embodiments, $R^4$ is selected from the group consisting of alkyl, alkoxy and aryl.

In certain embodiments, $R^4$ and $R^5$ are independently selected from the group consisting of alkyl, alkoxy and aryl.

In certain embodiments, $R^4$ is aryl.

In certain embodiments, at least one selected from the group consisting of $R^4$ and $R^5$ is aryl, which is independently optionally substituted with at least one substituent selected from alkyl, alkoxy, —S(alkyl), and —OSiR$_3$.

In certain embodiments, $R^4$ and $R^5$ are both independently aryl, each of which is independently optionally substituted with at least one substituent selected from alkyl, alkoxy, —S(alkyl), and —OSiR$_3$.

In certain embodiments, $R^6$ is selected from the group consisting of alkyl, alkoxy, aryloxy, —S(alkyl), —S(aryl), —OSiR$_3$ and —NR$_2$. In other embodiments, $R^6$ is selected from the group consisting of alkoxy and —OSiR$_3$.

In certain embodiments, each occurrence of R is independently alkyl.

In certain embodiments, $R^1$ is selected from the group consisting of 3,5-dimethoxyphenyl, 3-phenyl-phenyl, 3,5-diphenyl-phenyl, 3,5-(4-methoxyphenyl)-phenyl, 3,5-diphenyl-4-methoxy-phenyl and 3,5-diphenyl-4-(t-butyldimetylsiloxy)-phenyl.

In certain embodiments, $R^2$ is selected from the group consisting of unsubstituted alkyl, unsubstituted alkenyl and unsubstituted alkynyl. In other embodiments, $R^2$ is selected from the group consisting of unsubstituted alkyl and unsubstituted alkenyl. In yet other embodiments, $R^2$ is selected from the group consisting of vinyl and ethyl.

In certain embodiments, $R^3$ is selected from the group consisting of optionally substituted phenyl, optionally substituted pyrimidinyl, and optionally substituted phenanthryl. In other embodiments, $R^3$ is selected from the group consisting of 4-chloro-2,5-diphenyl-pyridin-6-yl and phenanthr-9-yl.

In certain embodiments, the compound is at least one selected from the group consisting of:

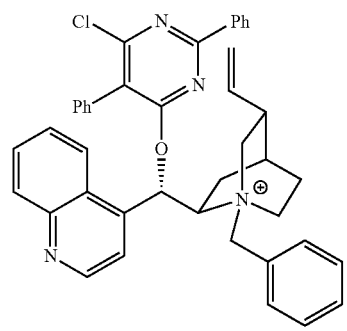 [SMILES: C=CC1C[N+]2(Cc3ccccc3)CCC1CC2[C@@H](Oc1nc(-c2ccccc2)nc(Cl)c1-c1ccccc1)c1ccnc2ccccc12]

(1S,2R,4S,5R)-1-benzyl-2-((S)-((6-chloro-2,5-diphenylpyrimidin-4-yl)oxy)(quinolin-4-yl)methyl)-5-vinylquinuclidin-1-ium (C-14);

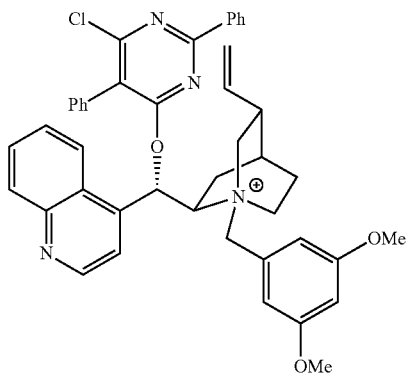 [SMILES: C=CC1C[N+]2(Cc3cc(OC)cc(OC)c3)CCC1CC2[C@@H](Oc1nc(-c2ccccc2)nc(Cl)c1-c1ccccc1)c1ccnc2ccccc12]

(1S,2R,4S,5R)-2-((S)-((6-chloro-2,5-diphenylpyrimidin-4-yl)oxy)(quinolin-4-yl)methyl)-1-(3,5-dimethoxybenzyl)-5-vinylquinuclidin-1-ium (C-16);

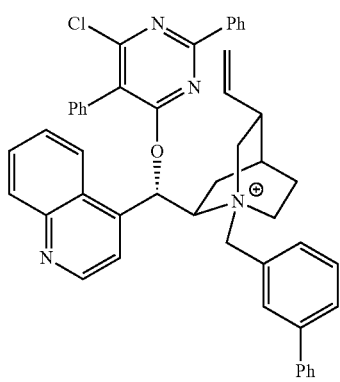 [SMILES: C=CC1C[N+]2(Cc3cccc(-c4ccccc4)c3)CCC1CC2[C@@H](Oc1nc(-c2ccccc2)nc(Cl)c1-c1ccccc1)c1ccnc2ccccc12]

(1S,2R,4S,5R)-1-([1,1'-biphenyl]-3-ylmethyl)-2-((S)-((6-chloro-2,5-diphenylpyrimidin-4-yl)oxy)(quinolin-4-yl)methyl)-5-vinylquinuclidin-1-ium (C-17);

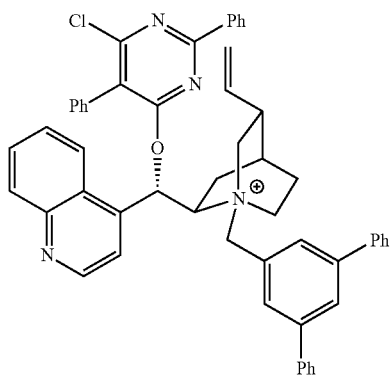 [SMILES: C=CC1C[N+]2(Cc3cc(-c4ccccc4)cc(-c4ccccc4)c3)CCC1CC2[C@@H](Oc1nc(-c2ccccc2)nc(Cl)c1-c1ccccc1)c1ccnc2ccccc12]

(1S,2R,4S,5R)-1-([1,1':3',1''-terphenyl]-5'-ylmethyl)-2-((S)-((6-chloro-2,5-diphenylpyrimidin-4-yl)oxy)(quinolin-4-yl)methyl)-5-vinylquinuclidin-1-ium (C-18);

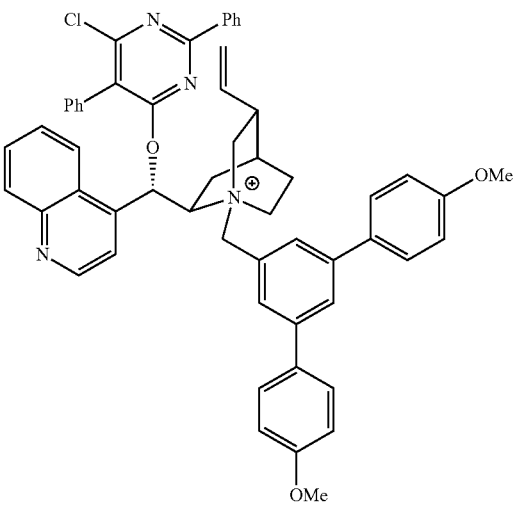 [SMILES: C=CC1C[N+]2(Cc3cc(-c4ccc(OC)cc4)cc(-c4ccc(OC)cc4)c3)CCC1CC2[C@@H](Oc1nc(-c2ccccc2)nc(Cl)c1-c1ccccc1)c1ccnc2ccccc12]

(1S,2R,4S,5R)-2-((S)-((6-chloro-2,5-diphenylpyrimidin-4-yl)oxy)(quinolin-4-yl)methyl)-1-((4,4''-dimethoxy-[1,1':3',1''-terphenyl]-5'-yl)methyl)-5-vinylquinuclidin-1-ium (C-20);

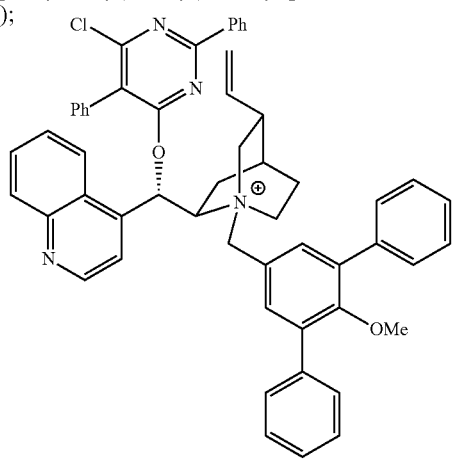

(1S,2R,4S,5R)-2-((S)-((6-chloro-2,5-diphenylpyrimidin-4-yl)oxy)(quinolin-4-yl)methyl)-1-((2'-methoxy-[1,1':3',1''-terphenyl]-5'-yl)methyl)-5-vinylquinuclidin-1-ium (C-21a);

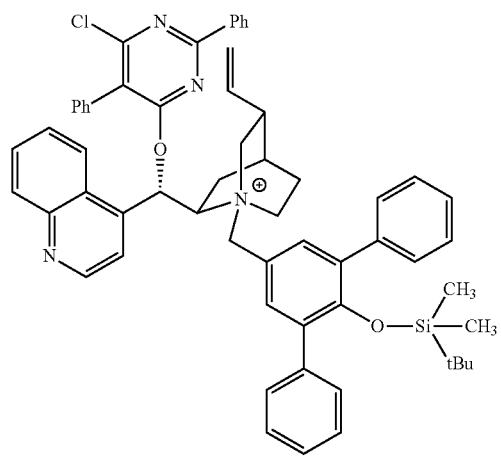

(1S,2R,4S,5R)-1-((2'-((tert-butyldimethylsilyl)oxy)-[1,1':3', 1''-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21b); and

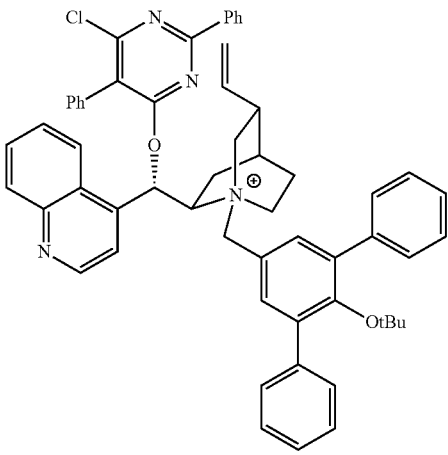 [SMILES: C=CC1C[N+]2(Cc3cc(-c4ccccc4)c(OC)c(-c4ccccc4)c3)CCC1CC2[C@@H](Oc1nc(-c2ccccc2)nc(Cl)c1-c1ccccc1)c1ccnc2ccccc12]

(1S,2R,4S,5R)-1-((2'-(tert-butoxy)-[1,1':3',1''-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21c).

The invention further provides a kit comprising at least one compound of the invention, and instructions for using the at least one compound to catalyze an asymmetric coupling reaction between an imine of formula (II) and a Michael acceptor substrate, and/or to catalyze the enantioselective or diastereoselective isomerization of an imine of formula (II):

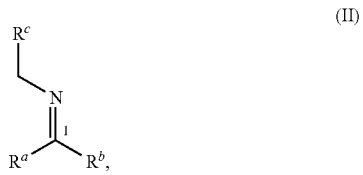

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S-alkyl, —S(aryl), —OSiR$_3$ and —NR$_2$; or
(b) $R^a$ is H, and $R^b$ is selected from the group consisting of optionally substituted aryl, optionally substituted heteroaryl, optionally substituted vinyl, and optionally substituted alkynyl, where each optional substituent is independently selected from the group consisting of alkyl, alkoxy, aryloxy, —S-alkyl, —S(aryl), —OSiR$_3$ and —NR$_2$; and
$R^c$ is selected from the group consisting of optionally substituted alkyl, optionally substituted alkenyl, optionally substituted aryl and optionally substituted heteroaryl, where each optional substituent is independently selected from the group consisting of alkyl, alkoxy, aryloxy, —S-alkyl, —S(aryl), —OSiR$_3$ and —NR$_2$.

The compounds of the present invention may be synthesized using techniques well-known in the art of organic synthesis. The starting materials and intermediates required for the synthesis may be obtained from commercial sources, and/or synthesized according to methods known to those skilled in the art and/or disclosed elsewhere herein.

Methods

The invention provides methods of promoting an asymmetric coupling reaction between an imine and a Michael acceptor substrate.

In certain embodiments, the method comprises contacting the imine, the Michael acceptor substrate and at least one compound of the invention, wherein the imine comprises formula (II):

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S-alkyl, —S(aryl), —OSiR$_3$ and —NR$_2$; or
(b) $R^a$ is H, and $R^b$ is selected from the group consisting of optionally substituted aryl, optionally substituted heteroaryl, optionally substituted vinyl, and optionally substituted alkynyl, where each optional substituent is independently selected from the group consisting of alkyl, alkoxy, aryloxy, —S-alkyl, —S(aryl), —OSiR$_3$ and —NR$_2$; and
$R^c$ is selected from the group consisting of optionally substituted alkyl, optionally substituted alkenyl, optionally substituted aryl and optionally substituted heteroaryl, where each optional substituent is independently selected from the group consisting of alkyl, alkoxy, aryloxy, —S-alkyl, —S(aryl), —OSiR$_3$ and —NR$_2$.

The invention further provides methods of isomerizing an imine. In certain embodiments, the imine comprises formula (II):

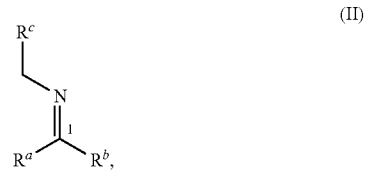

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S-alkyl, —S(aryl), —OSiR$_3$ and —NR$_2$; or (b) $R^a$ is H, and $R^b$ is selected from the group consisting of optionally substituted aryl, optionally substituted heteroaryl, and optionally substituted vinyl, where each optional substituent is independently selected from the group consisting of alkyl, alkoxy, aryloxy, —S-alkyl, —S(aryl), —OSiR$_3$ and —NR$_2$; and $R^c$ is selected from the group consisting of optionally substituted alkyl, optionally substituted alkenyl, optionally substituted aryl and optionally substituted heteroaryl, where each optional substituent is independently selected from the group consisting of alkyl, alkoxy, aryloxy, —S-alkyl, —S(aryl), —OSiR$_3$ and —NR$_2$.

In certain embodiments, the method comprises contacting the imine of formula (II) with at least one compound of the present invention, thus forming a compound of formula (III):

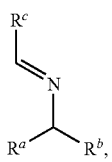

(III)

wherein $R^a$, $R^b$ and $R^c$ are as defined elsewhere herein.

In certain embodiments, the Michael acceptor substrate comprises at least one selected from the group consisting of an optionally substituted α,β-unsaturated aldehyde, an optionally substituted α,β-unsaturated ketone, an optionally substituted enone, an optionally substituted α,β-unsaturated carboxylic acid, an optionally substituted α,β-unsaturated carboxylic ester, an optionally substituted α,β-unsaturated amide, an optionally substituted α,β-unsaturated sulfone, and an optionally substituted α,β-unsaturated sulfoxide. In certain embodiments, a carbon-carbon bond is formed between carbon '1' in (II) and the β-carbon in the Michael acceptor substrate.

In certain embodiments, the imine, the Michael acceptor substrate and the at least one compound are contacted in a system comprising an aqueous phase and a non-aqueous phase, wherein the aqueous and non-aqueous phases are immiscible. In other embodiments, the aqueous phase is basic. In yet other embodiments, the amount of the at least one compound in the system ranges from about 0.001 mol % to about 10 mol % with respect to the imine and/or Michael acceptor substrate.

In certain embodiments, the imine and the at least one compound are contacted in a system comprising an aqueous phase and a non-aqueous phase, wherein the aqueous and non-aqueous phases are immiscible. In other embodiments, the aqueous phase is basic. In yet other embodiments, the amount of the at least one compound in the system ranges from about 0.001 mol % to about 10 mol % with respect to the imine.

In certain embodiments, (III) is formed enantioselectively or diastereoselectively.

In certain embodiments, the at least one compound is selected from the group consisting of: (1S,2R,4S,5R)-1-benzyl-2-((S)-((6-chloro-2,5-diphenylpyrimidin-4-yl)oxy)(quinolin-4-yl)methyl)-5-vinylquinuclidin-1-ium (C-14); (1S,2R,4S,5R)-2-((S)-((6-chloro-2,5-diphenylpyrimidin-4-yl)oxy)(quinolin-4-yl)methyl)-1-(3,5-dimethoxybenzyl)-5-vinylquinuclidin-1-ium (C-16); (1S,2R,4S,5R)-1-([1,1'-biphenyl]-3-ylmethyl)-2-((S)-((6-chloro-2,5-diphenylpyrimidin-4-yl)oxy)(quinolin-4-yl)methyl)-5-vinylquinuclidin-1-ium (C-17); (1S,2R,4S,5R)-1-([1,1':3',1"-terphenyl]-5'-ylmethyl)-2-((S)-((6-chloro-2,5-diphenylpyrimidin-4-yl)oxy)(quinolin-4-yl)methyl)-5-vinylquinuclidin-1-ium (C-18); (1S,2R,4S,5R)-2-((S)-((6-chloro-2,5-diphenylpyrimidin-4-yl)oxy)(quinolin-4-yl)methyl)-1-((4,4"-dimethoxy-[1,1':3',1"-terphenyl]-5'-yl)methyl)-5-vinylquinuclidin-1-ium (C-20); (1S,2R,4S,5R)-2-((S)-((6-chloro-2,5-diphenylpyrimidin-4-yl)oxy)(quinolin-4-yl)methyl)-1-((2'-methoxy-[1,1':3',1"-terphenyl]-5'-yl)methyl)-5-vinylquinuclidin-1-ium (C-21a); (1S,2R,4S,5R)-1-((2'-((tert-butyldimethylsilyl)oxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21b); and (1S,2R,4S,5R)-1-((2'-(tert-butoxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21c).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and methods of the invention, and are not intended to limit the scope of what the inventor(s) regard(s) as the invention.

EXAMPLES

The invention is now described with reference to the following Examples. These Examples are provided for the purpose of illustration only, and the invention is not limited to these Examples, but rather encompasses all variations that are evident as a result of the teachings provided herein.

Unless noted otherwise, the starting materials for the synthesis described herein were obtained from commercial sources or known synthetic procedures and were used without further purification.

Materials and Methods $^1$H and $^{13}$C NMR spectra were recorded on a Varian instrument (400 MHz and 100 MHz, respectively) and internally referenced to tetramethylsilane signal or residual protic solvent signals. Data for $^1$H NMR are recorded as follows: chemical shift (δ, ppm), multiplicity (s, singlet; d, doublet; t, triplet; q, quartet; m, multiplet), integration, coupling constant (Hz). Data for $^{13}$C NMR are reported in terms of chemical shift (δ, ppm).

Infrared spectra were recorded on a Perkin Elmer FT-IR Spectrometer and are reported in frequency of absorption. Low resolution and high resolution mass spectra were recorded on either a Micromass 70-VSE-B instrument (EI, CI) or a Micromass Q-TOF instrument (ESI). Specific rotations were measured on a Jasco Digital Polarimeter. All routine chemicals were purchased and used as received.

High performance liquid chromatography (HPLC) analyses were performed on a Hewlett-Packard 1100 Series instrument equipped with a quaternary pump, using Daicel Chiralcel OJ-H, AD-H or AS-H Columns (250×4.6 mm). UV absorption was monitored at 254 nm, 220 nm or 210 nm.

Example 1: Catalysts

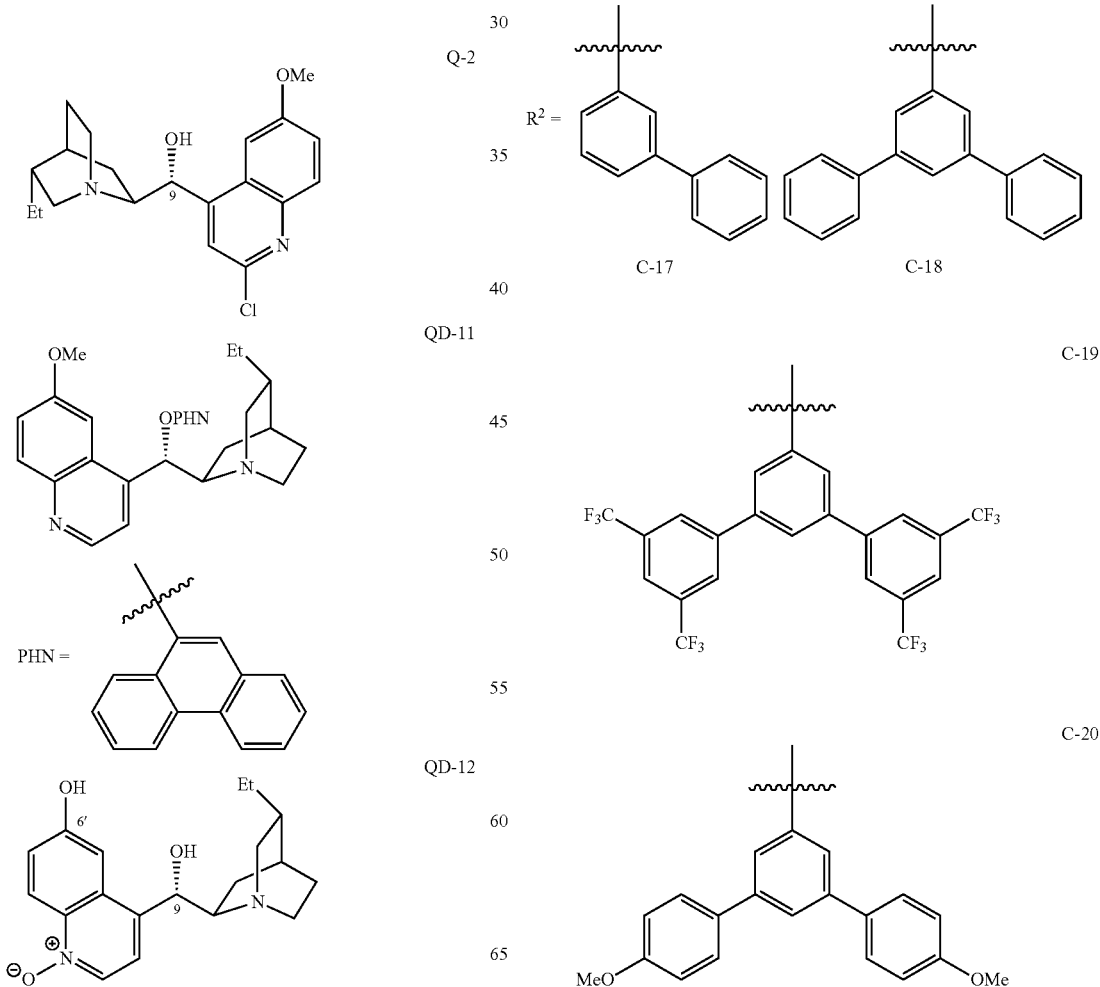

-continued

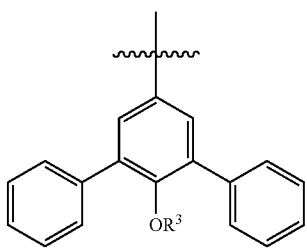

21a, R³ = Me;
21b, R³ = TBS;
21c, R³ = tBu;

Catalysts Q-2 and QD-12 were prepared according to Wu & Deng, 2012, J. Am. Chem. Soc. 134:14334-14337 and Wu, et al., 2011, J. Am. Chem. Soc. 133:12458-12461. Catalyst QD-11 were purchased from Sigma-Aldrich and used as received. Catalyst C-13 was prepared according to Santoro, et al., 2007, Chem. Commun. 5155-5157.

General Procedure for the Preparation of Phase Transfer Catalyst C-14 to C-21c:

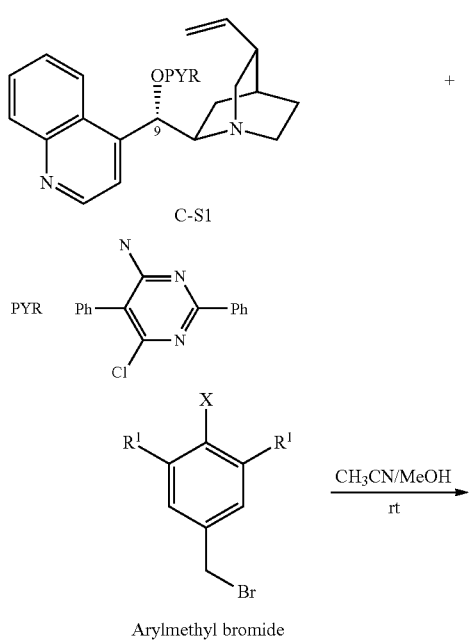

C-14 to C-21c

-continued

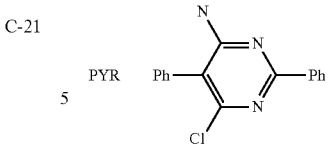

C-21

To the solution of C-S1 (0.1 mmol) in $CH_3CN$/MeOH=4/1 solution (1.0 mL) was added the corresponding arylmethyl bromide (0.1 mmol). The solution was stirred overnight. The solvent was removed under vacuum and the residue was applied to silica column chromatography ($CH_2Cl_2$/MeOH=50/1 to 5/1) to afford the desired phase transfer catalyst.

Tertiary Amine Precursors C-S1 and CD-S1:

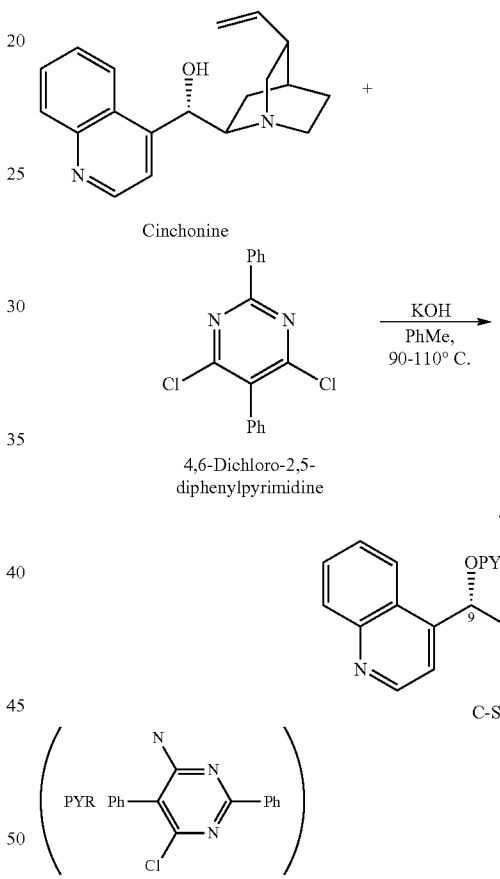

Under $N_2$, to the solution of cinchonine (1.47 g, 5.0 mmol) and 4,6-dichloro-2,5-diphenylpyrimidine (1.51 g, 5.0 mmol) in PhMe (100 mL) was added powdered KOH (4.20 g, 75 mmol) portion wise. The suspension was heated to 90° C. for 10 mins and then refluxed for another 50 mins. Then the resulting mixture was cooled to room temperature and diluted with water (50 mL). The organic layer was separated. Next the aqueous layer was extracted with $CH_2Cl_2$ (50 mL×3). The combined organic extracts were washed with brine (100 mL), dried over $Na_2SO_4$ and concentrated under vacuum. The yellow residue was applied to column ($CH_2Cl_2$/MeOH=100/1 to 10/1) to afford C-S1 as a white solid (2.43 g, 87% yield). $[\alpha]_D^{20}$=−103.8 (c=0.68, $CHCl_3$). ¹H NMR (400 MHz, $CDCl_3$) δ 8.83 (d, J=4.5 Hz, 1H), 8.26

(d, J=8.4 Hz, 1H), 8.13 (d, J=8.4 Hz, 1H), 7.91 (d, J=7.6 Hz, 2H), 7.76 (t, J=7.6 Hz, 1H), 7.63 (t, J=7.6 Hz, 1H), 7.53 (dq, J=14.3, 7.1 Hz, 3H), 7.42 (d, J=6.8 Hz, 2H), 7.33 (dd, J=9.3, 5.9 Hz, 2H), 7.20 (t, J=7.7 Hz, 2H), 7.03 (d, J=5.6 Hz, 1H), 5.42-5.28 (m, 1H), 4.90 (dd, J=27.9, 13.6 Hz, 2H), 3.15 (dd, J=14.9, 9.2 Hz, 1H), 2.83 (d, J=8.9 Hz, 2H), 2.74 (d, J=9.3 Hz, 1H), 2.70-2.57 (m, 1H), 2.12 (dd, J=15.3, 6.9 Hz, 1H), 1.85-1.75 (m, 1H), 1.66 (s, 1H), 1.58 (s, 1H), 1.44 (d, J=8.4 Hz, 2H), 1.31 (dd, J=17.9, 8.9 Hz, 1H). $^{13}$C NMR (100 MHz, CDCl$_3$) δ 166.6, 162.6, 160.2, 150.1, 148.6, 146.2, 140.3, 135.7, 132.1, 131.3, 130.8, 130.1, 129.4, 128.8, 128.7, 128.4, 128.3, 126.9, 126.0, 123.5, 118.9, 118.1, 114.9, 77.8, 60.1, 50.0, 49.9, 40.4, 28.4, 26.3, 22.9. IR (CHCl$_3$) v 2943, 2872, 1569, 1517, 1323, 1103, 992, 909, 845, 758 cm$^{-1}$. HRMS (ESI/[M+H]$^+$) Calcd. for C$_{35}$H$_{32}$N$_4$OCl m/z 559.2265. found m/z 559.2261.

8.17 (d, J=8.3 Hz, 1H), 7.90 (d, J=7.4 Hz, 2H), 7.79 (t, J=7.6 Hz, 1H), 7.68 (t, J=7.6 Hz, 1H), 7.57 (t, J=7.2 Hz, 2H), 7.53-7.44 (m, 3H), 7.35-7.28 (m, 2H), 7.18 (t, J=7.7 Hz, 2H), 7.03 (d, J=3.5 Hz, 1H), 5.72-5.58 (m, 1H), 4.88 (t, J=13.4 Hz, 2H), 3.20-3.12 (m, 1H), 3.12-2.97 (m, 2H), 2.67-2.51 (m, 2H), 2.18 (s, 1H), 1.65 (d, J=2.6 Hz, 1H), 1.54 (dd, J=16.4, 9.5 Hz, 2H), 1.23 (dd, J=15.1, 8.2 Hz, 1H), 1.10-0.94 (m, 1H). $^{13}$C NMR (100 MHz, CDCl$_3$) δ 166.4, 162.7, 150.1, 148.6, 145.8, 141.8, 135.6, 132.1, 131.3, 130.8, 130.1, 129.5, 128.7, 128.7, 128.4, 128.3, 127.1, 125.6, 123.2, 118.9, 117.6, 114.5, 78.2, 59.9, 57.4, 43.4, 39.9, 27.8, 27.2, 22.3; IR (CHCl$_3$) v 2942, 2868, 1568, 1516, 1406, 1288, 1216, 1069, 1019, 993, 844, 756, 699 cm$^{-1}$. HRMS (ESI/[M+H]$^+$) Calcd. for C$_{35}$H$_{32}$N$_4$OCl m/z 559.2265. found m/z 559.2263.

Arylmethyl Bromides:

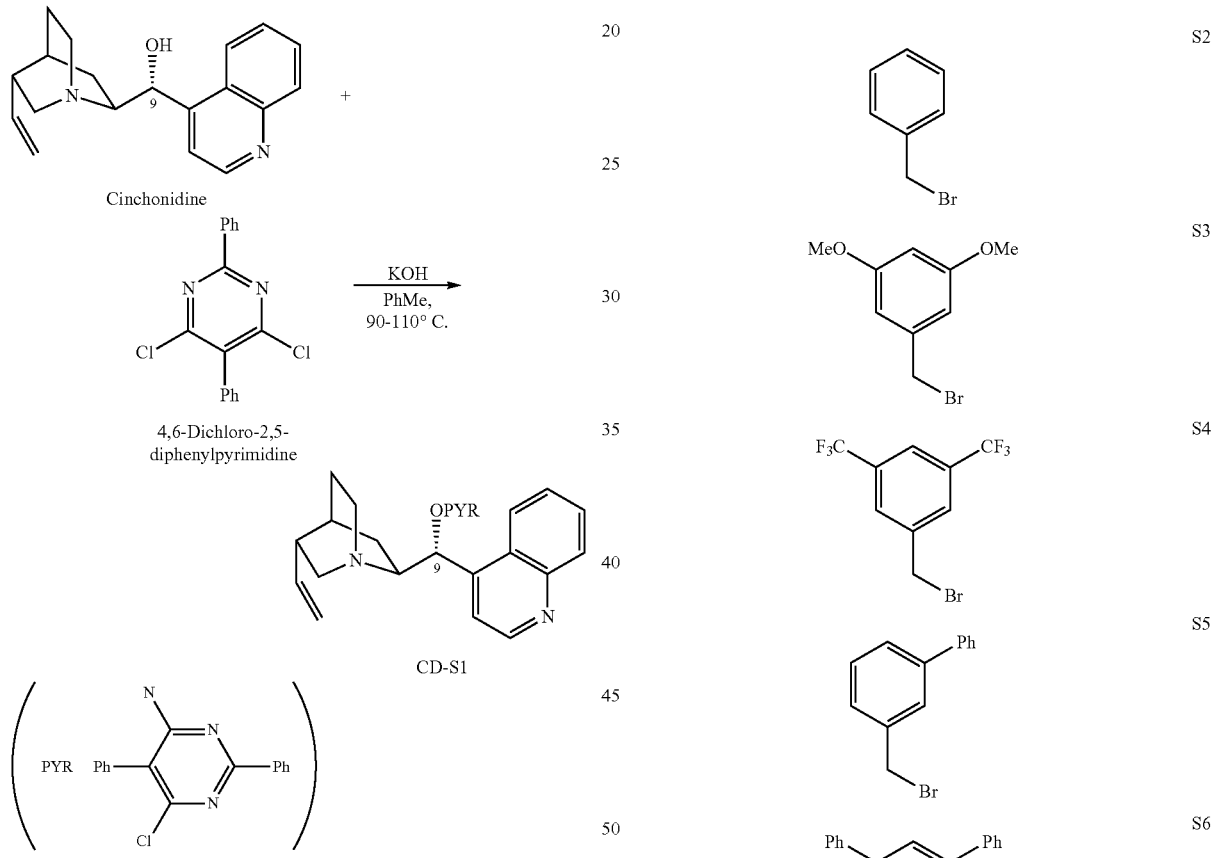

Under N$_2$, to the solution of cinchonidine (294.4 mg, 1.0 mmol) and 4,6-dichloro-2,5-diphenylpyrimidine (301.3 mg, 1.0 mmol) in PhMe (20 mL) was added powdered KOH (840.0 mg, 15 mmol) portionwise. The suspension was heated to 90° C. for 10 mins and then refluxed for another 50 mins. Then the resulting mixture was cooled down to room temperature and diluted with water (10 mL). The organic layer was separated. Next the aqueous layer was extracted with CH$_2$Cl$_2$ (10 mL×3). The combined organic extracts were washed with brine (20 mL), dried over Na$_2$SO$_4$ and concentrated under vacuum. The yellow residue was applied to column (CH$_2$Cl$_2$/MeOH=100/1 to 10/1) to afford CD-S1 as a white solid (462.5 mg, 83% yield). [α]$_D^{20}$=+164.8 (c=0.46, CHCl$_3$). $^1$H NMR (400 MHz, CDCl$_3$) δ 8.84 (d, J=4.5 Hz, 1H), 8.28 (d, J=8.4 Hz, 1H), -continued

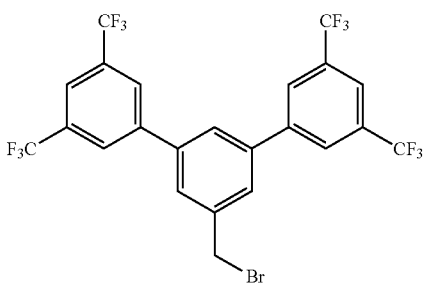

S9
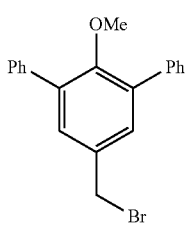

S10
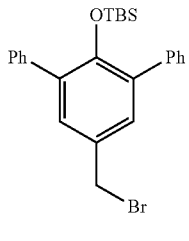

S11
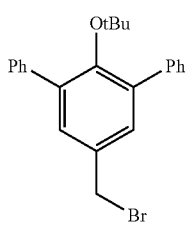

S2-S5 were purchased from Sigma-Aldrich and used as received. S6, S7 and S8 were prepared according to Rajakumar, et al., 2006, Synthesis 528-532; Rajakumar & Srinivasan, 2004, Tetrahedron 60:10285-10291; Furukawa, et al., 2008, Angew. Chem., Int. Ed. 47:8051-8054.

S9 was synthesized according to the following procedure:

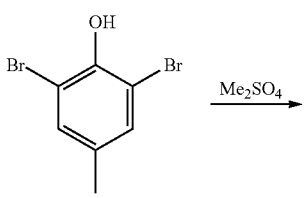

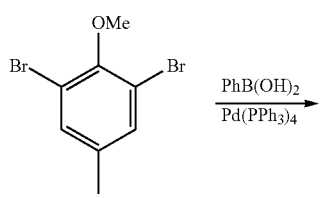

-continued

S8

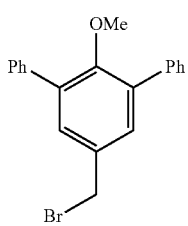

Compound S12 was prepared according to Sevenard, et al., 2008, Synthesis 1867-78.

S13

Under $N_2$, to a round bottom flask charged with S12 (1.68 g, 6.0 mmol), PhB(OH)$_2$ (2.93 g, 24.0 mmol), $K_2CO_3$ (10.0 g, 72.0 mmol) and Pd(PPh$_3$)$_4$ (0.347 g, 0.3 mmol) was added PhMe (75 mL), EtOH (16 mL) and $H_2O$ (32 mL). The mixture was heated at reflux overnight. TLC check showed the completion of the reaction. The organic layer was separated and the aqueous layer was extracted with Hex/EA=3/1 solution (40 mL×3). The organic solvents were combined, washed with $H_2O$ (40 mL×2) and brine (40 mL×2), dried over $Na_2SO_4$ and concentrated under vacuum. The residue was applied to column (Hex/CH$_2$Cl$_2$=50/1 to Hex/CH$_2$Cl$_2$=20/1) to afford the S13 as a white solid (1.51 g, 92% yield). $^1$H NMR (400 MHz, CDCl$_3$) δ 7.63 (d, J=8.1 Hz, 4H), 7.45 (t, J=7.6 Hz, 4H), 7.37 (t, J=7.3 Hz, 2H), 7.19 (s, 2H), 3.17 (s, 3H), 2.42 (s, 3H). $^{13}$C NMR (100 MHz, CDCl$_3$) δ 152.8, 138.9, 135.5, 133.7, 131.0, 129.4, 128.3, 127.2, 60.7, 21.0. IR (CHCl$_3$) ν 3032, 2927, 1676, 1599, 1495, 1470, 1413, 1233, 1171, 1011, 910, 867, 739 cm$^{-1}$. HRMS (ESI/[M+H]$^+$) Calcd. for C$_{20}$H$_{19}$O m/z 275.1436. found m/z 275.1441.

S9

Under $N_2$, to a round bottom flask charged with S13 (412 mg, 1.5 mmol) and N-bromo-succinimide (320 mg, 1.8 mmol) was added CCl$_4$ (10 mL). The mixture was stirred at reflux overnight. After the mixture was cooled to room temperature, the precipitates were filtered off and the solvent was removed under vacuum. Then the residue was applied to silica column chromatography (Hexanes to Hex/Acetone=20/1) to afford S9 as a white solid (349 mg, 66% yield). $^1$H NMR (400 MHz, CDCl$_3$) δ 7.61-7.56 (m, 4H), 7.46-7.39 (m, 4H), 7.38-7.32 (m, 4H), 4.52 (s, 2H), 3.15 (s, 3H). $^{13}$C NMR (100 MHz, CDCl$_3$) δ 155.1, 138.2, 136.2, 133.6, 131.1, 129.3, 128.4, 127.5, 60.6, 33.4. IR (CHCl$_3$) ν 3108, 2375, 1491, 1420, 1222, 1217, 1173, 1051, 1000, 928, 773, 699, 658 cm$^{-1}$. HRMS (EI/[M+H]$^1$) Calcd. for C$_{20}$H$_{17}$OBr m/z 352.0463. found m/z 352.0462.

S10 was synthesized according to the following procedure:

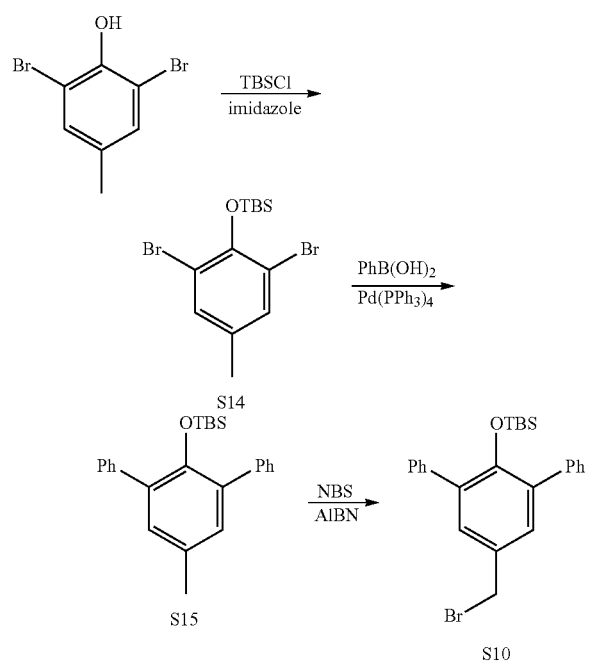

Compound S14 was prepared according to Akai, et al., 2008, Angew. Chem., Int. Ed. 47:7673-7676.

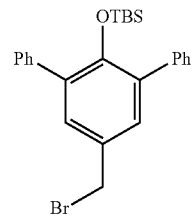

Under N$_2$, to a round bottom flask charged with S14 (1.52 g, 4.0 mmol), PhB(OH)$_2$ (2.93 g, 24.0 mmol), K$_2$CO$_3$ (10.0 g, 72.0 mmol) and Pd(PPh$_3$)$_4$ (0.462 g, 0.4 mmol) was added PhMe (50 mL), EtOH (10 mL) and H$_2$O (20 mL). The mixture was degassed under vacuum at −78° C. for three times. Then it was heated at reflux for 60 h. The organic layer was separated and the aqueous layer was extracted with Hex/EA=3/1 solution (30 mL×3). The organic solvents were combined, washed with H$_2$O (20 mL×2) and brine (30 mL×2), dried over Na$_2$SO$_4$ and concentrated under vacuum. The residue was quickly passed through a pad of silica and washed with Et$_2$O to remove the Palladium black. Then it was recrystallized in EtOH to afford S15 as colorless needles (0.905 g, 60% yield). $^1$H NMR (400 MHz, CDCl$_3$) δ 7.63 (d, J=7.9 Hz, 4H), 7.42 (t, J=7.7 Hz, 4H), 7.37-7.30 (m, 2H), 7.17 (s, 2H), 2.41 (s, 3H), 0.75 (s, 9H), −0.74 (s, 6H). $^{13}$C NMR (100 MHz, CDCl3) δ 147.4, 140.2, 134.7, 131.4, 131.2, 130.4, 128.1, 126.9, 26.3, 20.8, 18.4, −4.7. IR (CHCl$_3$) ν 2954, 2918, 2896, 2857, 1490, 1463, 1422, 1234, 1186, 913, 886, 839, 781, 743, 698 cm$^{-1}$. HRMS (EI/[M+H]$^1$) Calcd. for C$_{25}$H$_{30}$OSi m/z 374.2066. found m/z 374.2062.

Under N$_2$, to a round bottom flask charged with S15 (94.0 mg, 0.25 mmol), N-bromosuccinimide (53.4 mg, 0.3 mmol) and azobisisobutyronitrile (AIBN, 4.1 mg, 0.025 mmol) was added CCl$_4$ (1.0 mL). The mixture was stirred at reflux for 4 h. After the mixture was cooled to room temperature, the precipitates were filtered off and the solvent was removed under vacuum. Then the residue was applied to silica column chromatography (Hexanes to Hex/CH$_2$Cl$_2$=300/1) to afford S10 as a white solid (66.2 mg, 59% yield). $^1$H NMR (400 MHz, CDCl$_3$) δ 7.60-7.53 (m, 4H), 7.39 (dd, J=10.3, 4.7 Hz, 4H), 7.35-7.28 (m, 4H), 4.54 (s, 2H), 0.68 (d, J=2.8 Hz, 9H), −0.79 (s, 6H). $^{13}$C NMR (100 MHz, CDCl$_3$) δ 150.0, 139.4, 135.4, 131.5, 131.3, 130.4, 128.2, 127.2, 33.8, 26.3, 18.4, −4.6. IR (CHCl$_3$) ν 3041, 2951, 2853, 1491, 1462, 1421, 1240, 1211, 1184, 1076, 1028, 926, 886, 780, 697 cm$^{-1}$. HRMS (EI[M+H]$^+$) Calcd. for C$_{25}$H$_{29}$OBrSi m/z 452.1171. found m/z 452.1175.

S11 was synthesized according to the following procedure:

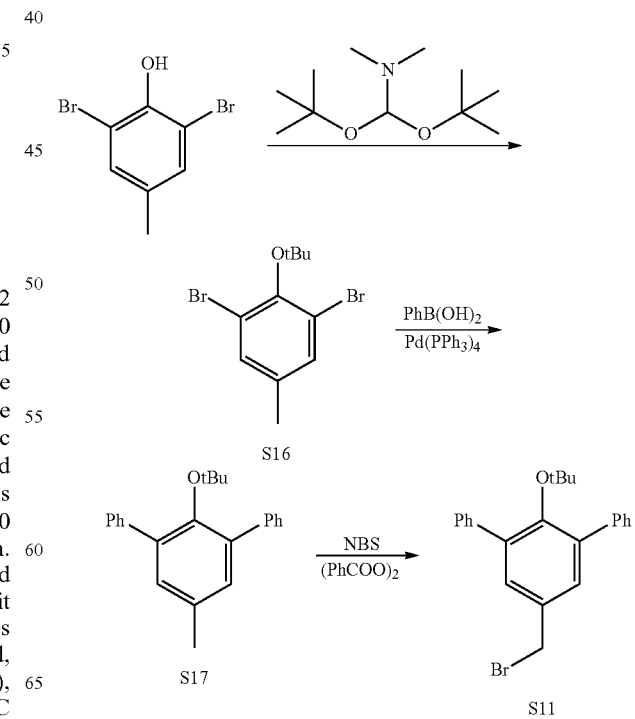

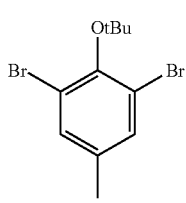

S16

2,6-dibromo-4-methylphenol (2.66 g, 10.0 mmol) and N,N-dimethyl formamide di-tert-butyl acetal (10.2 g, 50.0 mmol) were dissolved in PhMe (50 mL) and the solution was refluxed for three days. The solvent was removed under vacuum and the residue was applied to column (Hexanes) to afford S16 as colorless oil (2.11 g, 66% yield). $^1$H NMR (400 MHz, CDCl$_3$) δ 7.32 (s, 2H), 2.25 (s, 3H), 1.55 (s, 9H). $^{13}$C NMR (100 MHz, CDCl$_3$) δ 149.6, 135.4, 133.3, 120.2, 85.7, 30.2, 20.0. IR (CHCl$_3$) ν 2978, 2931, 2873, 1532, 1451, 1369, 1261, 1156, 858, 736. HRMS (ESI/[M−CH$_3$]$^+$) Calcd. for C$_{10}$H$_{11}$Br$_2$O m/z 304.9177. found m/z 304.9180.

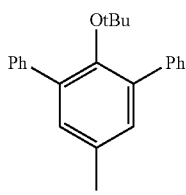

S17

Under N$_2$, to a round bottom flask charged with S16 (1.85 g, 5.7 mmol), PhB(OH)$_2$ (4.20 g, 34.2 mmol), K$_2$CO$_3$ (14.3 g, 102.6 mmol) and Pd(PPh$_3$)$_4$ (1.33 g, 1.1 mmol) was added PhMe (53 mL), EtOH (12 mL) and H$_2$O (24 mL). The mixture was degassed under vacuum at −78° C. for three times. Then it was heated at reflux for 7 days. The organic layer was separated and the aqueous layer was extracted with Hex/EA=3/1 solution (30 mL×3). The organic solvents were combined, washed with H$_2$O (20 mL×2) and brine (30 mL×2), dried over Na$_2$SO$_4$ and concentrated under vacuum. The residue was purified by chromatography (Hexanes/CH$_2$Cl$_2$=20/1) to afford S17 as a white solid (1.44 g, 80% yield). $^1$H NMR (400 MHz, CDCl$_3$) δ 7.59 (d, J=7.1 Hz, 4H), 7.39 (t, J=7.5 Hz, 4H), 7.29 (t, J=7.4 Hz, 2H), 7.12 (s, 2H), 2.38 (s, 3H), 0.57 (s, 9H). $^{13}$C NMR (100 MHz, CDCl3) δ 148.6, 141.1, 138.9, 133.1, 130.6, 130.2, 127.9, 126.7, 81.9, 28.9, 20.8. IR (CHCl$_3$) ν 3032, 2978, 2931, 1462, 1421, 1366, 1233, 1159, 911, 874, 745, 700. HRMS (ESI/[M+H]$^+$) Calcd. for C$_{23}$H$_{25}$O m/z 317.1905. found m/z 317.1902.

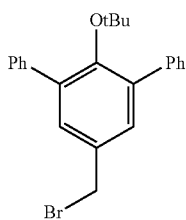

S11

Under N$_2$, to a round bottom flask charged with S17 (885.0 mg, 2.80 mmol), N-bromosuccinimide (548.0 mg, 3.08 mmol), benzoyl peroxide (13.6 mg, 0.056 mmol) and potassium carbonate (16.8 mg, 0.122 mmol) was added CCl$_4$ (14.0 mL). The mixture was stirred at reflux for 3 h. After the mixture was cooled to room temperature, the precipitates were filtered off and the solvent was removed under vacuum. Then the residue was applied to silica column chromatography (Hexanes/Ethyl Acetate=50/1) to afford S11 as a white solid (880.0 mg, 80% yield). $^1$H NMR (400 MHz, CDCl$_3$) δ 7.62-7.57 (m, 4H), 7.40 (t, J=7.5 Hz, 4H), 7.35-7.29 (m, 4H), 4.55 (s, 2H), 0.59 (s, 10H). $^{13}$C NMR (100 MHz, CDCl$_3$) δ 151.2, 140.4, 139.6, 133.1, 130.6, 130.1, 128.0, 127.0, 82.9, 33.4, 28.9. IR (CHCl$_3$) ν 3058, 2977, 2932, 1946, 1800, 1599, 1461, 1419, 1366, 1214, 1154, 907, 876, 732, 697. HRMS (ESI/[M+H-tBu]$^+$) Calcd. for C$_{19}$H$_{15}$BrO m/z 338.0306. found m/z 338.0307.

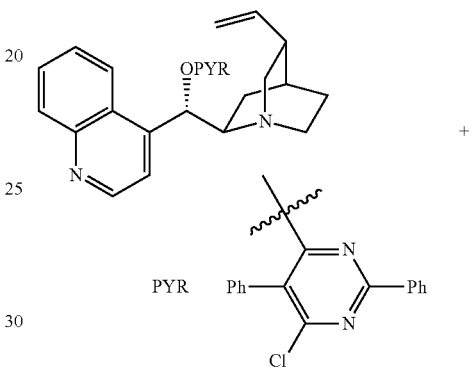

C-S1

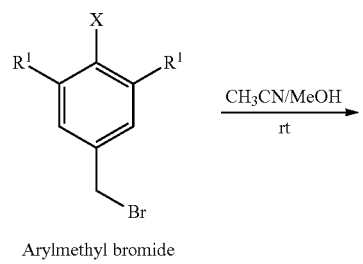

Arylmethyl bromide

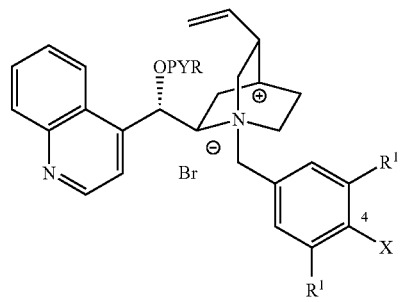

C-14 to C-21c

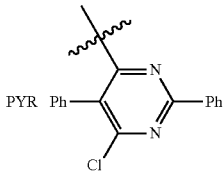

-continued

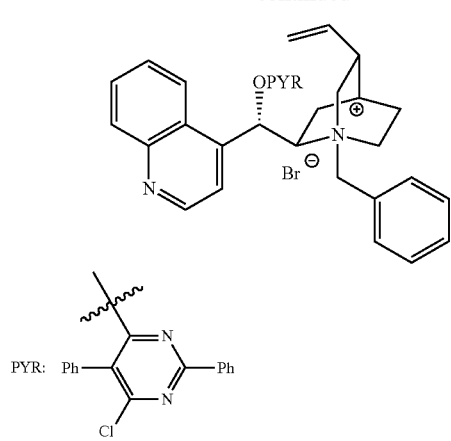

C-14

(1S,2R,4S,5R)-1-benzyl-2-((S)-((6-chloro-2,5-diphenylpyrimidin-4-yl)oxy)(quinolin-4-yl)methyl)-5-vinylquinuclidin-1-ium bromide. Catalyst C-14 was obtained according to the general procedure as a white solid (0.52 mmol scale reaction, 315.1 mg, 83% yield). $[\alpha]_D^{20}$=−94.2 (c=0.55, CHCl$_3$). $^1$H NMR (400 MHz, CDCl$_3$) δ 9.16 (d, J=8.4 Hz, 1H), 8.89 (d, J=4.5 Hz, 1H), 8.14 (t, J=7.3 Hz, 1H), 8.09 (t, J=7.6 Hz, 1H), 7.87 (q, J=9.5 Hz, 2H), 7.85-7.77 (m, 2H), 7.77-7.65 (m, 3H), 7.65-7.52 (m, 3H), 7.49-7.39 (m, 3H), 7.34-7.28 (m, 1H), 7.12 (t, J=7.8 Hz, 2H), 6.43 (d, J=11.7 Hz, 1H), 5.65 (t, J=11.1 Hz, 1H), 5.13-5.00 (m, 2H), 5.00-4.91 (m, 2H), 4.20 (d, J=11.7 Hz, 1H), 3.38 (t, J=11.3 Hz, 1H), 3.12 (dd, J=15.5, 5.9 Hz, 1H), 2.77 (dd, J=21.2, 9.7 Hz, 1H), 2.38-2.15 (m, 2H), 2.00-1.82 (m, 2H), 1.82-1.65 (m, 1H), 1.30 (dt, J=14.9, 7.7 Hz, 1H). $^{13}$C NMR (100 MHz, CDCl$_3$) δ 164.6, 163.2, 161.6, 149.3, 148.5, 139.9, 134.8, 134.4, 134.0, 132.0, 131.9, 130.8, 130.7, 130.1, 129.7, 129.6, 129.4, 129.3, 128.5, 128.3, 126.6, 125.2, 124.6, 119.0, 118.6, 118.5, 72.5, 64.8, 61.7, 56.1, 54.9, 38.4, 27.4, 23.4, 23.1. IR (CHCl$_3$) ν 3051, 2913, 2193, 1574, 1516, 1409, 1352, 1217, 1124, 1003, 923, 844, 754, 703 cm$^{-1}$. HRMS (ESI/[M−Br]$^+$) Calcd. for C$_{42}$H$_{38}$N$_4$OCl, m/z 649.2734. found m/z 649.2733.

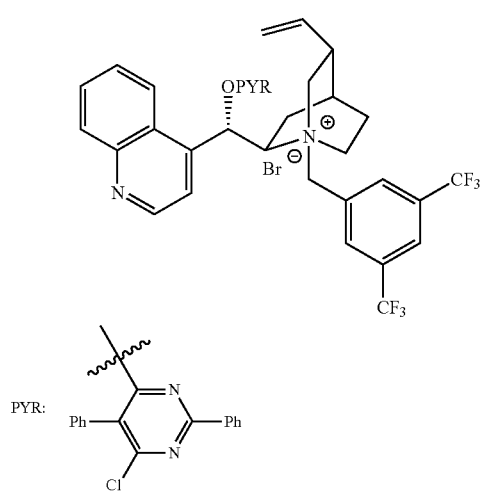

C-15

Catalyst C-15 was obtained as a white solid (0.08 mmol scale reaction, 65.7 mg, 94% yield). $[\alpha]_D^2$=−48.0 (c=0.46, CHCl$_3$). $^1$H NMR (400 MHz, CDCl$_3$) δ 9.27 (d, J=8.2 Hz, 1H), 8.90 (d, J=4.4 Hz, 1H), 8.38 (bs, 2H), 8.18 (d, J=8.3 Hz, 1H), 8.09 (t, J=7.4 Hz, 1H), 8.03 (s, 1H), 7.92 (t, J=7.6 Hz, 1H), 7.79 (s, 1H), 7.76-7.64 (m, 4H), 7.63-7.50 (m, 3H), 7.43 (s, 1H), 7.32 (t, J=7.5 Hz, 1H), 7.15-7.02 (m, 3H), 5.98 (t, J=11.0 Hz, 1H), 5.28 (s, 1H), 5.21-5.09 (m, 2H), 5.06-4.96 (m, 1H), 4.16 (d, J=12.0 Hz, 1H), 3.09 (dt, J=22.7, 11.9 Hz, 2H), 2.61 (dd, J=20.2, 9.5 Hz, 1H), 2.38-2.24 (m, 2H), 2.11-1.91 (m, 2H), 1.80 (t, J=12.7 Hz, 1H), 1.45-1.31 (m, 1H). $^{13}$C NMR (100 MHz, CDCl$_3$) δ 164.6, 163.2, 161.6, 149.3, 148.5, 139.7, 134.4, 134.2, 134.0, 132.8 (q, J$_{C-F}$=34.1 Hz), 132.0, 131.9, 130.7, 130.2, 129.9, 129.6, 129.4, 129.2, 128.4, 128.2, 125.1, 124.8, 124.5, 122.68 (q, J$_{C-F}$=273.6 Hz), 119.4, 118.6, 72.7, 65.4, 59.5, 56.1, 55.3, 38.2, 27.2, 23.2, 23.1. $^{19}$F NMR (376 MHz, CDCl$_3$) δ=−65.7. IR (CHCl$_3$) ν 3020, 2209, 1575, 1516, 1410, 1371, 1279, 1217, 1182, 1143, 907, 771, 729 cm$^{-1}$. HRMS (ESI/[M−Br]$^+$) Calcd. for C$_{44}$H$_{36}$N$_4$OClF$_6$, m/z 785.2482. found m/z 785.2480.

C-16

(1S,2R,4S,5R)-2-((S)-((6-chloro-2,5-diphenylpyrimidin-4-yl)oxy)(quinolin-4-yl)methyl)-1-(3,5-dimethoxybenzyl)-5-vinylquinuclidin-1-ium bromide. Catalyst C-16 was obtained as a white solid (0.08 mmol scale reaction, 54.8 mg, 87% yield). $[\alpha]_D^2$=−46.3 (c=1.09, CHCl$_3$). $^1$H NMR (400 MHz, CDCl$_3$) δ 9.13 (d, J=8.3 Hz, 1H), 8.88 (d, J=4.5 Hz, 1H), 8.18-8.05 (m, 2H), 7.90 (t, J=7.7 Hz, 1H), 7.84 (s, 1H), 7.71 (d, J=7.3 Hz, 4H), 7.64-7.49 (m, 3H), 7.39 (bs, 1H), 7.35-7.29 (m, 1H), 7.12 (t, J=7.8 Hz, 2H), 7.05 (s, 2H), 6.46 (s, 1H), 6.22 (d, J=11.7 Hz, 1H), 5.67 (t, J=10.9 Hz, 1H), 5.09-4.83 (m, 4H), 4.19 (d, J=11.7 Hz, 1H), 3.82 (s, 6H), 3.67-3.52 (m, 1H), 3.12 (t, J=10.6 Hz, 1H), 2.89 (dd, J=21.2, 9.8 Hz, 1H), 2.39-2.16 (m, 2H), 2.00-1.84 (m, 2H), 1.77 (t, J=11.1 Hz, 1H), 1.41-1.27 (m, 1H). $^{13}$C NMR (100 MHz, CDCl$_3$) δ 164.5, 163.2, 161.5, 161.1, 149.2, 148.5, 140.0, 134.9, 134.3, 131.9, 130.8, 130.1, 129.8, 129.6, 129.4, 128.7, 128.5, 128.3, 125.0, 124.6, 119.0, 118.6, 118.4, 111.7, 102.1, 72.3, 65.0, 62.1, 56.7, 56.0, 55.4, 38.6, 27.4, 23.6, 23.0. IR (CHCl$_3$) ν 3008, 2940, 2894, 1597, 1574, 1517, 1411, 1352, 1207, 1156, 1001, 844, 755, 705 cm$^{-1}$. HRMS (ESI/[M−Br]$^+$) Calcd. for C$_{44}$H$_{42}$N$_4$O$_3$Cl, m/z 709.2945. found m/z 709.2941.

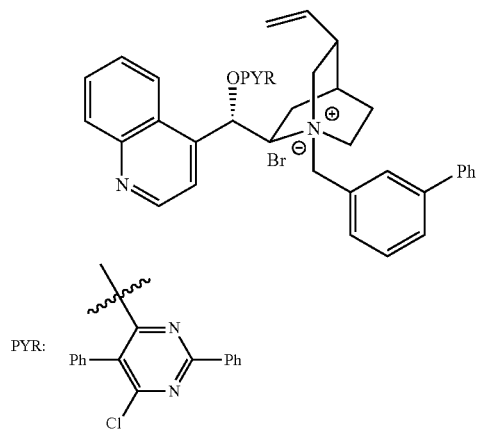

C-17

PYR: [structure]

(1S,2R,4S,5R)-1-([1,1'-biphenyl]-3-ylmethyl)-2-((S)-((6-chloro-2,5-diphenylpyrimidin-4-yl)oxy)(quinolin-4-yl)methyl)-5-vinylquinuclidin-1-ium bromide. Catalyst C-17 was obtained as a white solid (0.08 mmol scale reaction, 50.4 mg, 78% yield). $[\alpha]_D^{20}$=−26.6 (c=1.01, CHCl$_3$). $^1$H NMR (400 MHz, CDCl$_3$) δ 9.15 (d, J=8.4 Hz, 1H), 8.84 (d, J=4.5 Hz, 1H), 8.11 (d, J=8.4 Hz, 1H), 8.06 (t, J=7.6 Hz, 1H), 7.91-7.80 (m, 4H), 7.71-7.56 (m, 6H), 7.56-7.41 (m, 5H), 7.41-7.32 (m, 2H), 7.30-7.25 (m, 1H), 7.07 (t, J=7.7 Hz, 2H), 6.46 (d, J=11.7 Hz, 1H), 5.62 (t, J=11.0 Hz, 1H), 5.12-5.03 (m, 1H), 5.03-4.85 (m, 3H), 4.22 (d, J=11.7 Hz, 1H), 3.36 (t, J=11.3 Hz, 1H), 3.13-2.99 (m, 1H), 2.77 (dd, J=21.2, 9.6 Hz, 1H), 2.31-2.15 (m, 2H), 2.07 (s, 1H), 1.98-1.77 (m, 2H), 1.68 (t, J=9.0 Hz, 1H), 1.33-1.19 (m, 1H). $^{13}$C NMR (100 MHz, CDCl$_3$) δ 164.7, 163.2, 161.6, 149.2, 148.5, 142.1, 140.0, 139.6, 134.8, 134.3, 132.9, 132.2, 132.0, 131.9, 130.7, 130.1, 129.9, 129.7, 129.4, 129.3, 129.2, 129.1, 128.5, 128.3, 128.1, 127.2, 127.1, 125.1, 124.6, 119.0, 118.6, 118.5, 72.7, 64.9, 61.8, 56.2, 55.0, 38.4, 27.4, 23.4, 23.1. IR (CHCl$_3$) ν 3059, 2944, 2893, 2360, 1574, 1517, 1410, 1353, 1216, 1123, 1004, 926, 758, 704 cm$^{-1}$. HRMS (ESI/[M−Br]$^+$) Calcd. for C$_{48}$H$_{42}$N$_4$OCl, m/z 725.3047. found m/z 725.3048.

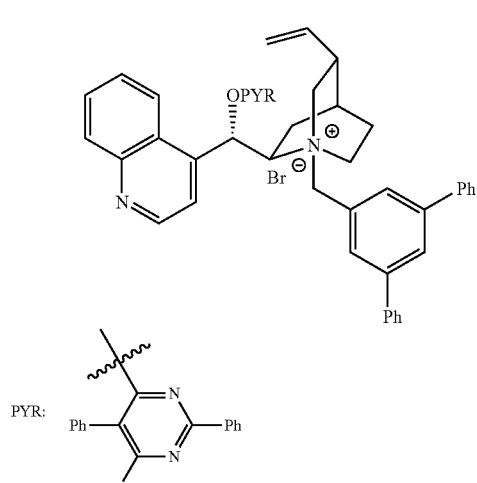

C-18

PYR: [structure]

(1S,2R,4S,5R)-1-([1,1'-biphenyl]-3-ylmethyl)-2-((S)-((6-chloro-2,5-diphenylpyrimidin-4-yl)oxy)(quinolin-4-yl)methyl)-5-vinylquinuclidin-1-ium bromide. Catalyst C-18 was obtained as a white solid (0.08 mmol scale reaction, 67.0 mg, 93% yield). $[\alpha]_D^{20}$=+14.2 (c=0.59, CHCl$_3$). $^1$H NMR (400 MHz, CDCl$_3$) δ 9.23 (d, J=8.4 Hz, 1H), 8.89 (d, J=4.4 Hz, 1H), 8.20-8.07 (m, 2H), 8.00 (s, 2H), 7.93-7.83 (m, 3H), 7.74-7.59 (m, 7H), 7.59-7.49 (m, 3H), 7.45 (t, J=7.5 Hz, 4H), 7.40-7.32 (m, 2H), 7.32-7.25 (m, 2H), 7.09 (t, J=7.6 Hz, 2H), 6.56 (d, J=11.7 Hz, 1H), 5.74 (t, J=10.6 Hz, 1H), 5.17-4.86 (m, 4H), 4.32 (d, J=11.7 Hz, 1H), 3.44 (t, J=11.3 Hz, 1H), 3.17-3.02 (m, 1H), 2.89 (dd, J=20.6, 9.8 Hz, 1H), 2.40-2.17 (m, 2H), 1.96-1.79 (m, 2H), 1.74 (t, J=9.9 Hz, 1H), 1.32-1.17 (m, 1H). $^{13}$C NMR (100 MHz, CDCl$_3$) δ 164.6, 163.2, 161.5, 149.2, 148.5, 142.7, 140.0, 139.5, 134.8, 134.3, 131.9, 131.8, 131.1, 130.6, 130.1, 129.7, 129.6, 129.3, 129.2, 129.1, 128.4, 128.3, 128.1, 128.1, 127.7, 127.2, 125.2, 124.6, 118.9, 118.6, 118.5, 72.7, 64.9, 61.7, 56.3, 55.0, 38.2, 27.3, 23.3, 23.0. IR (CHCl$_3$) ν 3052, 3952, 1573, 1515, 1461, 1410, 1353, 1280, 1174, 1005, 844, 755, 700 cm$^{-1}$. HRMS (ESI/[M−Br]$^+$) Calcd. for C$_{54}$H$_{46}$N$_4$OCl, m/z 801.3360. found m/z 801.3355.

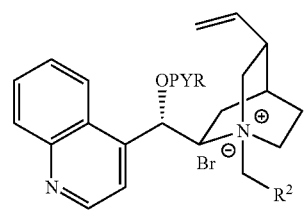

C-19

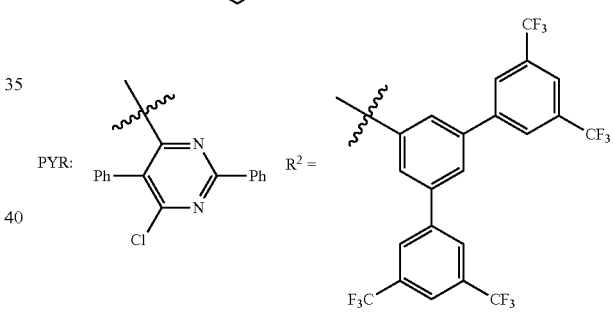

PYR: [structure]   R$^2$ = [structure]

Catalyst C-19 was obtained as a white solid (0.08 mmol scale reaction, 72.1 mg, 78% yield). $[\alpha]_D^{20}$=−6.0 (c=0.48, CHCl$_3$). $^1$H NMR (400 MHz, CDCl$_3$) δ 9.28 (d, J=8.4 Hz, 1H), 8.88 (d, J=4.5 Hz, 1H), 8.36 (bs, 2H), 8.21-8.08 (m, 6H), 7.96 (s, 2H), 7.94-7.86 (m, 3H), 7.67 (dd, J=9.7, 8.6 Hz, 2H), 7.58 (dd, J=13.9, 6.8 Hz, 4H), 7.39 (d, J=4.0 Hz, 1H), 7.32-7.25 (m, 1H), 7.08 (t, J=7.8 Hz, 2H), 6.85 (d, J=11.8 Hz, 1H), 5.89 (t, J=10.9 Hz, 1H), 5.19-4.94 (m, 4H), 4.31 (d, J=11.8 Hz, 1H), 3.41 (t, J=11.2 Hz, 1H), 3.21 (t, J=9.8 Hz, 1H), 2.78 (dd, J=21.1, 9.6 Hz, 1H), 2.44-2.24 (m, 2H), 2.11 (s, 1H), 2.03-1.87 (m, 2H), 1.76 (s, 1H), 1.46-1.31 (m, 1H). $^{13}$C NMR (100 MHz, CDCl$_3$) δ 164.6, 163.3, 161.7, 149.2, 148.5, 141.2, 140.7, 139.7, 134.6, 134.2, 133.0, 132.8 (q, $J_{C-F}$=33.6 Hz), 132.1, 131.9, 130.8, 130.2, 129.8, 129.4, 129.4, 129.3, 128.5, 128.3, 128.3, 127.6, 127.6, 127.3, 125.1, 124.5, 123.2 (q, $J_{C-F}$=276.9 Hz), 122.3, 119.3, 118.6, 118.4, 72.5, 65.4, 60.6, 56.4, 55.5, 38.4, 27.4, 23.4, 23.1. $^{19}$F NMR (376 MHz, CDCl$_3$) δ=−65.7. IR (CHCl$_3$) ν 3011, 1573, 1517, 1410, 1370, 1279, 1173, 1133, 1007, 900, 845, 754, 702 cm$^{-1}$. HRMS (ESI/[M−Br]$^+$) Calcd. for C$_{58}$H$_{42}$N$_4$OClF$_{12}$, m/z 1073.2856. found m/z 1073.2839.

C-20

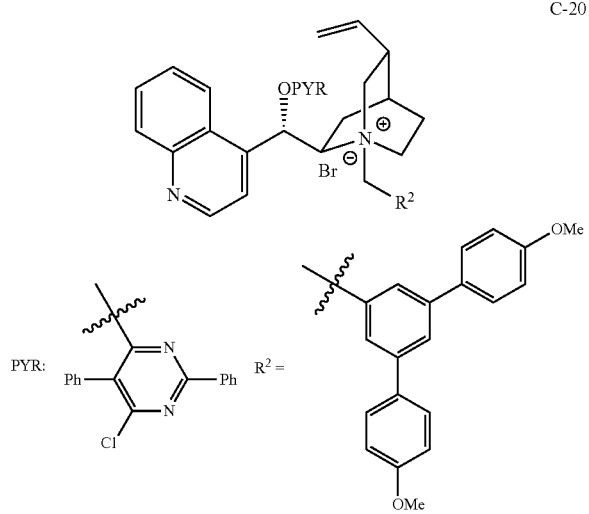

(1S,2R,4S,5R)-2-((S)-((6-chloro-2,5-diphenylpyrimidin-4-yl)oxy)(quinolin-4-yl)methyl)-1-((4,4"-dimethoxy-[1,1':3',1"-terphenyl]-5'-yl)methyl)-5-vinylquinuclidin-1-ium bromide. Catalyst C-20 was obtained as a white solid (0.08 mmol scale reaction, 66.6 mg, 87% yield). $[α]_D^{20}$=+15.6 (c=0.73, CHCl$_3$). $^1$H NMR (400 MHz, CDCl$_3$) δ 9.23 (d, J=7.9 Hz, 1H), 8.89 (d, J=4.1 Hz, 1H), 8.19-8.07 (m, 2H), 7.98-7.83 (m, 3H), 7.80 (s, 1H), 7.73-7.50 (m, 10H), 7.42 (s, 1H), 7.33-7.23 (m, 2H), 7.09 (t, J=7.6 Hz, 2H), 7.06-6.96 (m, 4H), 6.52 (d, J=11.7 Hz, 1H), 5.76 (t, J=10.7 Hz, 1H), 5.18-5.08 (m, 1H), 5.08-4.89 (m, 3H), 4.32 (d, J=11.6 Hz, 1H), 3.85 (s, 6H), 3.47 (t, J=11.2 Hz, 1H), 3.14-3.05 (m, 1H), 2.91 (dd, J=20.1, 9.8 Hz, 1H), 2.35-2.20 (m, 2H), 1.98-1.86 (m, 2H), 1.73 (s, 1H), 1.38-1.28 (m, 1H), 1.24 (td, J=7.1, 2.0 Hz, 1H). $^{13}$C NMR (100 MHz, CDCl$_3$) δ 164.6, 163.2, 161.5, 159.7, 149.2, 148.4, 142.2, 140.0, 134.9, 134.3, 132.0, 131.9, 130.7, 130.1, 130.0, 129.7, 129.4, 129.3, 128.4, 128.3, 127.5, 126.9, 125.2, 124.5, 118.9, 118.6, 118.5, 114.5, 77.4, 72.7, 64.9, 61.9, 56.3, 55.4, 55.0, 38.4, 27.4, 23.4, 23.1. IR (CHCl$_3$) ν 2932, 2837, 1608, 1574, 1514, 1458, 1410, 1352, 1286, 1240, 1180, 1033, 1005, 927, 829, 751 cm$^{-1}$. HRMS (ESI/[M−Br]$^+$) Calcd. for C$_{56}$H$_{50}$N$_4$O$_3$Cl, m/z 861.3571. found m/z 861.3566.

C-21a

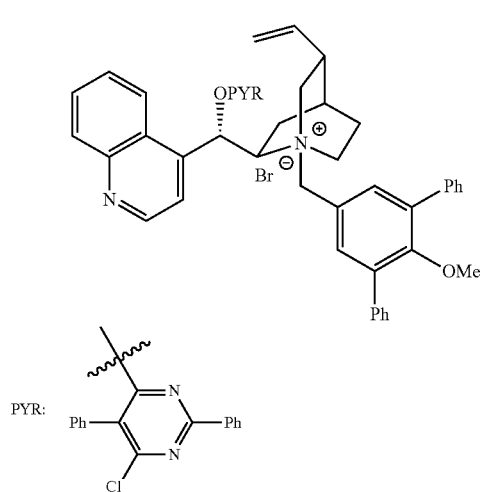

(1S,2R,4S,5R)-2-((S)-((6-chloro-2,5-diphenyl pyrimidin-4-yl)oxy)(quinolin-4-yl)methyl)-1-((2'-methoxy-[1,1':3',1"-terphenyl]-5'-yl)methyl)-5-vinylquinuclidin-1-ium bromide. Catalyst C-21a was obtained as a white solid (0.25 mmol scale reaction, 206.5 mg, 89% yield). $[α]_D^{20}$=−12.3 (c=0.44, CHCl$_3$). $^1$H NMR (400 MHz, CDCl$_3$) δ 9.23 (d, J=8.6 Hz, 1H), 8.89 (d, J=4.5 Hz, 1H), 8.16 (d, J=8.4 Hz, 1H), 8.09 (t, J=7.4 Hz, 1H), 7.93-7.85 (m, 2H), 7.76 (d, J=7.5 Hz, 4H), 7.64 (d, J=7.2 Hz, 4H), 7.48 (t, J=7.4 Hz, 8H), 7.45-7.37 (m, 3H), 7.34 (t, J=7.4 Hz, 1H), 7.15 (t, J=7.8 Hz, 2H), 6.63 (d, J=12.0 Hz, 1H), 5.76 (t, J=11.1 Hz, 1H), 5.20 (s, 1H), 5.14-5.03 (m, 2H), 5.00-4.90 (m, 1H), 4.21 (d, J=11.8 Hz, 1H), 3.34 (t, J=11.4 Hz, 1H), 3.16 (s, 3H), 3.04 (t, J=10.8 Hz, 1H), 2.91 (dd, J=21.2, 9.2 Hz, 1H), 2.27 (dd, J=28.8, 15.8 Hz, 2H), 2.04-1.87 (m, 2H), 1.76 (s, 1H), 1.39-1.23 (m, 2H). $^{13}$C NMR (100 MHz, CDCl$_3$) δ 164.8, 163.4, 161.7, 157.0, 149.3, 148.6, 140.1, 137.3, 136.8, 135.7, 135.0, 134.4, 132.2, 132.0, 130.8, 130.2, 129.7, 129.5, 129.4, 129.3, 128.6, 128.4, 128.0, 125.4, 124.7, 122.4, 119.0, 118.7, 72.9, 64.8, 61.3, 60.6, 56.1, 54.8, 38.4, 27.5, 23.5, 23.2. IR (CHCl$_3$) ν 3062, 1571, 1514, 1469, 1411, 1352, 1287, 1239, 1172, 1002, 926, 775, 749, 700 cm$^{-1}$. HRMS (ESI/[M−Br]$^+$) Calcd. for C$_{55}$H$_{48}$N$_4$O$_2$Cl, m/z 831.3466. found m/z 831.3457.

C-21b

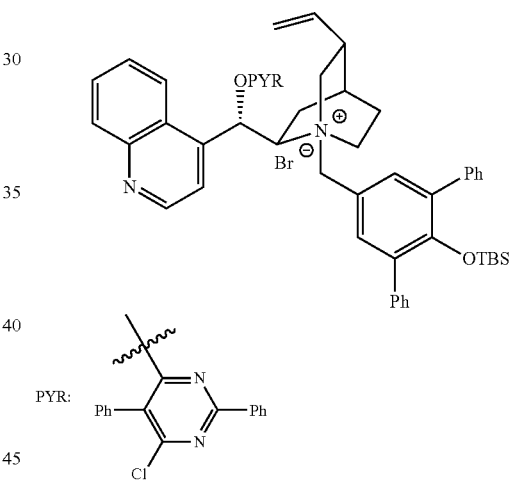

(1S,2R,4S,5R)-1-((2'-((tert-butyldimethylsilyl)oxy)-[1,1':3',1"-terphenyl]-5'-yl)methyl)-2-((S)-((6-chloro-2,5-diphenylpyrimidin-4-yl)oxy) (quinolin-4-yl)methyl)-5-vinylquinuclidin-1-ium bromide. Catalyst C-21b was obtained as a white solid (0.12 mmol scale reaction, 79.3 mg, 73% yield). $[α]_D^{20}$=+5.9 (c=0.46, CHCl$_3$). $^1$H NMR (400 MHz, CDCl$_3$) δ 9.19 (t, J=12.8 Hz, 1H), 8.88 (d, J=4.5 Hz, 1H), 8.15 (d, J=8.4 Hz, 1H), 8.12-8.03 (m, 1H), 7.93-7.82 (m, 2H), 7.77 (d, J=7.5 Hz, 2H), 7.69 (s, 2H), 7.59 (t, J=13.4 Hz, 5H), 7.48 (s, 4H), 7.41 (t, J=7.5 Hz, 6H), 7.33 (q, J=7.2 Hz, 4H), 7.16 (t, J=7.8 Hz, 2H), 6.53 (d, J=11.8 Hz, 1H), 5.75-5.55 (m, 1H), 5.17-4.99 (m, 3H), 4.99-4.82 (m, 1H), 4.24 (d, J=11.8 Hz, 1H), 3.40-3.26 (m, 1H), 3.03-2.81 (m, 2H), 2.38-2.13 (m, 2H), 1.93-1.64 (m, 3H), 1.31-1.14 (m, 1H), 0.67 (s, 11H), −0.81 (s, 3H), −0.82 (s, 3H). $^{13}$C NMR (100 MHz, CDCl$_3$) δ 164.8, 163.2, 161.6, 152.0, 149.2, 148.5, 140.0, 138.4, 135.9, 135.6, 134.9, 134.3, 132.0, 131.8, 130.7, 130.2, 130.1, 129.6, 129.4, 129.3, 128.5, 128.4, 127.6, 125.3, 124.6, 120.0, 118.8, 118.7, 72.9, 64.7, 61.2, 55.9, 54.6, 38.2, 27.3, 26.1, 23.3, 23.0, 18.3, −4.8. IR (CHCl₃) v 2950, 2904, 1575, 1515, 1463, 1411, 1362, 1249, 1215, 1005, 925, 893, 841, 750, 702 cm⁻¹. HRMS (ESI/[M−Br]⁺) Calcd. for C₆₀H₆₀N₄O₂ClSi, m/z 931.4174. found m/z 931.4161.

CD-21b

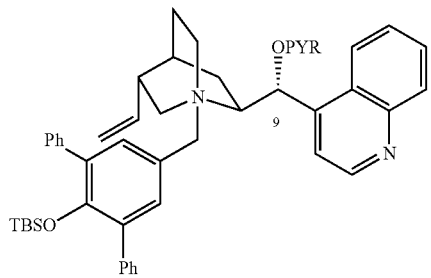

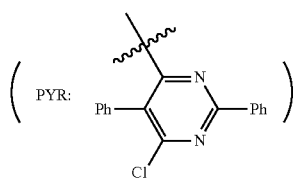

Catalyst CD-21b was obtained as a white solid (0.10 mmol scale reaction, 76.8 mg, 76% yield). [α]$_D^{20}$=−38.8 (c=0.57, CHCl₃). ¹H NMR (400 MHz, CDCl₃) δ 9.05 (d, J=8.5 Hz, 1H), 8.84 (d, J=4.5 Hz, 1H), 8.15 (d, J=8.5 Hz, 1H), 8.06 (t, J=7.7 Hz, 1H), 7.93-7.84 (m, 1H), 7.78 (d, J=7.2 Hz, 3H), 7.64 (bs, 2H), 7.56 (d, J=7.9 Hz, 4H), 7.53-7.29 (m, 12H), 7.17 (t, J=7.7 Hz, 2H), 6.77 (d, J=11.9 Hz, 1H), 5.72 (ddd, J=17.1, 10.5, 6.5 Hz, 1H), 5.29 (d, J=17.2 Hz, 1H), 5.18 (d, J=11.1 Hz, 1H), 5.05 (t, J=9.3 Hz, 1H), 4.99 (d, J=10.5 Hz, 1H), 4.34 (d, J=11.8 Hz, 1H), 3.42-3.25 (m, 1H), 3.04 (t, J=8.0 Hz, 2H), 2.53 (bs, 1H), 2.13-1.87 (m, 2H), 1.68-1.46 (m, 2H), 1.41-1.29 (m, 1H), 0.66 (s, 9H), −0.84 (s, 6H). ¹³C NMR (100 MHz, CDCl₃) δ 165.0, 163.3, 161.1, 152.0, 149.2, 148.5, 140.0, 138.5, 136.0, 135.9, 135.7, 134.4, 132.2, 131.7, 130.9, 130.2, 130.2, 129.8, 129.6, 129.5, 129.3, 128.7, 128.5, 128.4, 127.6, 124.9, 124.4, 120.2, 119.0, 118.7, 118.7, 72.5, 65.0, 62.1, 59.9, 50.8, 37.8, 27.1, 26.2, 25.3, 23.7, 18.3, −4.6, −4.7. IR (CHCl₃) v 2856, 1570, 1514, 1460, 1409, 1348, 1246, 1190, 1129, 989, 891, 840, 748, 777, 700 cm⁻¹. HRMS (ESI/[M−Br]⁺) Calcd. for C₆₀H₆₀N₄O₂ClSi, m/z 931.4174. found m/z 931.4164.

C-21c

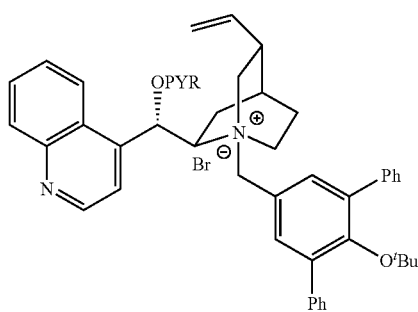

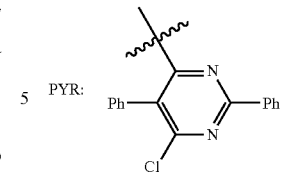

(1S,2R,4S,5R)-1-((2'-(tert-butoxy)-[1,1':3',1''-terphenyl]-5'-yl)methyl)-2-((S)-((6-chloro-2,5-diphenylpyrimidin-4-yl)oxy)(quinolin-4-yl)methyl)-5-vinylquinuclidin-1-ium. Catalyst C-21c was obtained as a white solid (0.12 mmol scale reaction, 67.4 mg, 65% yield). [α]$_D^{20}$=+8.1 (c=0.95, CHCl₃). ¹H NMR (400 MHz, CDCl₃) δ 9.23 (d, J=8.4 Hz, 1H), 8.88 (d, J=4.5 Hz, 1H), 8.15 (d, J=8.5 Hz, 1H), 8.10 (t, J=7.6 Hz, 1H), 7.89 (dd, J=9.5, 5.2 Hz, 2H), 7.78 (d, J=7.2 Hz, 2H), 7.65 (d, J=7.3 Hz, 4H), 7.58-7.30 (m, 13H), 7.17 (t, J=7.8 Hz, 2H), 6.63 (d, J=11.8 Hz, 1H), 5.71 (t, J=11.1 Hz, 1H), 5.22-4.99 (m, 3H), 4.92 (dt, J 5.4, 3.9 Hz, 1H), 4.27 (d, J=11.8 Hz, 1H), 3.34 (t, J=11.3 Hz, 1H), 2.95 (dt, J=29.1, 10.7 Hz, 2H), 2.28 (dt, J=24.7, 10.7 Hz, 2H), 1.91 (dt, J=8.4, 7.9 Hz, 2H), 1.80-1.71 (m, 1H), 1.41-1.20 (m, 1H), 0.57 (s, 9H). ¹³C NMR (100 MHz, CDCl₃) δ 164.6, 163.0, 161.4, 153.3, 149.1, 148.2, 140.1, 139.9, 139.3, 134.9, 134.7, 134.1, 131.9, 131.5, 130.5, 130.0, 129.9, 129.5, 129.4, 129.2, 129.1, 128.4, 128.1, 127.4, 125.1, 124.4, 121.6, 118.7, 118.6, 118.5, 5, 83.9, 64.6, 60.9, 60.2, 55.8, 54.5, 37.9, 28.8, 27.1, 23.1, 22.8, 20.9, 14.0. IR (CHCl₃) v 3059, 2973, 2945, 1575, 1516, 1413, 1362, 1242, 1155, 1001, 754, 703. HRMS (ESI/[M−Br]⁺) Calcd. for C₅₈H₅₄ClN₄O₂ m/z 873.3935. found m/z 873.3909.

CD-21c

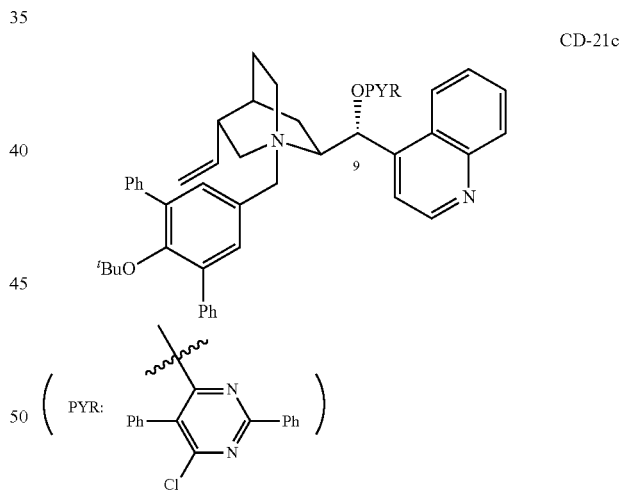

Catalyst CD-21c was obtained as a white solid (1.6 mmol scale reaction, 822.1 mg, 54% yield). [α]$_D^{20}$=−40.6 (c=0.78, CHCl₃). ¹H NMR (400 MHz, CDCl₃) δ 9.08 (d, J=8.5 Hz, 1H), 8.85 (d, J=4.5 Hz, 1H), 8.16 (d, J=8.4 Hz, 1H), 8.09 (t, J=7.6 Hz, 1H), 7.90 (t, J=7.7 Hz, 1H), 7.85-7.74 (m, 3H), 7.61 (d, J=7.4 Hz, 4H), 7.57-7.29 (m, 13H), 7.18 (t, J=7.8 Hz, 2H), 6.85 (d, J=11.8 Hz, 1H), 5.73 (ddd, J=17.1, 10.5, 6.5 Hz, 1H), 5.39-5.18 (m, 2H), 5.09 (t, J 9.2 Hz, 1H), 5.01 (d, J=10.5 Hz, 1H), 4.37 (d, J=11.8 Hz, 1H), 3.42-3.24 (m, 1H), 3.04 (d, J=9.6, 5.8 Hz, 2H), 2.62-2.44 (m, 1H), 1.99 (dd, J=14.7, 4.3 Hz, 2H), 1.75-1.60 (m, 1H), 1.54 (d, J=9.8 Hz, 1H), 1.46-1.31 (m, 1H), 0.56 (s, 9H). ¹³C NMR (100 MHz, CDCl₃) δ 164.7, 163.0, 160.8, 153.2, 149.0, 148.2, 140.0, 139.7, 139.4, 135.8, 135.0, 134.2, 130.4, 129.9, 129.5, 129.3, 129.2, 129.1, 128.4, 128.1, 127.3, 124.6, 124.2, 121.7, 118.6, 118.5, 83.8, 72.3, 64.8, 61.6, 59.7, 50.6, 37.4, 28.8, 26.7, 24.9, 23.4. IR (CHCl$_3$) v 3035, 2974, 2935, 2900, 1574, 1515, 1410, 1362, 1241, 1154, 995, 752, 703. HRMS (ESI/[M−Br]$^+$) Calcd. for C$_{58}$H$_{54}$ClN$_4$O$_2$ m/z 873.3935. found m/z 873.3909.

Example 2: Trifluoromethyl Imines

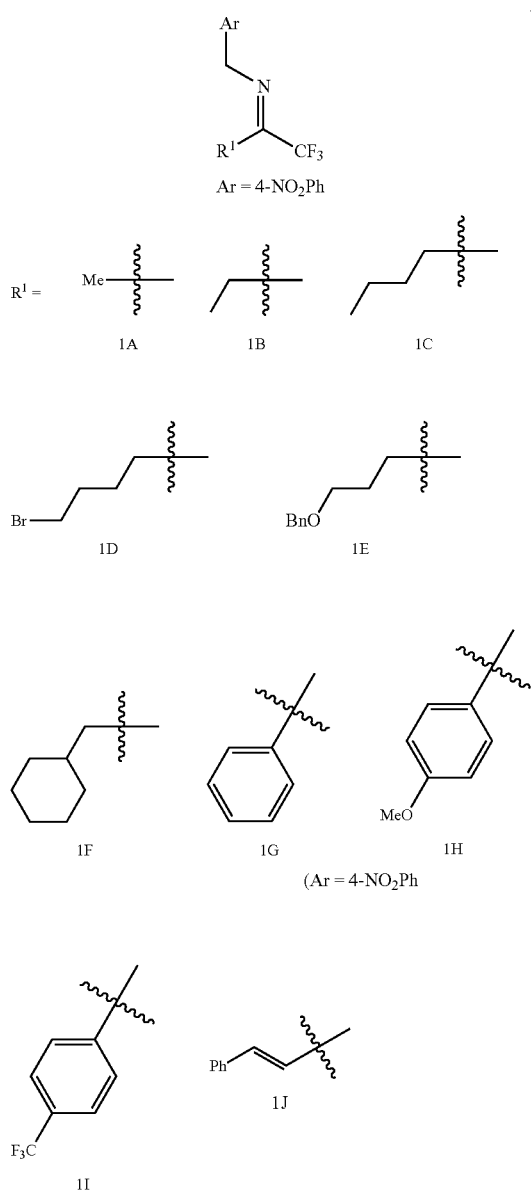

Large Scale Preparation of Methyl Trifluoromethyl Imine 1A:

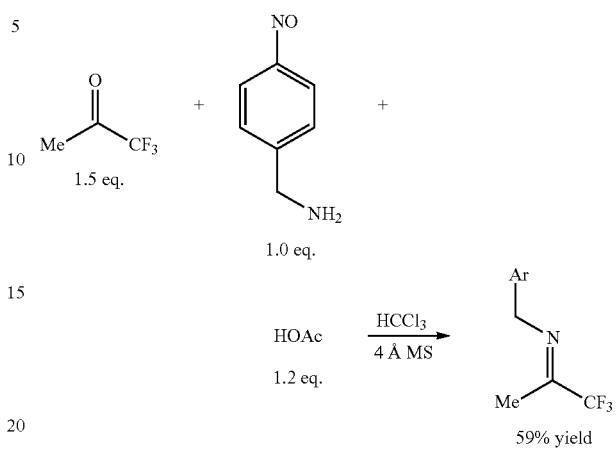

Under N$_2$, to a flask charged with 4-NO$_2$PhCH$_2$NH$_2$ (3.52 g, 23.0 mmol) and 4 Å MS (6.0 g) was added CHCl$_3$ (40 mL). At 0° C., trifluoroacetone (3.10 mL, 34.5 mmol) was added in one portion. Then the suspension was stirred at room temperature for 20 mins. Then the mixture was cooled to 0° C. and HOAc (1.62 mL, 28.0 mmol) was added dropwise. Next the white suspension was moved to a 70° C. oil bath and refluxed for 3 h. After the suspension was cooled to room temperature, hexanes (50 mL) was added. The suspension was filtered through a pad of deactivated silica (5 cm thick) and washed with Hex/Et$_2$O=3/1 solution (200 mL). The filtrate was collected, the solvent was removed and the residue was applied to deactivated silica column chromatography (Hex/CH$_2$Cl$_2$=100/1 to Hex/CH$_2$Cl$_2$=10/1) to afford imine 1A as a white solid (3.17 g, 59% yield).

Alkyl Trifluoromethyl Imines 1B-1F:

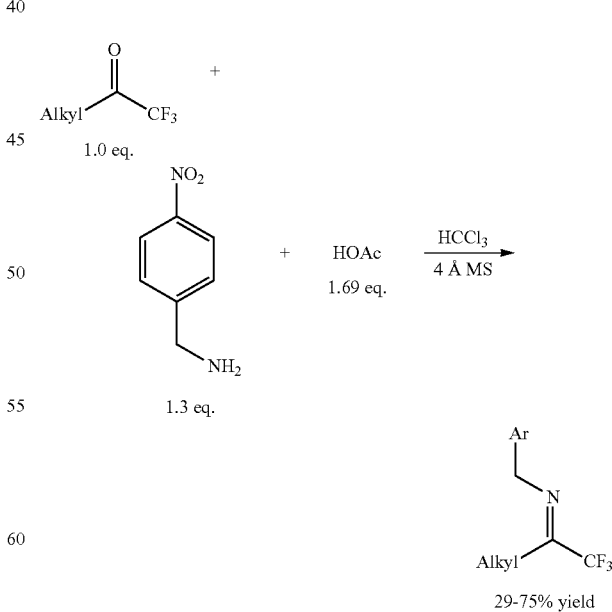

Preparation of Deactivated Silica

The dry silica was packed in a column and washed with MeOH/Et$_3$N=5/1 solution [2 column volume (CV)], followed by MeOH (5 CV or until pH paper test showed the solution was neutral) and Et$_2$O (2 CV). Then the silica was blown dry with compressed air.

Under N$_2$, to a flask charged with 4-NO$_2$PhCH$_2$NH$_2$ (2.00 g, 13.0 mmol) and 4 Å MS (3.0 g) was added CHCl$_3$ (20 mL). The corresponding trifluoromethyl ketone (10.0 mmol)

was then added in one portion. The suspension was stirred at room temperature for 20 mins. HOAc (16.0 mmol) was added dropwise. Next the white suspension was moved to a 70° C. oil bath and refluxed for 3 h (1B-E) or 24 h (1F). After the suspension was cooled to room temperature, Hexanes (30 mL) was added. The suspension was filtered through a pad of deactivated silica (5 cm thick) and washed with Hexanes/Et$_2$O=3/1 solution (100 mL). The filtrate was collected, and the solvent was removed. The residue was analyzed by $^1$H and $^{19}$F NMR, if lacking sufficient side products, the imine could be used directly. If not, the residue was applied to deactivated silica column chromatography (Hex/CH$_2$Cl$_2$=100/1 to Hex/CH$_2$Cl$_2$=10/1) to afford imine 1B-1F (29-75% yield). The spectral data of imines 1A-C and 1F were consistent with those reported in Wu & Deng, 2012, J. Am. Chem. Soc. 134:14334-14337.

S18

Ketone S18 was prepared according to Marsilje, et al., 2003, Bioorg. Med. Chem. 11:4487-4501.

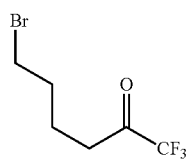

1D

Ar = 4-NO$_2$Ph

Following the general procedure, imine 1D was obtained as light yellow oil (136.6 mg, 29% yield). $^1$H NMR (400 MHz, CDCl$_3$) δ 8.23 (d, J=8.6 Hz, 2H), 7.56 (d, J=8.6 Hz, 2H), 4.82 (s, 2H), 3.45 (t, J=6.4 Hz, 2H), 2.59-2.49 (m, 2H), 2.06-1.90 (m, 2H), 1.79 (d t, J=20.2, 7.7 Hz, 2H). $^{13}$C NMR (100 MHz, CDCl$_3$) δ 161.2 (q, J$_{C-F}$=32.5 Hz), 147.4, 145.6, 128.3, 124.0, 119.8 (q, J$_{C-F}$=281.6 Hz), 54.0, 32.5, 32.3, 26.9, 24.5. $^{19}$F NMR (376 MHz, CDCl$_3$) δ−72.8 (s). IR(CHCl$_3$) ν cm$^{-1}$: 2949, 2874, 2353, 1686, 1606, 1522, 1346, 1198, 1133, 738. HRMS (ESI/[M+H]$^+$) Calcd. for C$_{13}$H$_{15}$BrF$_3$N$_2$O$_2$: 367.0269. found 367.0278.

BnO–[structure]–OMe + TMSCF$_3$ →[CsF]

S19

BnO–[structure]–CF$_3$

S20

To a stirred mixture of methyl 4-benzyloxybutanoate S19 (5.26 g, 25.2 mmol) with CsF (115 mg, 0.76 mmol), TMSCF$_3$ (5.39 g, 37.9 mmol) was added dropwise at 0° C. in 10 minutes. Then the mixture was allowed warm to room temperature and stirred overnight. The remaining methyl 4-benzyloxybutanoate was removed by chromatography (Hexanes/Ethyl Acetate=10/1). To the purified compound was added 48% HF solution and stirred for 4 h. The mixture was quenched by ammonium hydroxide and extracted by CH$_2$Cl$_2$ (50 mL×3). The extracts were combined, dried over Na$_2$SO$_4$ and concentrated under vacuum. The residue was distilled under 2 mmHg and the fraction at 98° C. was collected to afford ketone S20 as colorless oil (3.77 g, 61% yield). $^1$H NMR (400 MHz, CDCl$_3$) δ 7.41-7.26 (m, 5H), 4.48 (s, 2H), 3.51 (t, J=5.9 Hz, 2H), 2.85 (t, J=7.0 Hz, 2H), 2.06-1.89 (m, 2H). $^{13}$C NMR (100 MHz, CDCl$_3$) δ 191.5 (q, J$_{C-F}$=35.0 Hz), 138.2, 128.5, 127.8, 127.7, 115.7 (q, J$_{C-F}$=292.0 Hz), 73.1, 68.3, 33.4, 23.0. $^{19}$F NMR (376 MHz, CDCl$_3$) δ−79.3 (s). IR (CHCl$_3$) ν 3033, 2944, 2867, 1763, 1454, 1405, 1363, 1205, 1144, 1104, 1020, 901, 737, 697 cm$^{-1}$. HRMS (ESI/[M+H]$^+$) Calcd. for C$_{12}$H$_{13}$O$_2$F$_3$: 246.0868. found 246.0868.

1E

BnO–[structure]–N=–CF$_3$ (Ar)

Following the general procedure, Imine 1E was obtained as a light yellow oil (954.1 mg, 59% yield, 87% purity). $^1$H NMR (400 MHz, CDCl$_3$) δ 8.19 (d, J=7.9 Hz, 2H), 7.47 (d, J=8.7 Hz, 2H), 7.38-7.27 (m, 5H), 4.79 (s, 2H), 4.49 (s, 2H), 3.52 (t, J=5.6 Hz, 2H), 2.73-2.60 (m, 2H), 1.95-1.84 (m, 2H). $^{13}$C NMR (100 MHz, CDCl$_3$) δ 161.5 (q, J$_{C-F}$=32.2 Hz), 147.1, 146.0, 138.1, 128.5, 128.2, 127.8, 127.6, 123.7, 119.9 (q, J$_{C-F}$=279.4 Hz), 73.1, 68.8, 53.7, 26.3, 24.7. $^{19}$F NMR (376 MHz, CDCl$_3$) δ−72.5 (s). IR (CHCl$_3$) ν 3033, 2932, 2864, 1685, 1604, 1519, 1343, 1182, 1108, 840, 736, 697 cm$^{-1}$. HRMS (ESI/[M+H]$^+$) Calcd. for C$_{19}$H$_{20}$F$_3$N$_2$O$_3$: 381.1426. found 381.1428.

Aryl trifluoromethyl imines 1G-I were prepared according to Wu & Deng, 2012, J. Am. Chem. Soc. 134:14334-14337.

Vinyl trifluoromethyl imine 1J was prepared according to the following procedure.

Ph–[CH=CH]–C(O)–CF$_3$   +

S21
1.0 eq.

[4-NO$_2$-C$_6$H$_4$-CH$_2$-NH$_2$] →[TiCl$_4$]

3.0 eq.

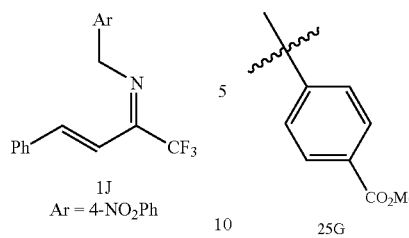

1J
Ar = 4-NO₂Ph

At −40° C., to the solution of trifluoromethyl ketone S21 (1.83 g, 9.1 mmol) in Et₂O (12 mL) was added the solution of 4-NO₂PhCH₂NH₂ (4.17 g, 27.3 mmol) in Et₂O (24 mL). After stirring for 10 mins, the reaction mixture temperature was raised to 0° C. and TiCl₄ (0.87 g, 4.6 mmol) in hexanes (4.5 mL) was added dropwise. After the addition, the orange suspension was allowed to warm up to room temperature. The reaction was monitored by ¹H NMR. After the consumption of S21, the solid was filtered and washed with Et₂O (45 mL×3). The filtrate was combined and concentrated to afford a yellow liquid which was applied to silica (Hexanes/CH₂Cl₂=10/1 to Hexanes/CH₂Cl₂=3/1) to afford the desired 1J with isomerized imine. Further recrystallization from CH₂Cl₂/hexanes afforded 1J as a white solid (461 mg, 16% yield). ¹H NMR (400 MHz, CDCl₃) δ8.28-8.20 (m, 2H), 7.61 (d, J=8.8 Hz, 2H), 7.58-7.51 (m, 2H), 7.49-7.40 (m, 3H), 7.33 (d, J=16.8 Hz, 1H), 6.87 (dd, J=16.8, 1.0 Hz, 1H), 4.97 (s, 2H). ¹³C NMR (100 MHz, CDCl₃) δ 155.73 (q, J$_{C-F}$=32.5 Hz), 147.3, 146.2, 142.1, 134.8, 130.8, 129.2, 128.4, 127.9, 123.9, 120.0 (q, J$_{C-F}$=279.4 Hz), 113.0, 54.3. ¹⁹F NMR (376 MHz, CDCl₃) δ−68.1 (s). IR (CHCl₃) ν 2939, 2453, 1953, 1805, 1629, 1599, 1514, 1450, 1337, 1177, 1121, 969, 758, 696 cm⁻¹. HRMS (EI/[M+H]⁺) Calcd. for C₁₇H₁₃N₂O₂F₃ m/z 334.0929. found m/z 334.0929.

Example 3: Imines

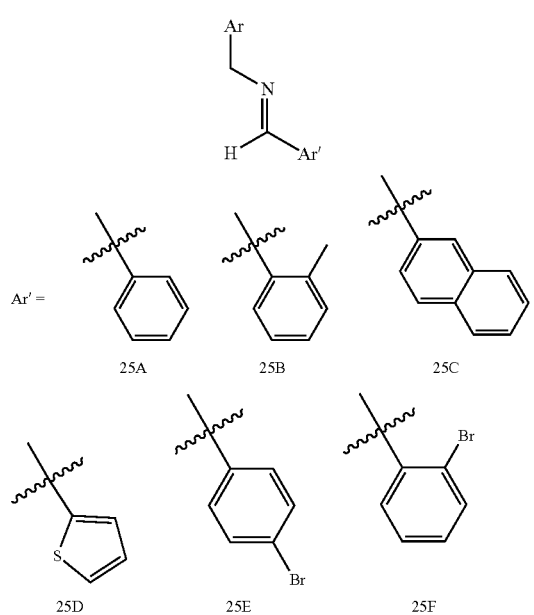

25A-H

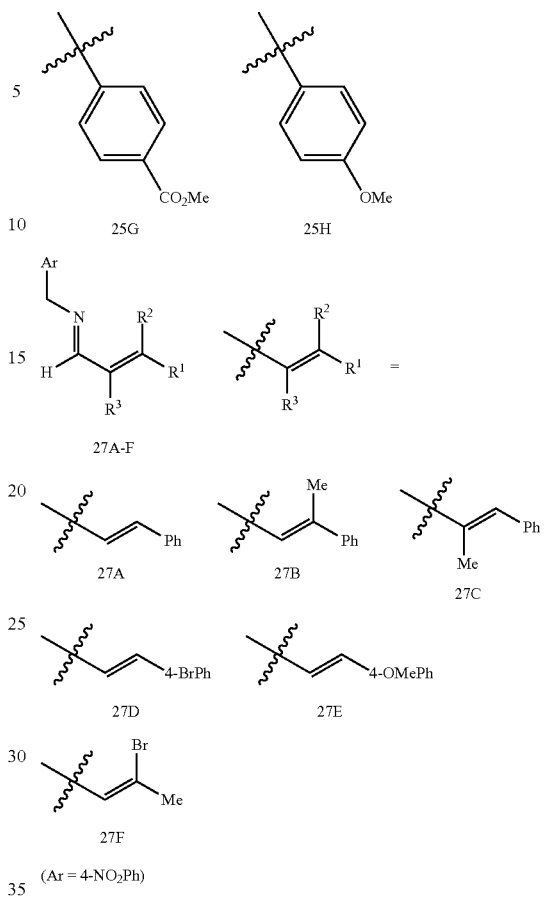

(Ar = 4-NO₂Ph)

General Procedure for the Preparation of 4-NO₂-Benzyl Aldimines:

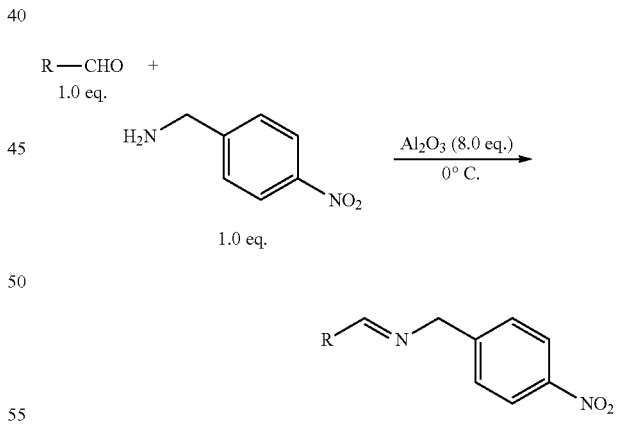

To a solution of 4-NO₂-benzylamine (1.0 eq.) in anhydrous CH₂Cl₂ (0.25 M) was added neutral Al₂O₃ (8.0 eq.) at 0° C., followed by dropwise addition of a solution of aldehyde (1.0 eq.) in anhydrous CH₂Cl₂ (1.0 M) over 15 min. The reaction mixture was further stirred at 0° C. for additional 1 h, after which it was filtered through a short pad of Celite and concentrated. The crude product was triturated in 3% ethyl acetate solution in hexanes (0.25 M) for 2 h. The suspension was filtered and dried under vacuum to give the solid aldimine product in high purity.

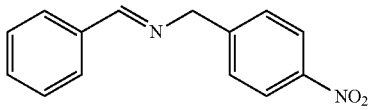

25A

Compound 25A was prepared according to the general procedure as a white solid in 88% yield. $^1$H NMR (400 MHz, CDCl$_3$) δ 8.44 (s, 1H), 8.19 (d, J=8.7 Hz, 2H), 7.81 (dd, J=7.5, 2.1 Hz, 2H), 7.52 (d, J=8.6 Hz, 2H), 7.49-7.38 (m, 3H), 4.89 (s, 2H). $^{13}$C NMR (100 MHz, CDCl$_3$) δ 163.1, 147.1, 146.9, 135.7, 131.1, 128.6, 128.3, 128.2, 123.5, 63.8. IR (CHCl$_3$) ν 2847, 1646, 1602, 1519, 1345, 1220, 1109, 1037, 769, 695. HRMS (ESI/[M+H]$^+$) Calcd. for C$_{14}$H$_{13}$N$_2$O$_2$ m/z 241.0977. found m/z 241.0980.

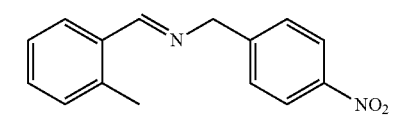

25B

Compound 25B was prepared according to the general procedure as a yellow oil in 77% yield. $^1$H NMR (400 MHz, CDCl$_3$) δ 8.75 (s, 1H), 8.20 (d, J=8.7 Hz, 2H), 7.93 (d, J=7.7 Hz, 1H), 7.54 (d, J=8.8 Hz, 2H), 7.34 (t, J=7.4 Hz, 1H), 7.26 (dd, J=8.8, 5.7 Hz, 1H), 7.21 (d, J=7.5 Hz, 1H), 4.92 (s, 2H), 2.55 (s, 3H). $^{13}$C NMR (100 MHz, CDCl$_3$) δ 161.7, 147.3, 146.7, 137.8, 133.5, 130.8, 130.5, 128.1, 127.6, 123.4, 64.3, 19.3. IR (CHCl$_3$) ν 2870, 1641, 1602, 1519, 1345, 1285, 1220, 1110, 1036, 852, 770. HRMS (ESI/[M+H]$^+$) Calcd. for C$_{15}$H$_{15}$N$_2$O$_2$ m/z 255.1134. found m/z 255.1135.

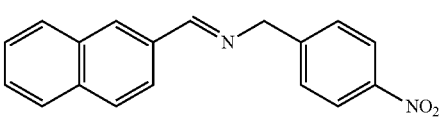

25C

Compound 25C was prepared according to the general procedure as a white solid in 73% yield. $^1$H NMR (400 MHz, CDCl$_3$) δ 8.60 (s, 1H), 8.23 (d, J=8.2 Hz, 2H), 8.10 (s, 1H), 8.07 (d, J=8.5 Hz, 1H), 7.99-7.76 (m, 2H), 7.69-7.37 (m, 4H), 4.97 (s, 2H). $^{13}$C NMR (100 MHz, CDCl$_3$) δ 163.2, 147.1, 147.0, 134.9, 133.36, 133.0, 130.5, 128.6, 128.4, 127.9, 127.4, 126.6, 123.7, 123.6, 64.0. IR (CHCl$_3$) ν 2835, 1640, 1600, 1513, 1349, 1219, 1035, 835, 771. HRMS (ESI[M+H]$^+$) Calcd. for C$_{18}$H$_{15}$N$_2$O$_2$ m/z 291.1134. found m/z 291.1131.

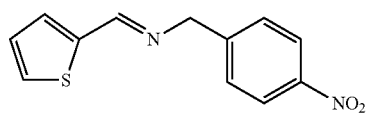

25D

Compound 25D was prepared according to the general procedure as a yellow solid in 75% yield. $^1$H NMR (400 MHz, CDCl$_3$) δ 8.52 (s, 1H), 8.19 (d, J=8.6 Hz, 2H), 7.50 (d, J=8.4 Hz, 2H), 7.45 (d, J=5.0 Hz, 1H), 7.38 (d, J=3.4 Hz, 1H), 7.10 (dd, J=4.7, 3.9 Hz, 1H), 4.86 (s, 2H). $^{13}$C NMR (100 MHz, CDCl$_3$) δ 156.3, 146.9, 146.8, 141.7, 131.2, 129.5, 128.2, 127.4, 123.5, 63.3. IR (CHCl$_3$) ν 2838, 1635, 1602, 1518, 1431, 1345, 1219, 1110, 1045, 846, 771, 716. HRMS (ESI[M+H]$^+$) Calcd. for C$_{12}$H$_{11}$N$_2$O$_2$S m/z 247.0541. found m/z 247.0539.

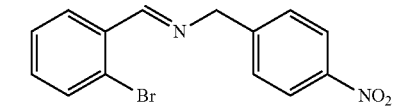

25E

Compound 25E was prepared according to the general procedure as a white solid in 71% yield. $^1$H NMR (400 MHz, CDCl$_3$) δ 8.39 (s, 1H), 8.21 (d, J=8.7 Hz, 2H), 7.67 (d, J=8.4 Hz, 2H), 7.58 (d, J=8.4 Hz, 2H), 7.52 (d, J=8.5 Hz, 2H), 4.89 (s, 2H). $^{13}$C NMR (100 MHz, CDCl$_3$) δ 161.8, 146.9, 146.8, 134.5, 131.9, 129.6, 128.3, 125.5, 123.6, 63.8. IR (CHCl$_3$) ν 2845, 1644, 1592, 1516, 1346, 1228, 1067, 1012, 858, 771. HRMS (ESI/[M+H]$^+$) Calcd. for C$_{14}$H$_{12}$BrN$_2$O$_2$ m/z 319.0082. found m/z 319.0079.

25F

Compound 25F was prepared according to the general procedure as a yellow solid in 72% yield. $^1$H NMR (400 MHz, CDCl$_3$) δ 8.82 (s, 1H), 8.22 (d, J=8.7 Hz, 2H), 8.09 (dd, J=7.7, 1.7 Hz, 1H), 7.60 (d, J=7.9 Hz, 1H), 7.54 (d, J=8.5 Hz, 2H), 7.37 (t, J=7.4 Hz, 1H), 7.31 (td, J=7.6, 1.8 Hz, 1H), 4.95 (s, 2H). $^{13}$C NMR (100 MHz, CDCl$_3$) δ 162.0, 146.9, 146.7, 134.0, 133.0, 132.2, 128.8, 128.3, 127.6, 125.2, 123.5, 63.9. IR (CHCl$_3$) ν 2838, 1637, 1601, 1519, 1433, 1345, 1273, 1218, 1111, 1022, 853, 770, 687. HRMS (ESI/[M+M]+) Calcd. for C$_{14}$H$_{12}$BrN$_2$O$_2$ m/z 319.0082. found m/z 319.0085.

25G

Compound 25G was prepared according to the general procedure as a white solid in 74% yield. $^1$H NMR (400 MHz, CDCl$_3$) δ 8.48 (s, 1H), 8.20 (d, J=7.9 Hz, 2H), 8.10 (d, J=7.6 Hz, 2H), 7.86 (d, J=7.6 Hz, 2H), 7.53 (d, J=7.9 Hz, 2H), 4.92 (s, 2H), 3.93 (s, 3H). $^{13}$C NMR (100 MHz, CDCl$_3$) δ 166.3, 162.0, 146.9, 146.6, 139.4, 132.1, 129.7, 128.3, 128.1, 123.5, 63.9, 52.1. IR (CHCl$_3$) ν 2870, 1720, 1639, 1602, 1516, 1439, 1411, 1345, 1286, 1219, 1113, 1019, 963, 847, 770, 700. HRMS (ESI/[M+H]$^+$) Calcd. for C$_{16}$H$_{15}$N$_2$O$_4$ m/z 299.1032. found m/z 299.1031.

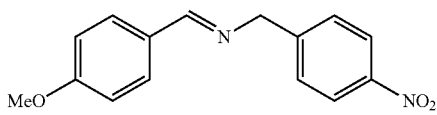

25H

Compound 25H was prepared according to the general procedure as a yellow solid in 78% yield. $^1$H NMR (400 MHz, CDCl$_3$) δ 8.36 (s, 1H), 8.19 (d, J=8.8 Hz, 2H), 7.75 (d, J=8.7 Hz, 2H), 7.52 (d, J=8.3 Hz, 2H), 6.95 (d, J=8.7 Hz, 2H), 4.86 (s, 2H), 3.86 (s, 3H). $^{13}$C NMR (100 MHz, CDCl$_3$) δ 162.4, 161.9, 147.4, 146.7, 129.8, 128.6, 128.2, 123.5, 114.0, 63.8, 55.2. IR (CHCl$_3$) ν 2874, 1645, 1604, 1517, 1346, 1252, 1219, 1170, 1031, 838, 770. $_{HRMS}$ (ESI/[M+H]$_+$) Calcd. for C$_{15}$H$_{15}$N$_2$O$_3$ m/z 271.1083. found m/z 271.1086.

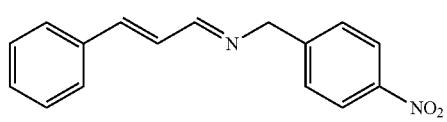

27A

Compound 27A was prepared according to the general procedure as a yellow solid in 72% yield. $^1$H NMR (400 MHz, CDCl$_3$) δ 8.20 (m, 3H), 7.50 (m, 4H), 7.38 (m, 3H), 7.05 (d, J=16.0 Hz, 1H), 6.97 (dd, J=16.1, 8.1 Hz, 1H), 4.80 (s, 2H). $^{13}$C NMR (100 MHz, CDCl$_3$) δ 164.6, 146.9, 142.9, 135.3, 129.4, 128.8, 128.4, 127.5, 127.3, 123.6, 64.0. IR (CHCl$_3$) ν 2860, 1636, 1603, 1519, 1446, 1346, 1218, 1156, 1109, 1003, 970, 854, 770, 693. HRMS (ESI/[M+H]$^+$) Calcd. for C$_{16}$H$_{15}$N$_2$O$_2$ m/z 267.1134. found m/z 267.1128.

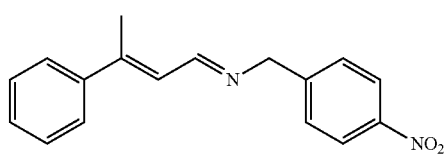

27B

Compound 27B was prepared according to the general procedure as red oil in 85% yield. $^1$H NMR (400 MHz, CDCl$_3$) δ 8.55 (d, J=9.2 Hz, 1H), 8.21 (d, J=8.6 Hz, 2H), 7.45-7.61 (m, 4H), 7.29-7.46 (m, 3H), 6.68 (d, J=9.3 Hz, 1H), 4.83 (s, 2H), 2.38 (s, 3H). $^{13}$C NMR (100 MHz, CDCl$_3$) δ 161.6, 147.3, 147.2, 147.1, 146.9, 141.4, 128.6, 128.4, 128.4, 125.8, 125.7, 123.6, 64.4, 16.3. IR (CHCl$_3$) ν 2872, 1630, 1603, 1519, 1443, 1345, 1218, 1171, 1109, 1022, 882, 851, 768, 697. HRMS (ESI/[M+H]$^+$) Calcd. for C$_{17}$H$_{17}$N$_2$O$_2$ m/z 281.1290. found m/z 281.1291.

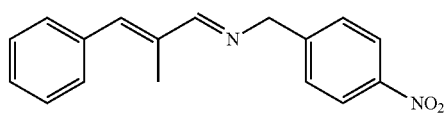

27C

Compound 27C was prepared according to the general procedure as a yellow solid in 70% yield. $^1$H NMR (400 MHz, CDCl$_3$) δ 8.21 (d, J=8.7 Hz, 2H), 8.15 (s, 1H), 7.51 (d, J=8.6 Hz, 2H), 7.46-7.35 (m, 4H), 7.31 (m, 1H), 4.84 (s, 2H), 2.21 (s, 3H). $^{13}$C NMR (100 MHz, CDCl$_3$) δ 168.0, 147.4, 146.8, 140.2, 136.5, 136.2, 129.3, 128.32, 128.2, 127.9, 123.5, 63.5, 13.2. IR (CHCl$_3$) ν 2854, 1624, 1601, 1514, 1444, 1408, 1346, 1290, 1215, 1109, 1049, 1020, 863, 836, 768, 699. HRMS (ESI/[M+H]$^+$) Calcd. for C$_{17}$H$_{17}$N$_2$O$_2$ m/z 281.1290. found m/z 281.1291.

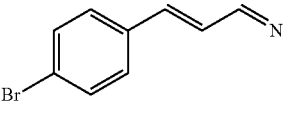

27D

Compound 27D was prepared according to the general procedure as a yellow solid in 73% yield. $^1$H NMR (400 MHz, CDCl$_3$) δ 8.20 (d, J=8.6 Hz, 2H), 8.18 (m, 1H), 7.51 (d, J=8.6 Hz, 2H), 7.48 (d, J=8.4 Hz, 2H), 7.35 (d, J=8.4 Hz, 2H), 6.95 (m, 2H), 4.78 (s, 2H). $^{13}$C NMR (100 MHz, CDCl$_3$) δ 164.3, 146.9, 146.7, 141.4, 134.3, 131.9, 128.7, 128.4, 128.2, 123.7, 123.4, 64.1. IR (CHCl$_3$) ν 2848, 1677, 1635, 1602, 1517, 1490, 1405, 1345, 1218, 1156, 1109, 1072, 1007, 969, 853, 802, 770. HRMS (ESI/[M+H]$^+$) Calcd. for C$_{16}$H$_{14}$BrN$_2$O$_2$ m/z 345.0239. found m/z 345.0234.

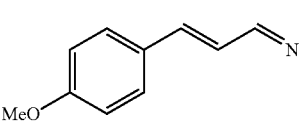

27E

Compound 27E was prepared according to the general procedure as a yellow solid in 78% yield. $^1$H NMR (400 MHz, CDCl$_3$) δ 8.20 (d, J=8.6 Hz, 2H), 8.15 (d, J=8.6 Hz, 1H), 7.48 (d, J=8.6 Hz, 2H), 7.44 (d, J=8.6 Hz, 2H), 6.99 (d, J=15.9 Hz, 1H), 6.91 (d, J=8.6 Hz, 2H), 6.85 (dd, J=8.6, 15.9 Hz, 1H), 4.77 (s, 2H), 3.83 (s, 3H). $^{13}$C NMR (100 MHz, CDCl$_3$) δ 164.8, 160.6, 147.1, 146.8, 142.6, 128.7, 128.4, 128.0, 125.3, 123.5, 114.2, 55.2. IR (CHCl$_3$) ν 2838, 1634, 1602, 1516, 1437, 1345, 1306, 1253, 1219, 1175, 1158, 1031, 971, 855, 822, 770. HRMS (ESI/[M+H]$^+$) Calcd. for C$_{17}$H$_{17}$N$_2$O$_3$ m/z 297.1239. found m/z 297.1241.

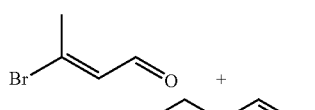

27F

A modified procedure was followed: to a solution of 4-NO$_2$-benzylamine (304 mg, 0.20 mmol) in anhydrous PhMe (1.5 mL) was added neutral Al$_2$O$_3$ (163 mg, 1.60 mmol) at 0° C., followed by dropwise addition a solution of (Z)-3-bromobut-2-enal (298 mg, 0.20 mmol) in anhydrous toluene (0.5 mL) over 15 min. The reaction mixture was further stirred at 0° C. for additional 1 h, after which it was filtered through a short pad of Celite and the crude product in toluene solution (ca. 0.1 M) was used for the next step directly. $^1$H NMR (400 MHz, CDCl$_3$) δ 8.20 (d, J=8.5 Hz, 3H), 7.45 (d, J=8.5 Hz, 2H), 6.72 (d, J=9.1 Hz, 1H), 2.57 (s, 3H). $^{13}$C NMR (100 MHz, CDCl$_3$) δ 164.9, 160.8, 146.6, 140.6, 128.3, 126.3, 123.6, 62.6, 17.7; IR (CHCl$_3$) ν 2852, 1638, 1601, 1518, 1434, 1344, 1177, 1110, 1016, 955, 912, 850, 817, 772, 739, 699. HRMS (ESI/[M+H]$^+$) Calcd. for C$_{11}$H$_{12}$BrN$_2$O$_2$ m/z 283.0082. found m/z 283.0077.

Example 4: Asymmetric Umpolung Reaction of Imines

Racemic Amino-Alcohol 22 or 23

The racemic product was obtained by mixing the product from C-21 and CD-21 catalyzed reactions.

Catalytic Asymmetric Umpolung Reaction of Trifluoromethyl Imines

The catalyst C-21b was dissolved in PhMe (5.0×10$^{-3}$M) and added as a solution. The catalyst CD-21b was dissolved in CHCl$_3$ (5.0×10$^{-3}$ M). After the addition of the solution of CD-21b in CHCl$_3$, the solvent was removed under vacuum before the addition of imine, enal, PhMe and KOH.

Monitoring the Reaction Between 1A and 8a with C-21b by $^1$H and $^{19}$F NMR Analyses (Entry 12, FIG. 3B)

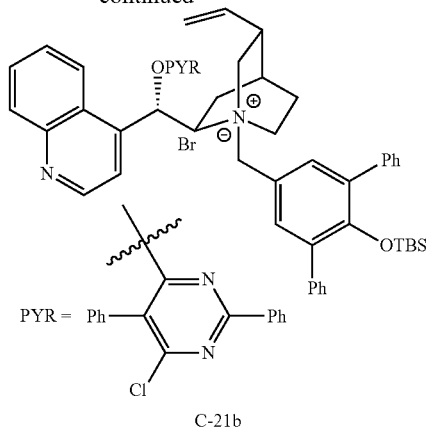

At −20° C., to the solution of imine 1A (6.2 mg, 0.025 mmol), enal 8a (4.2 μL, 0.05 mmol) and catalyst C-21b (0.0025 mmol, 1.0 mol %) in toluene (0.25 mL) was added KOH (0.3 μL, 50 wt % aq., 10 mol %). The mixture was then vigorously stirred and turned purple in a few minutes. The reaction was monitored at 10 min, 30 min and 2 h. After the reaction was completed or reached the maximum conversion, the mixture was passed through a small pad of deactivated silica (5 mm thick) and washed with Et$_2$O (0.5 mL×3). The filtrates were then combined and concentrated under vacuum to afford a light yellow liquid which was subject to $^{19}$F and $^1$H NMR analysis. Throughout the reaction, the adducts from 1,2-addition or [3+2] cycloaddition of imine 1A and enal 8a were not detected. 1H NMR, reaction at 2 h, 99% conv.

General Procedure for Imine Umpolung Reaction Method A1 (Entries 1-9, FIG. 4A-4B), R$^2$=Alkyl or Aryl

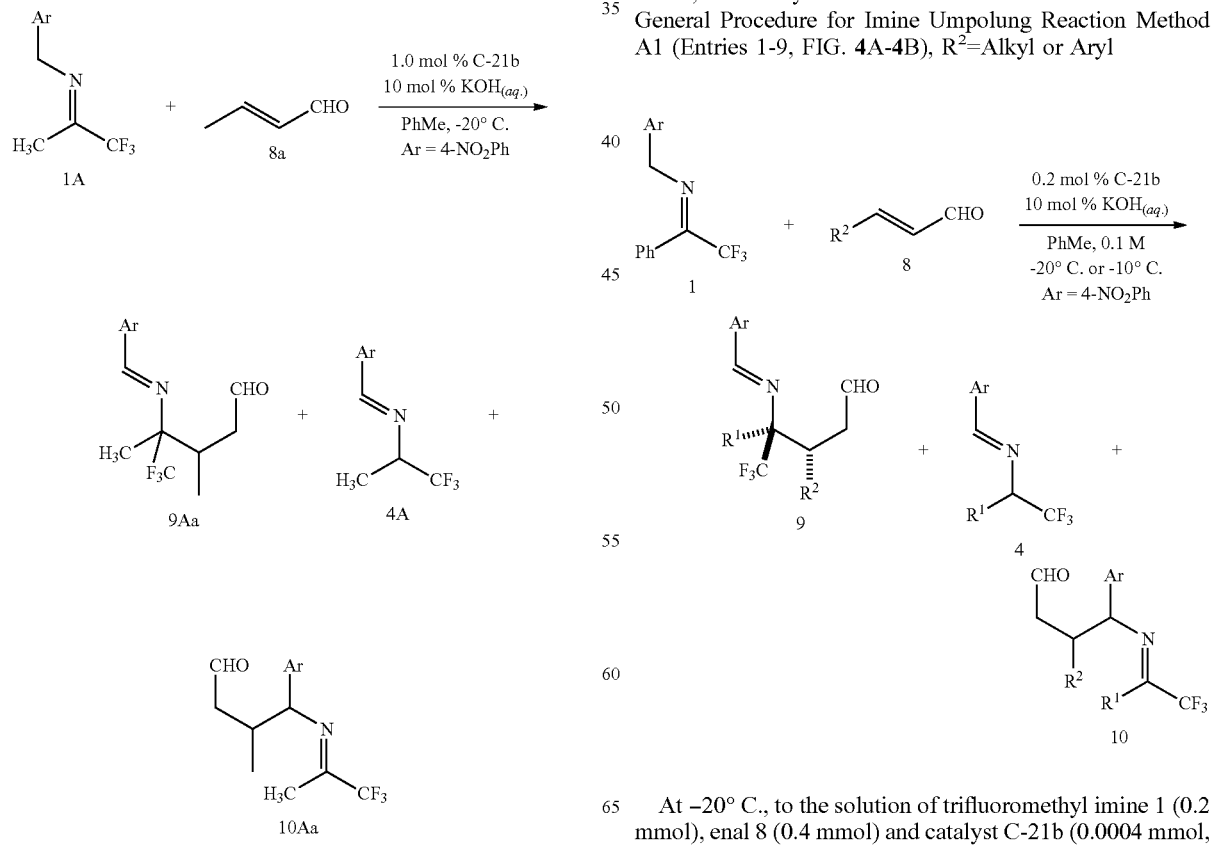

At −20° C., to the solution of trifluoromethyl imine 1 (0.2 mmol), enal 8 (0.4 mmol) and catalyst C-21b (0.0004 mmol, 0.2 mol %) in toluene was added KOH (2.2 μL, 50 wt % aq., 0.02 mmol). The mixture was then vigorously stirred and turned purple in a few minutes.

The reaction was monitored by taking an aliquot of the reaction mixture (50 μL) which was concentrated and subject to NMR analysis. After the reaction was completed or reached the maximum conversion, the mixture was passed through a small pad of deactivated silica (5 mm thick) and washed with Et$_2$O (1.0 mL×3). The filtrates were combined, concentrated under vacuum to afford the crude amine 9 as a yellow liquid. The conversion, chemoselectivity, regioselectivity and diastereoselectivity were determined by NMR analysis of the crude umpolung reaction mixture.

General Procedure for Imine Umpolung Reaction Method A2 (Entries 10-17, FIG. 4B), R$^2$=H

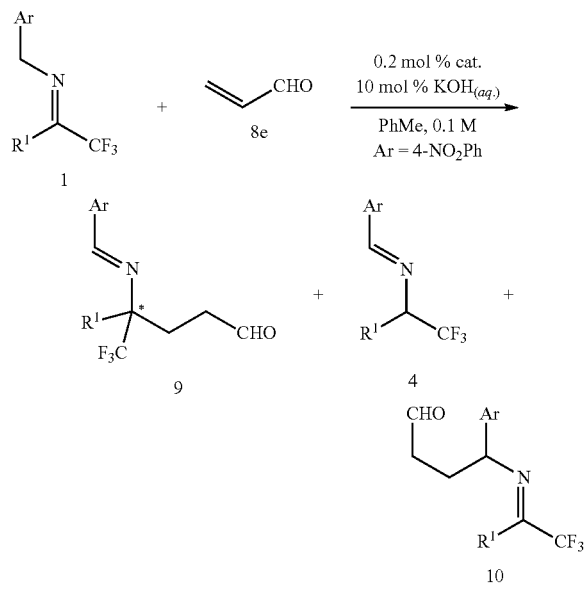

The solution of trifluoromethyl imine 1 (0.2 mmol) and catalyst C-21b (0.0004 mmol, 0.2 mol %) in toluene (1.7 mL) was cooled to the required temperature (−10° C. for alkyl imines, and −20° C. for aryl and alkenyl imines). KOH (2.2 μt, 50 wt % aq., 0.02 mmol) was added right after a solution of acrolein (8e, 0.4 mmol) in PhMe (0.3 mL) started being added with a syringe pump (0.1 mL/h). After the completion of the slow addition, the mixture was passed through a small pad of deactivated silica (5 mm thick) and washed with Et$_2$O (1 mL×3). The filtrates were combined and concentrated under vacuum to afford the crude amine 9 as a yellow liquid. The conversion, chemoselectivity and regioselectivity were determined by NMR analysis of the crude umpolung reaction mixture.

General Procedure for Amine 9 Reduction B1 (Entries 1-13, FIGS. 4A-4B), R$^1$=Alkyl

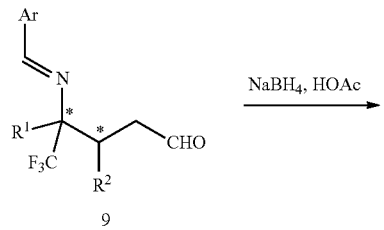

-continued

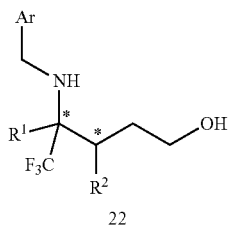

To a solution of CH$_2$Cl$_2$/EtOH=4/1 solution (2.0 mL) was added NaBH$_4$ (38 mg, 1.0 mmol). The suspension was stirred at rt for 5 mins and moved to a −20° C. bath. Then the above crude amine 9 was dissolved in CH$_2$Cl$_2$ (0.5 mL), cooled to −20° C. and added in one portion. CH$_2$Cl$_2$ (0.25 mL×2) was used to rinse the vial and added to the reaction mixture. After 20 mins, HOAc (0.23 mL, 4.0 mmol) was added slowly and the mixture was warmed to room temperature and stirred for 1 h. Then saturated NaHCO$_3$ was added slowly to quench the reaction and the mixture was made alkaline with NH$_4$OH (sat.). The organic layer was separated and the aqueous layer was then extracted with CH$_2$Cl$_2$ (5.0 mL×3). The organic extracts were combined, dried over Na$_2$SO$_4$, and concentrated under vacuum. The residue was applied to silica gel column chromatography (Hex/Ether=100/1 to 5/1) to afford the amino-alcohol 22.

General Procedure for Amine 9 Hydrolysis B2 (Entries 14-17, FIG. 4B), R$^1$=Aryl or Alkenyl

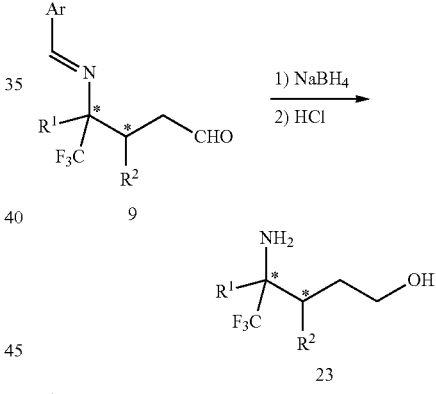

R$^1$ = Ar, Alkenyl

To CH$_2$Cl$_2$/EtOH=4/1 solution (2.0 mL) was added NaBH$_4$ (11 mg, 0.3 mmol). The suspension was stirred at room temperature for 5 mins and moved to −20° C. bath. Then the above crude amine 9 was dissolved in CH$_2$Cl$_2$ (0.5 mL), cooled to −20° C. and added in one portion. CH$_2$Cl$_2$ (0.25 mL×2) was used to rinse the vial and added to the reaction mixture. After 20 mins, the mixture was filtered through Celite and washed with CH$_2$Cl$_2$ (1.0 mL×3). The filtrates were combined and concentrated under vacuum. THF (2.0 mL) was added to dissolve the residue and the solution was cooled to 0° C. Saturated NaHCO$_3$ (1.0 mL) was added and the mixture was well stirred. After 10 mins, 3 N HCl (1.0 mL) was slowly added and the mixture was warmed to room temperature and stirred for 1 h. The THF was removed under vacuum and the aqueous phase was made alkaline with NH$_4$OH (sat.). Then the aqueous layer was extracted with CH$_2$Cl$_2$ (4.0 mL×4). The organic extracts were combined, dried over Na$_2$SO$_4$ and concentrated under vacuum. The residue was then applied to silica gel column chromatography (CH$_2$Cl$_2$ to CH$_2$Cl$_2$/MeOH=100/1) to afford the amino-alcohol 23.

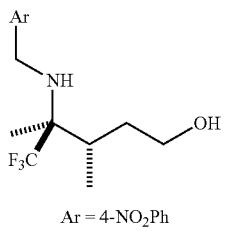

22Aa

Ar = 4-NO$_2$Ph

Aminoalcohol (−)-22Aa. Following method A1, amine 9Aa was obtained from a reaction catalyzed by C-21b (0.2 mol %) at −20° C. for 5 h. $^1$H and $^{19}$F NMR analysis of the crude umpolung reaction mixture showed 9/4>95/5, 9/10>95/5 and d.r.=93/7. The reaction was worked up following general procedure B1. The amino-alcohol product 22Aa was obtained as a white solid in 81% yield after flash chromatography (Hexanes/Et$_2$O=50/1 to 4/1) and 95% ee as determined by HPLC analysis [Daicel Chiralpak OJ-H, Hexanes/IPA=90/10, 1.0 ml/min, λ 254 nm, t(major)=11.85 min, t(minor)=13.40 min]. $[\alpha]_D^{20}$=−0.9 (c=1.22, CHCl3). $^1$H NMR (400 MHz, CDCl$_3$) δ 8.22-8.11 (m, 2H), 7.55 (d, J=8.8 Hz, 2H), 4.04 (d, J=13.7 Hz, 1H), 3.89 (d, J=13.8 Hz, 1H), 3.80 (ddd, J=10.5, 6.1, 4.4 Hz, 1H), 3.70-3.60 (m, 1H), 2.15 (ddd, J=9.8, 7.1, 5.1 Hz, 2H), 1.78 (bs, 1H), 1.52 (bs, 1H), 1.35-1.23 (m, 1H), 1.19 (d, J=0.7 Hz, 3H), 1.05 (dd, J=6.7, 1.2 Hz, 3H). $^{13}$C NMR (100 MHz, CDCl$_3$) δ 148.3, 147.2, 128.8, 128.5 (q, J$_{C-F}$=292.1 Hz), 123.8, 62.4 (q, J$_{C-F}$=23.0 Hz), 61.0, 46.1, 33.9, 31.5, 16.0, 14.8. $^{19}$F NMR (376 MHz, CDCl$_3$) δ=−71.3; IR (CHCl$_3$) ν 3355, 2947, 2883, 1606, 1519, 1465, 1346, 1278, 1137, 1075, 1015, 852, 742, 700 cm$^{-1}$. HRMS (ESI/[M+H]+) Calcd. for C$_{14}$H$_{20}$F$_3$N$_2$O$_3$ m/z 321.1426. found m/z 321.1422.

Following general procedure A1, the opposite enantiomer of amine 9Aa was obtained from a reaction catalyzed by CD-21b (0.2 mol %) at −20° C. for 5 h. $^1$H and $^{19}$F NMR analysis of the crude umpolung reaction mixture showed 9/4>95/5, 9/10>95/5 and d.r.=91/9. The reaction was worked up following general procedure B1. (+)-22Aa was obtained as a white solid in 84% yield after flash chromatography (Hexanes/Et$_2$O=50/1 to 4/1) and 88% ee determined by HPLC analysis. $[60]_D^{20}$=+0.6 (c=1.06, CHCl$_3$)

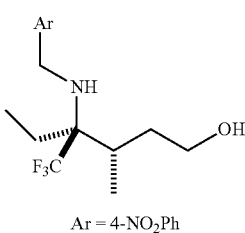

22Ba

Ar = 4-NO$_2$Ph

Aminoalcohol (−)-22Ba. Following general procedure A1, amine 9Ba was obtained from a reaction catalyzed by C-21b (0.2 mol %) at −20° C. for 5 h. $^1$H and $^{19}$F NMR analysis of the crude umpolung reaction mixture showed 9/4>95/5, 9/10>95/5 and d.r.=91/9. The reaction was worked up following general procedure B1. The amino-alcohol product (−)-22Ba was obtained as a light yellow liquid in 84% yield after flash chromatography (Hexanes/Et$_2$O=50/1 to 5/1) and 94% ee as determined by HPLC analysis [Daicel Chiralpak OJ-H, Hexanes/IPA=90/10, 1.0 ml/min, λ 254 nm, t(major)=11.01 min, t(minor)=12.43 min]. $[\alpha]_D^{20}$=−10.0 (c=1.14, CHCl$_3$). $^1$H NMR (400 MHz, CDCl$_3$) δ 8.16 (d, J=8.7 Hz, 2H), 7.56 (d, J=8.6 Hz, 2H), 4.02 (d, J=13.7 Hz, 1H), 3.91-3.74 (m, 2H), 3.64 (td, J=10.0, 5.1 Hz, 1H), 2.33-2.20 (m, 1H), 2.12 (ddd, J=14.0, 9.2, 4.4 Hz, 1H), 1.89-1.58 (m, 4H), 1.35-1.22 (m, 1H), 1.03 (t, J=10.9 Hz, 3H), 0.96 (t, J=7.5 Hz, 3H). $^{13}$C NMR (100 MHz, CDCl$_3$) δ 148.4, 147.2, 128.8, 128.4 (q, J$_{C-F}$=294.4 Hz), 123.8, 64.5 (q, J$_{C-F}$=21.5 Hz), 61.0, 45.7, 33.9, 30.8, 22.7, 14.1, 7.4. $^{19}$F NMR (376 MHz, CDCl$_3$) δ=−65.8 (s). IR (CHCl$_3$) ν 3358, 2954, 2890, 1605, 1519, 1462, 1345, 1232, 1172, 1132, 1079, 1054, 921, 853, 748, 700 cm$^{-1}$. HRMS (ESI/[M+H]$^+$) Calcd. for C$_{15}$H$_{22}$N$_2$O$_3$F$_3$ m/z 335.1583. found m/z 335.1587.

Following general procedure A1, the opposite enantiomer of amine 9Ba was obtained from a reaction catalyzed by CD-21b (0.2 mol %) at −20° C. for 5 h. $^1$H and $^{19}$F NMR analysis of the crude umpolung reaction mixture showed 9/4>95/5, 9/10>95/5 and d.r.=91/9. The reaction was worked up following general procedure B1. (+)-22Ba was obtained as a light yellow liquid in 84% yield after flash chromatography (Hexanes/Et$_2$O=50/1 to 5/1) and 82% ee determined by HPLC analysis. $[\alpha]_D^{20}$=+9.4 (c=1.10, CHCl$_3$).

22Ca

Ar = 4-NO$_2$Ph

Aminoalcohol (−)-22Ca. Following general procedure A1, amine 9Ca was obtained from a reaction catalyzed by C-21b (0.2 mol %) at −20° C. for 5 h. $^1$H and $^{19}$F NMR analysis of the crude umpolung reaction mixture showed 9/4=95/5, 9/10>95/5 and d.r.=91/9. The reaction was worked up following general procedure B1. The amino-alcohol product (−)-22Ca was obtained as light yellow liquid in 83% yield after flash chromatography (Hexanes/Et$_2$O=50/1 to 5/1) and 96% ee as determined by HPLC analysis [Daicel Chiralpak AD-H, Hexanes/IPA=96.5/3.5, 1.0 ml/min, λ 254 nm, t(major)=15.59 min, t(minor)=14.54 min]. $[\alpha]_D^{20}$=−12.9 (c=1.23, CHCl$_3$). $^1$H NMR (400 MHz, CDCl$_3$) δ 8.17 (d, J=8.6 Hz, 2H), 7.55 (d, J=8.5 Hz, 2H), 4.01 (d, J=13.6 Hz, 1H), 3.90-3.75 (m, 2H), 3.64 (td, J=9.9, 5.1 Hz, 1H), 2.33-2.20 (m, 1H), 2.19-2.06 (m, 1H), 1.82-1.64 (m, 3H)., 1.63-1.50 (m, 1H), 1.38-1.24 (m, 5H), 1.05 (d, J=6.6 Hz, 3H), 0.92 (t, J=6.8 Hz, 3H). $^{13}$C NMR (100 MHz, CDCl$_3$) δ 148.4, 147.2, 128.8, 128.3 (q, J$_{C-F}$=299.7 Hz), 123.8, 64.5 (q, J$_{C-F}$=21.7 Hz), 61.1, 45.7, 33.9, 30.9, 29.9, 24.9, 23.6, 14.2 (q, J$_{C-F}$=1.8 Hz), 14.0. $^{19}$F NMR (376 MHz, CDCl$_3$) δ=−65.9 (s). IR (CHCl$_3$) ν 2961, 2872, 1606, 1558, 1519, 1469, 1345, 1212, 1133, 1058, 978, 909, 852, 733, 646 cm$^{-1}$. HRMS (ESI/[M+H]+) Calcd. for C$_{17}$H$_{26}$N$_2$O$_3$F$_3$ m/z 363.1896. found m/z 363.1887.

Following general procedure A1, the opposite enantiomer of amine 9Ca was obtained from a reaction catalyzed by CD-21b (0.2 mol %) at −20° C. for 5 h. $^1$H and $^{19}$F NMR analysis of the crude umpolung reaction mixture showed 9/4>95/5, 9/10>95/5 and d.r.=91/9. The reaction was worked up following general procedure B1. (+)-22Ca was obtained as light yellow liquid in 76% yield after flash chromatography (Hexanes/Et$_2$O=50/1 to 5/1) and 81% ee determined by HPLC analysis. [α]$_D^{20}$=+14.2 (c=1.06, CHCl$_3$).

Modified Procedure for Amine 9Da Reduction (B1')

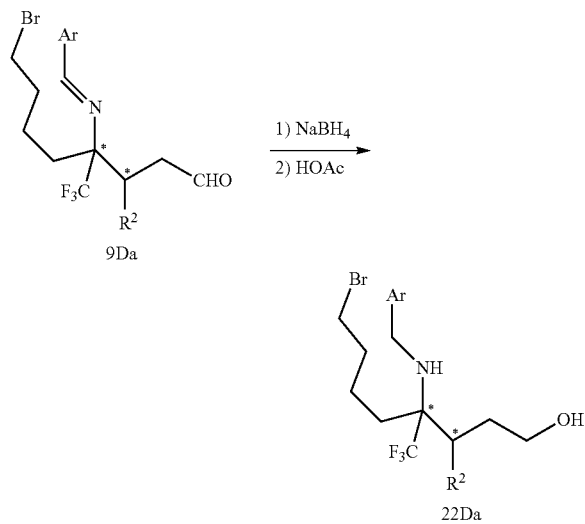

To a solution of CH$_2$Cl$_2$/EtOH=4/1 solution (2.0 mL) was added NaBH$_4$ (38.0 mg, 1.0 mmol). The suspension was stirred at rt for 5 mins and moved to −20° C. bath. Then the above amine 9Da was dissolved in CH$_2$Cl$_2$ (0.5 mL), cooled to −20° C. and added in one portion. CH$_2$Cl$_2$ (0.25 mL×2) was used to rinse the vial and added to the reaction mixture. After 20 mins, HOAc (0.23 mL, 4.0 mmol) was added slowly and the mixture was moved to rt and stirred for 1 h. Then saturated NaHCO$_3$ was added slowly to adjust the pH=8. The organic layer was separated and the aqueous layer was then extracted with CH$_2$Cl$_2$ (5 mL×6). The organic extracts were combined, dried over Na$_2$SO$_4$, and concentrated under vacuum. The residue was then applied to flash column chromatography (Hex/Ether=100/1 to 5/1) to afford the amino-alcohol 22Da.

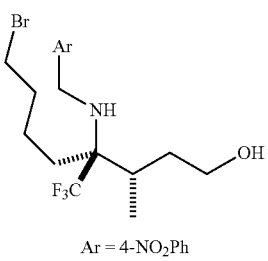

Aminoalcohol (−)-22Da. Following general procedure A1, amine 9Da was obtained from a reaction catalyzed by C-21b (0.2 mol %) at −20° C. for 5 h. $^1$H and $^{19}$F NMR analysis of the crude umpolung reaction mixture showed 9/4>95/5, 9/10>95/5 and d.r.=91/9. The reaction was worked up following modified procedure B1'. The amino-alcohol product (−)-22Da was obtained as a light yellow liquid in 75% yield after flash chromatography (Hexanes/Et$_2$O=50/1 to 2/1) and 96% ee as determined by HPLC analysis [Daicel Chiralpak AD-H, Hexanes/IPA=97/3, 1.0 ml/min, λ 254 nm, t(major)=41.33 min, t(minor)=37.79 min]. [α]$_D^{20}$=−16.9 (c=0.91, CHCl3). $^1$H NMR (400 MHz, CDCl$_3$) δ 8.19 (d, J=8.6 Hz, 2H), 7.56 (d, J=8.5 Hz, 2H), 4.02 (d, J=13.5 Hz, 1H), 3.92-3.75 (m, 2H), 3.65 (td, J=10.0, 4.8 Hz, 1H), 3.42 (t, J=6.6 Hz, 2H), 2.39-2.24 (m, 1H), 2.17-2.06 (m, 1H), 1.94-1.81 (m, 2H), 1.73 (d, J=9.5 Hz, 1H), 1.59 (d, J=21.7 Hz, 5H), 1.37-1.26 (m, 1H), 1.06 (d, J=6.7 Hz, 3H). $^{13}$C NMR (100 MHz, CDCl$_3$) δ 148.2, 147.2, 128.8, 128.3 (q, J=294.2 Hz), 123.8, 64.4 (q, J=22.0 Hz), 60.9, 45.7, 33.8, 33.3, 33.2, 31.0, 29.2, 21.4, 14.1. $^{19}$F NMR (376 MHz, CDCl$_3$) δ −66.1 (s). IR (CHCl$_3$) ν cm$^{-1}$: 2972, 2869, 2362, 1607, 1521, 1347, 1136, 1056, 855, 763. HRMS (ESI/[M+H]+) Calculated for C$_{17}$H$_{25}$BrF$_3$N$_2$O$_3$: 441.1001. found 441.0993.

Following general procedure A1, the opposite enantiomer of amine 9Da was obtained from a reaction catalyzed by CD-21b (0.2 mol %) at −20° C. for 5 h. $^1$H and $^{19}$F NMR analysis of the crude umpolung reaction mixture showed 9/4>95/5, 9/10>95/5 and d.r.=92/8. The reaction was worked up following general procedure B1'. (+)-22Da was obtained as a light yellow liquid in 74% yield after flash chromatography (Hexanes/Et$_2$O=50/1 to 2/1) and 83% ee as determined by HPLC analysis. [α]D20=+11.9 (c=0.75, CHCl$_3$).

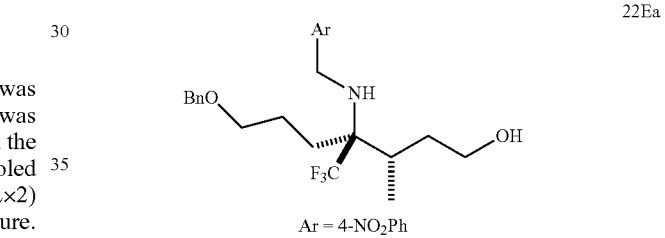

Aminoalcohol (−)-22Ea. Following general procedure A1, amine 9Ea was obtained from a reaction catalyzed by C-21b (0.2 mol %) at −20° C. for 7 h. $^1$H and $^{19}$F NMR analysis of the crude umpolung reaction mixture showed 9/4>95/5, 9/10>95/5 and d.r.=91/9. The reaction was worked up following general procedure B1. The amino-alcohol product (−)-22Ea was obtained as a light yellow liquid in 66% yield after flash chromatography (Hexanes/Et$_2$O=50/1 to 2/1) and 96% ee as determined by HPLC analysis [Daicel Chiralpak AD-H, Hexanes/IPA=95/5, 1.0 ml/min, α, 254 nm, t(major)=23.34 min, t(minor)=20.56 min]. [α]$_D^{20}$=−10.9 (c=1.08, CHCl$_3$). $^1$H NMR (400 MHz, CDCl$_3$) δ 8.16 (d, J=8.3 Hz, 2H), 7.53 (d, J=8.3 Hz, 2H), 7.38-7.26 (m, 5H), 4.48 (s, 2H), 4.00 (d, J=13.7 Hz, 1H), 3.85 (d, J=13.6 Hz, 1H), 3.81-3.74 (m, 1H), 3.62 (td, J=10.0, 4.8 Hz, 1H), 3.52-3.40 (m, 2H), 2.34-2.20 (m, 1H), 2.18-2.05 (m, 1H), 1.91-1.78 (m, 1H), 1.76-1.57 (m, 5H), 1.36-1.23 (m, 1H), 1.05 (d, J=6.6 Hz, 3H). $^{13}$C NMR (100 MHz, CDCl$_3$) δ 148.3, 147.2, 138.4, 128.8, 128.5, 128.3 (q, J$_{C-F}$=294.1 Hz), 127.8, 127.7, 123.7, 73.1, 70.4, 64.3 (q, J$_{C-F}$=21.8 Hz), 60.9, 45.7, 34.0, 31.2, 26.7, 23.2, 14.1. $^{19}$F NMR (376 MHz, CDCl$_3$) δ −66.3 (s). IR (CHCl$_3$) ν cm-1: 2957, 2875, 2362, 1606, 1521, 1346, 1136, 857, 740, 699. HRMS (ESI/[M+H]+) Calculated for C$_{23}$H$_{30}$F$_3$N$_2$O$_4$: 455.2158. found 455.2161.

Following general procedure A1, the opposite enantiomer of amine 9Ea was obtained from a reaction catalyzed by CD-21b (0.2 mol %) at −20° C. for 11 h. $^1$H and $^{19}$F NMR analysis of the crude umpolung reaction mixture showed 9/4>95/5, 9/10>95/5 and d.r.=91/9. The reaction was worked up following general procedure B1. (+)-22Ea was obtained as a light yellow liquid in 63% yield after flash chromatography (Hexanes/Et$_2$O=50/1 to 2/1) and 90% ee as determined by HPLC analysis. $[\alpha]_D^{20}$=+8.1 (c=1.21, CHCl$_3$).

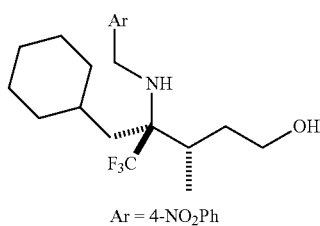

22Fa

Ar = 4-NO$_2$Ph

Aminoalcohol (−)-22Fa. Following general procedure A1, amine 9Fa was obtained from a reaction catalyzed by C-21b (0.2 mol %) at −20° C. for 12 h. $^1$H and $^{19}$F NMR analysis of the crude product from the umpolung reaction showed 9/4=91/9, 9/10>95/5 and d.r.=93/7. The reaction was worked up following general procedure B1. The amino-alcohol product (−)-22Fa was obtained as a white solid in 54% yield after flash chromatography (Hexanes/Et$_2$O=50/1 to 5/1) and 95% ee as determined by HPLC analysis [Daicel Chiralpak OJ-H, Hexanes/IPA=96.5/3.5, 1.0 ml/min, λ 254 nm, t(major)=20.31 min, t(minor)=17.33 min]. $[\alpha]_D^{20}$=−24.3 (c=1.19, CHCl$_3$). $^1$H NMR (400 MHz, CDCl$_3$) δ 8.17 (d, J=8.6 Hz, 2H), 7.55 (d, J=8.5 Hz, 2H), 4.02 (d, J=13.9 Hz, 1H), 3.86 (d, J=13.9 Hz, 1H), 3.79 (ddd, J=10.6, 6.4, 4.3 Hz, 1H), 3.63 (td, J=9.9, 5.2 Hz, 1H), 2.35-2.21 (m, 1H), 2.21-2.08 (m, 1H), 1.77 (d, J=12.2 Hz, 2H), 1.68 (bs, 2H), 1.67-1.58 (m, 3H), 1.57-1.39 (m, 2H), 1.34-1.18 (m, 3H), 1.18-1.08 (m, 1H), 1.08-0.93 (m, 5H). $^{13}$C NMR (100 MHz, CDCl$_3$) δ 148.5, 147.2, 128.6, 128.5 (q, J$_{C-F}$=294.4 Hz), 123.8, 65.3 (q, J$_{C-F}$=21.7 Hz), 61.1, 45.7, 37.2, 36.1, 35.5, 34.0, 32.3, 30.9, 26.6, 26.5, 26.2, 14.4. $^{19}$F NMR (376 MHz, CDCl$_3$) δ=−65.7 (s). IR (CHCl$_3$) ν 2929, 2853, 1606, 1520, 1480, 1449, 1345, 1215, 1165, 1136, 1054, 976, 885, 759 cm$^{-1}$. HRMS (ESI/[M+H]+) Calcd. for C$_{20}$H$_{24}$N$_2$O$_3$F$_3$ m/z 397.1739. found m/z 397.1739.

Following general procedure A1, the opposite enantiomer of amine 9Fa was obtained from a reaction catalyzed by CD-21b (0.2 mol %) at −20° C. for 12 h. $^1$H and $^{19}$F NMR analysis of the crude umpolung reaction mixture showed 9/4>95/5, 9/10>95/5 and d.r.=95/5. The reaction was worked up following general procedure B1. (+)-22Fa was obtained as a white solid in 50% yield after flash chromatography (Hexanes/Et$_2$O=50/1 to 5/1) and 80% ee determined by HPLC analysis. $[\alpha]_D^{20}$=+20.7 (c=1.01, CHCl$_3$).

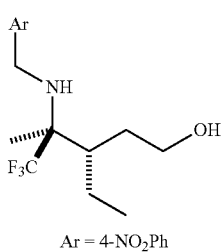

22Ab

Ar = 4-NO$_2$Ph

Aminoalcohol (+)-22Ab. Following general procedure A1, amine 9Ab was obtained from a reaction catalyzed by C-21b (0.2 mol %) at −20° C. for 5 h. $^1$H and $^{19}$F NMR analysis of the crude umpolung reaction mixture showed 9/4=89/11, 9/10>95/5 and d.r.>95/5. The reaction was worked up following general procedure B1. The amino-alcohol product (+)-22Ab was obtained as a colorless liquid in 64% yield after flash chromatography (Hexanes/Et$_2$O=50/1 to 5/1) and 95% ee as determined by HPLC analysis [Daicel Chiralpak AD-H, Hexanes/IPA=95/5, 1.0 ml/min, α, 254 nm, t(major)=17.90 min, t(minor)=15.98 min]. $[\alpha]_D^{20}$=+11.0 (c=1.23, CHCl$_3$). $^1$H NMR (400 MHz, CDCl$_3$) δ 8.16 (d, J=8.6 Hz, 2H), 7.54 (d, J=8.6 Hz, 2H), 4.03 (d, J=13.7 Hz, 1H), 3.92 (d, J=13.7 Hz, 1H), 3.84-3.74 (m, 1H), 3.61 (ddd, J=10.5, 8.7, 5.6 Hz, 1H), 2.16-1.90 (m, 3H), 1.86-1.70 (m, 2H), 1.55 (dt, J=12.1, 5.6 Hz, 1H), 1.30 (dt, J=18.4, 5.6 Hz, 1H), 1.25 (s, 3H), 1.00 (t, J=7.4 Hz, 3H). $^{13}$C NMR (100 MHz, CDCl$_3$) δ 148.0, 147.3, 128.8, 128.6 (q, J$_{C-F}$=291.9 Hz), 123.8, 62.90 (q, J$_{C-F}$=23.0 Hz), 62.07, 46.4, 39.8, 32.7, 23.2, 16.6, 13.1. $^{19}$F NMR (376 MHz, CDCl$_3$) δ=−70.9 (s); IR (CHCl$_3$) ν 3351, 2964, 2886, 1605, 1558, 1519, 1464, 1387, 1345, 1273, 1136, 1076, 1014, 849, 740 cm$^{-1}$. HRMS (ESI/[M+H]$^+$) Calcd. for C$_{15}$H$_{22}$N$_2$O$_3$F$_3$ m/z 335.1583. found m/z 335.1588.

Following general procedure A1, the opposite enantiomer of amine 9Ab was obtained from a reaction catalyzed by CD-21b (0.2 mol %) at −20° C. for 5 h. $^1$H and $^{19}$F NMR analysis of the crude umpolung reaction mixture showed 9/4=91/9, 9/10>95/5 and d.r.=95/5. The reaction was worked up following general procedure B1. (−)-22Ab was obtained as a colorless liquid in 61% yield after flash chromatography (Hexanes/Et$_2$O=50/1 to 5/1) and 83% ee as determined by HPLC analysis. $[\alpha]_D^{20}$=−8.6 (c=1.18, CHCl$_3$)

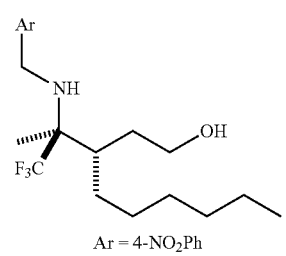

22Ac

Ar = 4-NO$_2$Ph

Aminoalcohol (+)-22Ac. Following general procedure A1, amine 9Ac was obtained from a reaction catalyzed by C-21b (0.2 mol %) at −20° C. for 12 h. $^1$H and $^{19}$F NMR analysis of the crude umpolung reaction mixture showed 9/4=86/14, 9/10>95/5 and d.r.>95/5. The reaction was worked up following general procedure B1. The amino-alcohol product (+)-22Ac was obtained as a light yellow liquid in 51% yield after flash chromatography (Hexanes/Et$_2$O=50/1 to 5/1) and 96% ee as determined by HPLC analysis [Daicel Chiralpak AD-H, Hexanes/IPA=95/5, 1.0 ml/min, α, 254 nm, t(major)=10.25 min, t(minor)=13.90 min]. $[\alpha]_D^{20}$=+15.6 (c=1.19, CHCl$_3$). $^1$H NMR (400 MHz, CDCl$_3$) δ 8.17 (d, J=8.7 Hz, 2H), 7.54 (d, J=8.6 Hz, 2H), 4.02 (d, J=13.7 Hz, 1H), 3.91 (d, J=13.7 Hz, 1H), 3.78 (ddd, J=11.2, 6.3, 5.3 Hz, 1H), 3.61 (ddd, J=10.5, 8.7, 5.6 Hz, 1H), 2.12-1.94 (m, 2H), 1.89 (td, J=7.6, 3.8 Hz, 1H), 1.74-1.59 (m, 1H), 1.52 (tt, J=12.3, 6.1 Hz, 1H), 1.38-1.17 (m, 13H), 0.89 (t, J=6.7 Hz, 3H). $^{13}$C NMR (100 MHz, CDCl$_3$) δ 148.0, 147.3, 128.8, 128.6 (q, J$_{C-F}$=291.9 Hz), 123.9, 62.9 (q, J$_{C-F}$=22.9 Hz), 62.0, 46.4, 38.3, 33.3, 31.9, 30.70, 29.8, 28.7, 22.8, 16.6, 14.2. $^{19}$F NMR (376 MHz, CDCl$_3$) δ=−70.8 (s); IR (CHCl$_3$) ν 2928, 2861, 1607, 1558, 1520, 1466, 1346, 1271, 1140, 1069, 1015, 860, 758 cm$^{-1}$. HRMS (ESI/[M+H]$^+$) Calcd. for C$_{19}$H$_{30}$N$_2$O$_3$F$_3$ m/z 391.2209. found m/z 391.2214.

Following general procedure A1, the opposite enantiomer of amine 9Ac was obtained from a reaction catalyzed by CD-21b (0.2 mol %) at −20° C. for 12 h. $^1$H and $^{19}$F NMR analysis of the crude umpolung reaction mixture showed 9/4=91/9, 9/10>95/5 and d.r.=95/5. The reaction was worked up following general procedure B1. (−)-22Ac was obtained as a light yellow liquid in 45% yield after flash chromatography (Hexanes/Et$_2$O=50/1 to 5/1) and 84% ee as determined by HPLC analysis. [α]$_D^{20}$=−11.9 (c=1.04, CHCl$_3$).

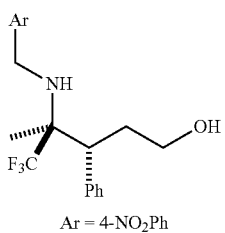

Ar = 4-NO$_2$Ph

22Ad

Aminoalcohol (−)-22Ad. Following general procedure A1, amine 9Ad was obtained from a reaction catalyzed by C-21b (0.2 mol %) at −20° C. for 8 h. $^1$H and $^{19}$F NMR analysis of the crude product from the umpolung reaction showed 9/4>95/5, 9/10=68/32 and d.r.>95/5. The reaction was worked up following general procedure B1. The amino-alcohol product (−)-22Ad was obtained as a white foam in 51% yield after flash chromatography (Hexanes/Et$_2$O=50/1 to 4/1) and 91% ee as determined by HPLC analysis [Daicel Chiralpak AD-H, Hexanes/IPA=95/5, 1.0 ml/min, λ 254 nm, t(major)=22.35 min, t(minor)=27.77 min]. [α]$_D^{20}$=−25.9 (c=1.25, CHCl$_3$). $^1$H NMR (400 MHz, CDCl$_3$) δ 8.18 (d, J=8.6 Hz, 2H), 7.56 (d, J=8.5 Hz, 2H), 7.38-7.25 (m, 5H), 4.07 (d, J=14.0 Hz, 1H), 3.97 (d, J=14.0 Hz, 1H), 3.51 (ddd, J=10.5, 6.5, 4.0 Hz, 1H), 3.26 (ddd, J=11.9, 7.5, 4.0 Hz, 2H), 2.43-2.27 (m, 1H), 2.05-1.91 (m, 1H), 1.55 (bs, 2H), 1.22 (s, 3H). $^{13}$C NMR (100 MHz, CDCl$_3$) δ 148.5, 147.2, 139.1, 128.8, 128.4, 128.3 (q, J$_{C-F}$=295.4 Hz), 127.4, 123.8, 62.6 (q, J$_{C-F}$=22.6 Hz), 60.8, 46.4, 45.4, 32.3, 17.8. $^{19}$F NMR (376 MHz, CDCl$_3$) δ=−71.4 (s). IR (CHCl$_3$) ν 3546, 3334, 1604, 1559, 1519, 1458, 1346, 1268, 1229, 1141, 1079, 1021, 946, 868, 705 cm$^{-1}$. HRMS (ESI/[M+H]$^+$) Calcd. for C$_{19}$H$_{22}$N$_2$O$_3$F$_3$ m/z 383.1583. found m/z 383.1584.

Following general procedure A1, the opposite enantiomer of amine 9Ad was obtained from a reaction catalyzed by CD-21b (0.2 mol %) at −20° C. for 8 h. $^1$H and $^{19}$F NMR analysis of the crude umpolung reaction mixture showed 9/4>95/5, 9/10=78/22 and d.r.>95/5. The reaction was worked up following general procedure B1. (+)-22Ad was obtained as a light yellow liquid in 53% yield after flash chromatography (Hexanes/Et$_2$O=50/1 to 4/1) and 61% ee as determined by HPLC analysis. [α]$_D^{20}$=+18.5 (c=1.24, CHCl$_3$).

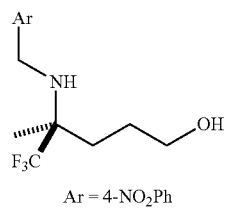

Ar = 4-NO$_2$Ph

22Ae

Aminoalcohol (+)-22Ae. Following general procedure A2, amine 9Ae was obtained from a reaction catalyzed by C-21b (0.2 mol %) at −10° C. for 3 h. $^1$H and $^{19}$F NMR analysis of the crude product from the umpolung reaction showed 9/4>95/5 and 9/10>95/5. The reaction was worked up following general procedure B1. The amino-alcohol product (+)-22Ae was obtained as a white foam in 89% yield after flash chromatography (CH$_2$Cl$_2$/MeOH=100/0 to 99/1) and 92% ee as determined by HPLC analysis [Daicel Chiralpak AD-H, Hexanes/IPA=97/3, 1.0 ml/min, λ 254 nm, t(major)=36.66 min, t(minor)=39.09 min]. [α]$_D^{20}$=+9.8 (c=1.08, CHCl$_3$). $^1$H NMR (400 MHz, CDCl$_3$) δ 8.19 (d, J=8.8 Hz, 2H), 7.53 (d, J=8.8 Hz, 2H), 3.97 (s, 2H), 3.69 (qdd, J=10.3, 6.3, 3.9 Hz, 2H), 1.86-1.66 (m, 4H), 1.56 (bs, 2H), 1.31 (s, 3H). $^{13}$C NMR (100 MHz, CDCl$_3$) δ 148.1, 147.3, 128.7, 128.40 (q, J$_{C-F}$=290.3 Hz), 127.0, 123.9, 63.0, 59.3 (q, J$_{C-F}$=24.2 Hz), 46.6, 30.1, 26.1, 18.8. $^{19}$F NMR (376 MHz, CDCl$_3$) δ=−77.2 (s). IR (CHCl$_3$) ν 3551, 2953, 2872, 1606, 1518, 1466, 1344, 1281, 1139, 1106, 1064, 1015, 847, 739 cm$^{-1}$. HRMS (ESI/[M+H]+) Calcd. for C$_{13}$H$_{18}$N$_2$O$_3$F$_3$ m/z 307.1270. found m/z 307.1269.

Following general procedure A2, the opposite enantiomer of amine 9Ae was obtained from a reaction catalyzed by CD-21b (0.2 mol %) at −10° C. for 3 h. $^1$H and $^{19}$F NMR analysis of the crude umpolung reaction mixture showed 9/4>95/5 and 9/10>95/5. The reaction was worked up following general procedure B1. (−)-22b was obtained as a white foam in 86% yield after flash chromatography (CH$_2$Cl$_2$/MeOH=100/0 to 99/1) and 85% ee as determined by HPLC analysis. [α]$_D^{20}$=−8.2 (c=0.95, CHCl$_3$).

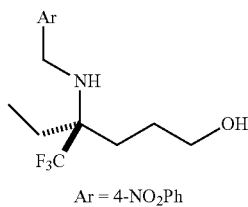

Ar = 4-NO$_2$Ph

22Be

Aminoalcohol (+)-22Be. Following general procedure A2, amine 9Be was obtained from a reaction catalyzed by C-21b (0.2 mol %) at −10° C. for 3 h. $^1$H and $^{19}$F NMR analysis of the crude umpolung reaction mixture showed 9/4>95/5 and 9/10>95/5. The reaction was worked up following general procedure B1. The amino-alcohol product (+)-22Be was obtained as a colorless liquid (52.0 mg, 82% yield) after flash chromatography (CH$_2$Cl$_2$/MeOH=100/0 to 99/1) and 91% ee as determined by HPLC analysis [Daicel Chiralpak AD-H, Hexanes/IPA=95/5, 1.0 ml/min, λ 254 nm, t(major)=19.52 min, t(minor)=20.08 min]. [α]$_D^{20}$+7.8 (c=1.05, CHCl$_3$). $^1$H NMR (400 MHz, CDCl$_3$) δ 8.18 (d, J=8.7 Hz, 2H), 7.54 (d, J=8.7 Hz, 2H), 3.95 (s, 2H), 3.75-3.59 (m, 2H), 1.88-1.65 (m, 6H), 1.58 (s, 3H), 1.00 (t, J=7.5 Hz, 3H). $^{13}$C NMR (100 MHz, CDCl$_3$) δ 148.4, 147.2, 128.6, 128.5 (q, $J_{C-F}$=291.7 Hz), 123.7, 62.9, 61.5 (q, $J_{C-F}$=23.0 Hz), 46.1, 28.0, 26.1, 24.7, 7.5. $^{19}$F NMR (376 MHz, CDCl$_3$) δ=−72.8 (s). IR (CHCl$_3$) ν 3362, 2969, 2884, 1606, 1518, 1460, 1344, 1234, 1136, 1061, 1015, 948, 851, 740, 697 cm$^{-1}$. HRMS (ESI/[M+H]$^+$) Calcd. for C$_{14}$H$_{20}$N$_2$O$_3$F$_3$ m/z 321.1426. found m/z 321.1419.

Following general procedure A2, the opposite enantiomer of amine 9Be was obtained from a reaction catalyzed by CD-21b (0.2 mol %) at −10° C. for 3 h. $^1$H and $^{19}$F NMR analysis of the crude umpolung reaction mixture showed 9/4>95/5 and 9/10>95/5. The reaction was worked up following general procedure B1. (−)-22Be was obtained as a colorless liquid in 88% yield after flash chromatography (CH$_2$Cl$_2$/MeOH=100/0 to 99/1) and 78% ee as determined by HPLC analysis. $[α]_D^{20}$=−5.8 (c=1.06, CHCl$_3$).

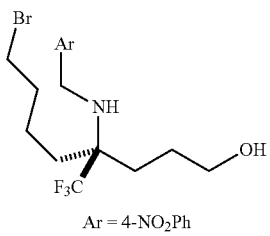

23De

Ar = 4-NO$_2$Ph

Aminoalcohol (−)-22De. Following general procedure A2, amine 9De was obtained from a reaction catalyzed by C-21b (0.2 mol %) at −10° C. for 3 h. $^1$H and $^{19}$F NMR analysis of the crude umpolung reaction mixture showed 9/4>95/5 and 9/10>95/5. The reaction was worked up following modified procedure B1'. The amino-alcohol product (−)-22De was obtained as a light yellow liquid in 84% yield after flash chromatography (Hexanes/Et$_2$O=50/1 to 2/1) and 91% ee as determined by HPLC analysis [Daicel Chiralpak OJ+OJ-H, Hexanes/IPA=99/1 for 3 min, then change to 90/10 gradually in 70 min and stay at 90/10, 1.0 ml/min, λ 254 nm, t(major)=111.43 min, t(minor)=106.42 min]. $[α]_D^{20}$=−2.0 (c=1.14, CHCl$_3$). $^1$H NMR (400 MHz, CDCl$_3$) δ 8.18 (d, J=8.7 Hz, 2H), 7.54 (d, J=8.6 Hz, 2H), 4.09-3.87 (m, 2H), 3.77-3.61 (m, 2H), 3.51-3.35 (m, 2H), 2.02-1.48 (m, 12H). $^{13}$C NMR (100 MHz, CDCl$_3$) δ 148.0, 147.2, 128.7, 128.3 (q, J=292.0 Hz), 123.7, 62.7, 61.5 (q, J=23.4 Hz), 46.1, 33.4, 32.9, 31.0, 28.5, 26.2, 21.4. $^{19}$F NMR (376 MHz, CDCl$_3$) δ−72.96. IR (CHCl$_3$) ν cm$^{-1}$: 2957, 2872, 2356, 1606, 1520, 1346, 1144, 1058, 857, 760. HRMS (ESI/[M+H]$^+$) Calculated for C$_{16}$H$_{23}$BrF$_3$N$_2$O$_3$: 427.0844. found 427.0849.

Following general procedure A1, the opposite enantiomer of amine 9De was obtained from a reaction catalyzed by CD-21De (0.2 mol %) at −10° C. for 3 h. $^1$H and $^{19}$F NMR analysis of the crude umpolung reaction mixture showed 9/4>95/5 and 9/10>95/5. The reaction was worked up following modified procedure B1'. (+)-22De was obtained as a light yellow liquid in 74% yield after flash chromatography (Hexanes/Et$_2$O=50/1 to 2/1) and 82% ee as determined by HPLC analysis. $[α]_D^{20}$=+0.4 (c=1.26, CHCl$_3$).

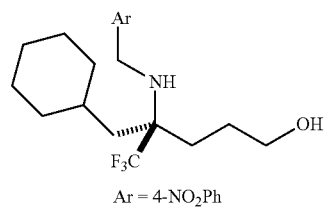

22Fe

Ar = 4-NO$_2$Ph

Aminoalcohol (+)-22Fe. Following general procedure A2, amine 9Fe was obtained from a reaction catalyzed by C-21b (0.2 mol %) at −10° C. for 3 h. $^1$H and $^{19}$F NMR analysis of the crude umpolung reaction mixture showed 9/4>95/5 and 9/10>95/5. The reaction was worked up following general procedure B1. The amino-alcohol product (+)-22Fe was obtained as a colorless liquid in 90% yield after flash chromatography (CH$_2$Cl$_2$/MeOH=100/0 to 99/1) and 92% ee as determined by HPLC analysis [Daicel Chiralpak AD-H, Hexanes/IPA=95/5, 1.0 ml/min, λ 254 nm, t(major)=12.83 min, t(minor)=15.54 min]. $[α]_D^{20}$=+0.2 (c=1.07, CHCl$_3$). $^1$H NMR (400 MHz, CDCl$_3$) δ 8.17 (d, J=8.6 Hz, 2H), 7.53 (d, J=8.6 Hz, 2H), 3.96 (s, 2H), 3.72-3.61 (m, 2H), 1.88-1.76 (m, 3H), 1.75-1.54 (m, 11H), 1.34-1.19 (m, 2H), 1.19-1.10 (m, 1H), 1.10-0.96 (m, 2H). $^{13}$C NMR (100 MHz, CDCl$_3$) δ 148.5, 147.2, 128.5, 128.4 (q, $J_{C-F}$=292.1 Hz), 123.8, 63.0, 62.2 (q, $J_{C-F}$=23.0 Hz), 46.3, 39.1, 35.7, 35.6, 32.5, 29.3, 26.6, 26.5, 26.2. $^{19}$F NMR (376 MHz, CDCl$_3$) δ=−72.6 (s). IR (CHCl$_3$) ν 3349, 2927, 2851, 1605, 1519, 1450, 1344, 1140, 1058, 971, 848, 754, 668 cm$^{-1}$. HRMS (ESI/[M+H]$^+$) Calcd. for C$_{19}$H$_{28}$N$_2$O$_3$F$_3$ m/z 389.2052. found m/z 389.2057.

Following general procedure A2, the opposite enantiomer of amine 9Fe was obtained from a reaction catalyzed by CD-21b (0.2 mol %) at −10° C. for 3 h. $^1$H and $^{19}$F NMR analysis of the crude umpolung reaction mixture showed 9/4>95/5 and 9/10>95/5. The reaction was worked up following general procedure B1. (−)-22Fe was obtained as a colorless liquid in 86% yield after flash chromatography (CH$_2$Cl$_2$/MeOH=100/0 to 99/1) and 82% ee as determined by HPLC analysis. $[α]_D^{20}$=−0.1 (c=1.03, CHCl$_3$).

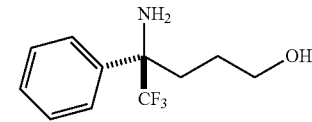

23Ge

Aminoalcohol (+)-23Ge. Following general procedure A2, amine 9Ge was obtained from a reaction catalyzed by C-21b (0.2 mol %) at −20° C. for 3 h. $^1$H and $^{19}$F NMR analysis of the crude umpolung reaction mixture showed 9/4=94/6 and 9/10>95/5. The reaction was worked up following general procedure B2. The amino-alcohol product (+)-23Ge was obtained as a white solid in 71% yield after flash chromatography (CH$_2$Cl$_2$/MeOH=100/0 to 98/2) and 94% ee as determined by HPLC analysis [Daicel Chiralpak AD-H, Hexanes/IPA=90/10, 1.0 ml/min, λ 210 nm, t(major)=8.00 min, t(minor)=10.53 min]. $[α]_D^{20}$=+14.6 (c=1.09, CHCl$_3$). $^1$H NMR (400 MHz, CDCl$_3$) δ 7.52 (d, J=7.8 Hz, 2H), 7.42-7.31 (m, 3H), 3.61-3.47 (m, 2H), 2.34 (ddd, J=14.4, 9.2, 5.4 Hz, 1H), 2.14 (bs, 2H), 1.95-1.83 (m, 1H), 1.58-1.44 (m, 1H), 1.40-1.23 (m, 1H). $^{13}$C NMR (100 MHz, CDCl$_3$) δ 136.6, 128.6, 128.3, 127.4 (q, $J_{C-F}$=285.6

Hz), 126.8 (q, $J_{C-F}$=1.6 Hz), 62.7, 61.6 (q, $J_{C-F}$=25.9 Hz), 32.9, 32.8, 26.4. $^{19}$F NMR (376 MHz, CDCl$_3$) δ=−79.0 (s). IR(CHCl$_3$) ν 3315, 2945, 1633, 1459, 1275, 1243, 1154, 1052, 1005, 929, 881, 762, 701, 676 cm$^{-1}$. HRMS (ESI/[M+H]+) Calcd. for C$_{11}$H$_{15}$NOF$_3$ m/z 234.1106. found m/z 234.1104.

Following general procedure A2, the opposite enantiomer of amine 9Ge was obtained from a reaction catalyzed by CD-21b (0.2 mol %) at −20° C. for 3 h. $^1$H and $^{19}$F NMR analysis of the crude umpolung reaction mixture showed 9/4=95/5 and 9/10>95/5. The reaction was worked up following general procedure B2. (−)-23Ge was obtained as a white solid in 61% yield after flash chromatography (CH$_2$Cl$_2$/MeOH=100/0 to 98/2) and 88% ee as determined by HPLC analysis. $[\alpha]_D^{20}$=−13.1 (c=1.22, CHCl$_3$).

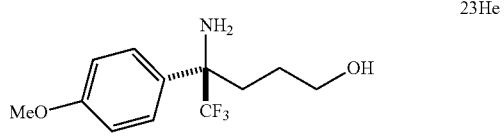

23He

Aminoalcohol (+)-23He. Following general procedure A2, amine 9He was obtained from a reaction catalyzed by C-21b (0.2 mol %) at −20° C. for 3 h. $^1$H and $^{19}$F NMR analysis of the crude umpolung reaction mixture showed 9/4=92/8 and 9/10>95/5. The reaction was worked up following general procedure B2. The amino-alcohol product (+)-23He was obtained as a colorless liquid in 67% yield after flash chromatography (CH$_2$Cl$_2$/MeOH=100/0 to 98/2) and 94% ee as determined by HPLC analysis [Daicel Chiralpak AD-H, Hexanes/IPA=90/10, 1.0 ml/min, λ 210 nm, t(major)=10.15 min, t(minor)=13.76 min]. $[\alpha]_D^{20}$=+9.3 (c=0.84, CHCl$_3$). $^1$H NMR (400 MHz, CDCl$_3$) δ 7.43 (d, J=8.7 Hz, 2H), 6.92 (d, J=8.9 Hz, 2H), 3.82 (s, 3H), 3.62-3.51 (m, 2H), 2.32 (ddd, J=14.4, 9.1, 5.5 Hz, 1H), 2.05 (bs, 2H), 1.93-1.82 (m, 1H), 1.57-1.46 (m, 1H), 1.38 (ddd, J=19.7, 12.5, 7.1 Hz, 1H). $^{13}$C NMR (100 MHz, CDCl$_3$) δ 159.4, 128.5, 128.1 (q, $J_{C-F}$=1.5 Hz), 127.5 (q, $J_{C-F}$=285.6 Hz), 113.9, 62.8, 61.2 (q, $J_{C-F}$=25.9 Hz), 55.4, 32.9, 26.4. $^{19}$F NMR (376 MHz, CDCl$_3$) δ=−79.4 (s). IR (CHCl$_3$) ν 3382, 2955, 2881, 1612, 1515, 1464, 1254, 1146, 1031, 946, 829, 760, 665 cm$^{-1}$. HRMS (ESI/[M+H]$^+$) Calcd. for C$_{12}$H$_{17}$NO$_2$F$_3$ m/z 264.1211. found m/z 264.1214.

Following general procedure A2, the opposite enantiomer of amine 9He was obtained from a reaction catalyzed by CD-21b (0.2 mol %) at −20° C. for 3 h. $^1$H and $^{19}$F NMR analysis of the crude umpolung reaction mixture showed 9/4=92/8 and 9/10>95/5. The reaction was worked up following general procedure B2. (−)-23He was obtained as a colorless liquid in 58% yield after flash chromatography (CH$_2$Cl$_2$/MeOH=100/0 to 98/2) and 87% ee as determined by HPLC analysis. $[\alpha]_D^{20}$=−7.9 (c=0.97, CHCl$_3$).

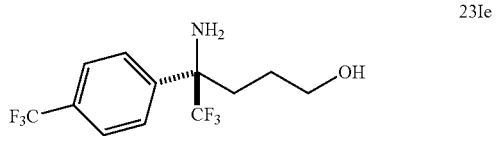

23Ie

Aminoalcohol (+)-23Ie. Following general procedure A2, amine 9Ie was obtained from a reaction catalyzed by C-21b (0.2 mol %) at −20° C. for 3 h. $^1$H and $^{19}$F NMR analysis of the crude umpolung reaction mixture showed 9/4=88/12 and 9/10>95/5. The reaction was worked up following general procedure B2. The amino-alcohol product (+)-23Ie was obtained as a colorless liquid in 78% yield after flash chromatography (CH2Cl2/MeOH=100/0 to 98/2) and 92% ee as determined by HPLC analysis [Daicel Chiralpak AD-H, Hexanes/IPA=90/10, 1.0 ml/min, α, 210 nm, t(major)=6.36 min, t(minor)=9.53 min]. $[\alpha]_D^{20}$+10.7 (c=1.07, CHCl$_3$). $^1$H NMR (400 MHz, CDCl$_3$) δ 7.69 (d, J=8.8 Hz, 2H), 7.65 (d, J=8.8 Hz, 2H), 3.66-3.43 (m, 2H), 2.39-2.26 (m, 1H), 2.23-1.78 (m, 3H), 1.60-1.45 (m, 1H), 1.31-1.17 (m, 1H). $^{13}$C NMR (100 MHz, CDCl$_3$) δ 141.0, 130.5 (q, $J_{C-F}$=32.7 Hz), 127.4 (q, $J_{C-F}$=1.7 Hz), 127.2 (q, $J_{C-F}$=285.6 Hz), 125.5 (q, $J_{C-F}$=3.7 Hz), 124.0 (q, $J_{C-F}$=272.2 Hz), 62.4, 61.8 (q, $J_{C-F}$=26.2 Hz), 32.7, 26.2. $^{19}$F NMR (376 MHz, CDCl$_3$) δ=−62.8 (s), −78.8 (s). IR (CHCl$_3$) ν 3341, 2960, 2880, 1623, 1519, 1460, 1415, 1326, 1240, 1161, 1115, 1070, 1018, 834, 759, 684 cm$^{-1}$. HRMS (ESI/[M+H]$^+$) Calcd. for C$_{12}$H$_{14}$NOF$_6$ m/z 302.0980. found m/z 302.0981.

Following general procedure A2, the opposite enantiomer of amine 9Ie was obtained from a reaction catalyzed by CD-21b (0.2 mol %) at −20° C. for 3 h. 1H and 19F NMR analysis of the crude umpolung reaction mixture showed 9/4=91/9 and 9/10>95/5. The reaction was worked up following general procedure B2. (−)-23Ie was obtained as a colorless liquid in 79% yield after flash chromatography (CH$_2$Cl$_2$/MeOH=100/0 to 98/2) and 85% ee as determined by HPLC analysis. $[\alpha]_D^{20}$=−12.0 (c=0.99, CHCl$_3$).

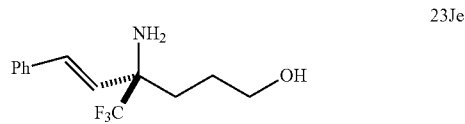

23Je

Aminoalcohol (+)-23Je. A modified procedure from A2 was followed. The solution of trifluoromethyl imine 1J (0.2 mmol) and catalyst C-21b (0.0004 mmol) in toluene (1.7 mL) was cooled to −20° C. KOH (50 wt % aq., 0.02 mmol, 2.2 µL) was added right after a solution of acrolein (0.4 mmol) in PhMe (0.3 mL) started being added with a syringe pump (0.3 mL/h). After the completion of the reaction, the mixture was passed through a small pad of deactivated silica (5 mm thick), which was washed with Et$_2$O (1 mL×3). The filtrates were combined, concentrated under vacuum to afford the crude amine 9Je as a yellow liquid. $^1$H and $^{19}$F NMR analysis of the crude umpolung reaction mixture showed 9/4=95/5 and 9/10>95/5. The reaction was worked up following general procedure B2. The amino-alcohol product (+)-23Je was obtained as a white solid in 90% yield after flash chromatography (CH$_2$Cl$_2$/MeOH=100/0 to 98/2) and 93% ee as determined by HPLC analysis [Daicel Chiralpak AD-H, Hexanes/IPA=95/5, 1.0 ml/min, α, 254 nm, t(major)=16.42 min, t(minor)=17.73 min]. $[\alpha]_D^{20}$=+84.5 (c=1.13, CHCl$_3$). $^1$H NMR (400 MHz, CDCl$_3$) δ 7.39 (d, J=7.4 Hz, 2H), 7.32 (t, J=7.4 Hz, 2H), 7.28-7.24 (m, 1H), 6.77 (d, J=16.2 Hz, 1H), 6.12 (d, J=16.2 Hz, 1H), 3.62 (tdd, J=10.9, 9.0, 5.3 Hz, 2H), 2.49 (bs, 1H), 1.99-1.88 (m, 1H), 1.78-1.67 (m, 3H), 1.67-1.56 (m, 2H). $^{13}$C NMR (100 MHz, CDCl$_3$) δ 136.0, 133.0, 128.8, 128.3, 127.3 (q, $J_{C-F}$=285.7 Hz), 126.8, 125.5, 62.8, 60.5 (q, $J_{C-F}$=25.8 Hz), 31.7, 26.4. $^{19}$F NMR (376 MHz, CDCl$_3$) δ=−81.1 (s). IR (CHCl$_3$) ν 3372, 2857, 1625, 1495, 1451, 1334, 1263, 1229, 1143, 1047, 991, 921, 817, 752 cm$^{-1}$. HRMS (ESI/[M+H]$^+$) Calcd. for C$_{13}$H$_{17}$NOF$_3$ m/z 260.1262. found m/z 260.1261.

The opposite enantiomer amine 9Je was obtained from a reaction catalyzed by CD-21b (0.2 mol %) at −20° C. for 1 h. $^1$H and $^{19}$F NMR analysis of the crude umpolung reaction mixture showed 9/4>95/5 and 9/10>95/5. The reaction was worked up following general procedure B2. (−)-23Je was obtained as a white solid in 62% yield after flash chromatography (CH$_2$Cl$_2$/MeOH=100/0 to 98/2) and 84% ee as determined by HPLC analysis. $[\alpha]_D^{20}=-70.5$ (c=1.06, CHCl$_3$).

Example 5: Catalytic Asymmetric Umpolung Reaction of Simple Imines

General Procedure for Asymmetric Umpolung Reaction of Simple Imines (Table 4 & 5)

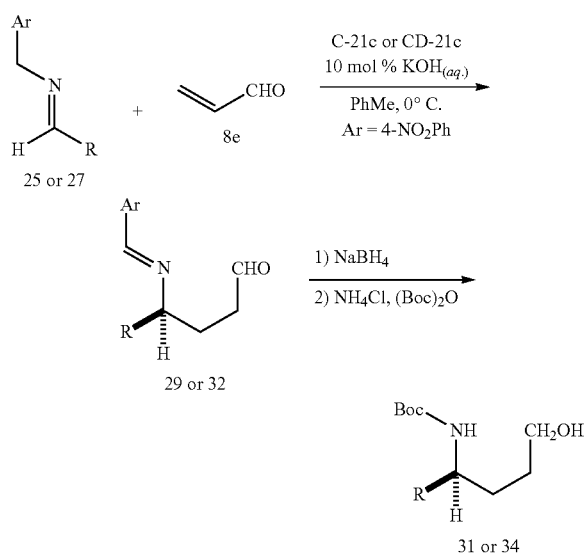

To an empty vial equipped with a Teflon-coated magnetic stir bar was charged with imine 25 or 27 (0.20 mmol) and C-21c or CD-21c (0.005 mmol, 4.8 mg). Then toluene (2.0 mL) was added to dissolve the solids into a clear solution by stirring for 5 min. After acrolein (0.40 mmol, 27 μL) was added to the mixture via a microsyringe, the reaction mixture was cooled to 0° C. and KOH (50 wt % aq., 0.02 mmol, 2.2 μL) was added. The immediately generated purple solution was vigorously stirred at 0° C. for the indicated time until the imine was completely consumed [monitored by $^1$H NMR analysis of an aliquot of the reaction mixture, at which stage the regioselectivity (29/30 or 32/33) was determined]. After the completion, the suspension was filtered through a short pad of Celite and the reaction vial was rinsed with CH$_2$Cl$_2$ three times (total about 4.0 mL). The combined organic solution was concentrated and dried to give crude 29 (aryl imines) or 32 (unsaturated imines) as a yellow oil.

The above crude amine 29 or 32 was dissolved in ethyl acetate (2.0 mL) and cooled to 0° C. Sodium borohydride (11.4 mg, 0.30 mmol) was then added in one portion. The reaction mixture was kept stirring at 0° C. for 30 min until the full consumption of aldehyde (monitored by $^1$H NMR). The suspension was then filtered and the reaction vial was rinsed with ethyl acetate three times (total 2.0 mL). The collected ethyl acetate solution (4.0 mL) was used for the next step directly.

To the above solution (4.0 mL) were added NH$_4$Cl (s, 2.0 g) and (Boc)$_2$O (218.0 mg, 1.0 mmol) at room temperature. After vigorously stirring for 30 min, the mixture was heated up to 75° C. for 36 h until the full conversion to 31 or 34 (monitored by $^1$H NMR). After the completion of the reaction, the mixture was cooled to room temperature, filtered and washed with ethyl acetate solution (about 10 mL). The combined organic solution was concentrated and residue was purified by flash chromatography on silica column chromatography to give N-Boc protected aminoalcohols 31 (aryl imines) or 34 (unsaturated imines).

Racemic 31 or 34 was Obtained from Achiral Phase Transfer Catalyst TBAB Catalyzed Reactions or Simply from Mixing the Products from C-21c and CD-21c Catalyzed Reactions

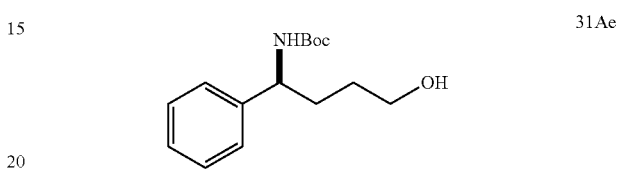

(−)-31Ae was obtained as a white solid in 55% yield after flash chromatography (Hexanes/ethyl acetate=20/1 to 2/1) and 93% ee from a reaction catalyzed by C-21c (2.5 mol %) in PhMe (0.1 M) at 0° C. for 8 h. The ee was determined by HPLC analysis [Chiralpak, AS-H, Hexanes/IPA=95/5, 1.0 mL/min, λ 220 nm, t(minor)=13.03 min, t(major)=14.80 min]. $[\alpha]_D^{20}=-42.2$ (c=0.41, CHCl$_3$). $^1$H NMR (400 MHz, CDCl$_3$) δ 7.48-7.04 (m, 5H), 4.89 (br, s, 1H), 4.65 (br, s, 1H), 3.79-3.48 (m, 2H), 2.06-1.72 (m, 2H), 1.71-1.47 (m, 2H), 1.41 (s, 9H). $^{13}$C NMR (100 MHz, CDCl$_3$) δ 155.4, 142.6, 128.6, 127.3, 126.4, 79.5, 62.4, 54.7, 33.3, 29.2, 28.4. IR (CHCl$_3$) ν 3336, 2975, 2941, 1694, 1502, 1451, 1389, 1367, 1249, 1219, 1170, 1056, 768, 701. HRMS (ESI/[M+Na]$^+$) Calcd. for C$_{15}$H$_{23}$NNaO$_3$ m/z 288.1576. found m/z 288.1574.

(+)-31Ae: 52% yield and 89% ee from a reaction catalyzed by CD-21c (2.5 mol %) in PhMe (0.1 M) at 0° C. for 8 h. $[\alpha]_D^{20}=+37.7$ (c=0.30, CHCl$_3$).

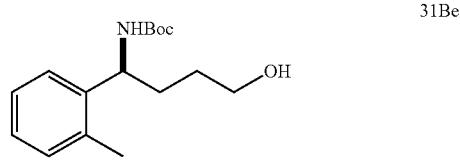 [SMILES: Cc1ccccc1[C@H](CCCO)NC(=O)OC(C)(C)C]

(−)-31Be was obtained as a white solid in 51% yield after flash chromatography (Hexanes/ethyl acetate=20/1 to 2/1) and 94% ee from a reaction catalyzed by C-21c (2.5 mol %) in toluene (0.1M) at 0° C. for 8 h. The ee was determined by HPLC analysis [Chiralpak, AS-H, Hexanes/IPA=93/7, 1.0 mL/min, λ 220 nm, t(minor)=7.47 min, t(major)=10.36 min]. $[\alpha]_D^{20}=-43.6$ (c=0.70, CHCl$_3$). $^1$H NMR (400 MHz, CDCl$_3$) δ 7.25-6.96 (m, 4H), 5.10-4.58 (m, 2H), 3.74-3.53 (m, 2H), 2.38 (s, 3H), 1.98-1.71 (m, 2H), 1.71-1.51 (m, 2H), 1.41 (s, 9H). $^{13}$C NMR (100 MHz, CDCl$_3$) δ 155.4, 140.8, 135.7, 130.7, 127.0, 126.3, 124.7, 79.39, 62.5, 50.5, 32.8, 29.2, 28.4, 19.3. IR (CHCl$_3$) ν 3362, 2973, 2937, 2874, 1693, 1516, 1499, 1455, 1388, 1367, 1249, 1170, 1056, 868, 762. HRMS (ESI/[M+Na]$^+$) Calcd. for C$_{16}$H$_{25}$NNaO$_3$ m/z 302.1732. found m/z 302.1735.

(+)-31Be: 48% yield and 87% ee from a reaction catalyzed by CD-21c (2.5 mol %) in toluene (0.1M) at 0° C. for 8 h. $[\alpha]_D^{20}=+38.3$ (c=0.70, CHCl$_3$).

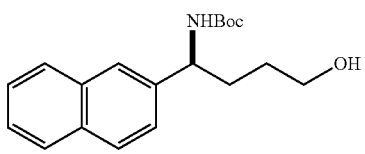
31Ce (−)-31Ce was obtained as a white solid in 54% yield after flash chromatography (Hexanes/ethyl acetate=20/1 to 2/1) and 94% ee from a reaction catalyzed by C-21c (2.5 mol %) in toluene/CH$_2$Cl$_2$ (2:1, 0.067 M) at 0° C. for 8 h. The ee was determined by HPLC analysis [Chiralpak, AS-H, Hexanes/IPA=95/5, 1.0 mL/min, λ 220 nm, t(minor)=18.70 min, t(major)=21.25 min]. $[\alpha]_D^{20}$=−46.0 (c=0.60, CHCl$_3$). $^1$H NMR (400 MHz, CDCl$_3$) δ 7.92-7.75 (m, 3H), 7.71 (s, 1H), 7.54-7.42 (m, 2H), 7.39 (d, J=8.2 Hz, 1H), 5.05 (d, J 7.9 Hz, 1H), 4.81 (br, s, 1H), 3.65 (q, J 5.6 Hz, 2H), 2.13-1.72 (m, 2H), 1.71-1.47 (m, 2H), 1.42 (s, 9H). $^{13}$C NMR (100 MHz, CDCl$_3$) δ 155.4, 140.0, 133.3, 132.7, 128.4, 127.8, 127.6, 126.1, 125.7, 125.01, 124.5, 79.6, 62.3, 54.8, 33.1, 29.2, 28.4. IR (CHCl$_3$) ν 3334, 3008, 2974, 2937, 2872, 1692, 1509, 1389, 1368, 1249, 1169, 1056, 858, 820, 756, 665. HRMS (ESI/[M+Na]$^+$) Calcd. for C$_{19}$H$_{25}$NNaO$_3$ m/z 338.1732. found m/z 338.1727.

(+)-31Ce: 53% yield and 87% ee from a reaction catalyzed by CD-21c (2.5 mol %) in toluene/CH$_2$Cl$_2$ (2:1, 0.067 M) at 0° C. for 16 h; $[\alpha]_D^{20}$=+45.8 (c=0.80, CHCl$_3$).

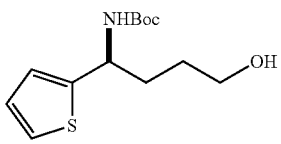
31De (−)-31De was obtained as a white solid in 53% yield after flash chromatography (Hexanes/ethyl acetate=20/1 to 2/1) and 95% ee from a reaction catalyzed by C-21c (2.5 mol %) in toluene (0.1M) at 0° C. for 8 h. The ee was determined by HPLC analysis [Chiralpak, AS-H, Hexanes/IPA=95/5, 1.0 mL/min, λ 220 nm, t(minor)=16.21 min, t(major)=18.06 min]. $[\alpha]_D^{20}$=−50.6 (c=0.88, CHCl$_3$). $^1$H NMR (400 MHz, CDCl$_3$) δ 7.23-7.14 (m, 1H), 6.94 (m, 2H), 4.96 (br, s, 1H) 4.85 (br, s, 1H), 3.68 (m, 2H), 2.11-1.83 (m, 2H), 1.83-1.51 (m, 2H), 1.44 (s, 9H). $^{13}$C NMR (100 MHz, CDCl$_3$) δ 155.2, 146.6, 126.8, 124.0, 79.7, 62.3, 50.2, 33.7, 29.1, 28.4. IR (CHCl$_3$) ν 3366, 2975, 2938, 2873, 1693, 1519, 1449, 1388, 1368, 1248, 1170, 1065, 1025, 856, 759, 701. HRMS (TOP[M+Na]$^+$) Calcd. for C$_{13}$H$_{21}$NNaO$_3$S m/z 294.1140. found m/z 294.1136.

(+)-31De: 47% yield and 90% ee from a reaction catalyzed by CD-21c (2.5 mol %) in toluene (0.1M) at 0° C. for 8 h; $[\alpha]_D^{20}$+49.7 (c=0.76, CHCl$_3$).

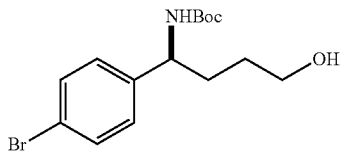
31Ee (−)-31Ee was obtained as a white solid in 52% yield after flash chromatography (Hexanes/ethyl acetate=20/1 to 2/1) and 95% ee from a reaction catalyzed by C-21c (2.5 mol %) in toluene/CH$_2$Cl$_2$ (2:1, 0.067 M) at 0° C. for 5 h. The ee was determined by HPLC analysis [Chiralpak, AS-H, Hexanes/IPA=95/5, 1.0 mL/min, α, 220 nm, t(minor)=14.02 min, t(major)=15.61 min]. $[\alpha]_D^{20}$=−34.1 (c=0.61, CHCl$_3$). $^1$H NMR (400 MHz, CDCl$_3$) δ 7.45 (d, J=8.3 Hz, 2H), 7.15 (d, J=8.0 Hz, 2H), 4.90 (br, s, 1H), 4.60 (br, s, 1H), 3.83-3.47 (m, 2H), 2.02-1.69 (m, 2H), 1.68-1.47 (m, 2H), 1.40 (s, 9H). $^{13}$C NMR (100 MHz, CDCl$_3$) δ 155.3, 141.9, 131.6, 128.1, 120.94, 79.7, 62.2, 54.1, 33.1, 29.0, 28.3; IR (CHCl$_3$) ν 3346, 2974, 2941, 1690, 1523, 1491, 1388, 1367, 1250, 1169, 1068, 1011, 767. HRMS (ESI/[M+Na]+) Calcd. for C$_{15}$H$_{22}$BrNNaO$_3$ m/z 366.0681. found m/z 366.0678.

(+)-31Ee: 48% yield and 89% ee from a reaction catalyzed by CD-21c (2.5 mol %) in toluene/CH$_2$Cl$_2$ (2:1, 0.067 M) at 0° C. for 5 h; $[\alpha]_D^{20}$=+36.9 (c=0.75, CHCl$_3$).

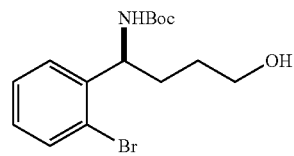
31Fe (−)-31Fe was obtained as a white solid in 56% yield after flash chromatography (Hexanes/ethyl acetate=20/1 to 2/1) and 95% ee from a reaction catalyzed by C-21c (2.5 mol %) in toluene (0.1M) at 0° C. for 5 h. The ee was determined by HPLC analysis [Chiralpak, AS-H, Hexanes/IPA=90/10, 1.0 mL/min, λ 220 nm, t(minor)=7.62 min, t(major)=9.65 min]. $[\alpha]_D^{20}$=−0.90 (c=0.90, CHCl$_3$). $^1$H NMR (400 MHz, CDCl$_3$) δ 7.53 (d, J=7.9 Hz, 1H), 7.39-7.19 (m, 2H), 7.17-6.99 (m, 1H), 5.57-4.57 (m, 2H), 3.81-3.49 (m, 2H), 2.05-1.52 (m, 4H), 1.34 (s, 9H). $^{13}$C NMR (100 MHz, CDCl$_3$) δ 155.1, 142.0, 133.3, 128.5, 127.6, 127.2, 122.9, 79.6, 62.2, 54.1, 32.3, 29.1, 28.3. IR (CHCl$_3$) ν 3337, 3007, 2975, 2938, 2873, 1695, 1522, 1506, 1474, 1443, 1387, 1368, 1250, 1170, 1054, 1025, 759. HRMS (ESI/[M+Na]$^+$) Calcd. for C$_{15}$H$_{22}$BrNNaO$_3$ m/z 366.0681. found m/z 366.0684.

(+)-31Fe: 51% yield and 92% ee from a reaction catalyzed by CD-21c (2.5 mol %) in toluene (0.1M) at 0° C. for 5 h; $[\alpha]_D^{20}$+1.0 (c=0.80, CHCl$_3$).

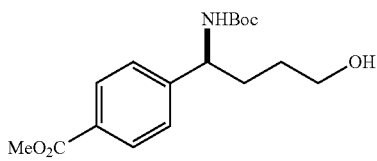
31Ge (−)-31Ge was obtained as a white solid in 53% yield after flash chromatography (Hexanes/ethyl acetate=20/1 to 2/1) and 95% ee from a reaction catalyzed by C-21c (2.5 mol %) in toluene/CH$_2$Cl$_2$ (2:1, 0.067M) at 0° C. for 8 h. The ee was determined by HPLC analysis [Chiralpak, AS-H, Hexanes/IPA=95/5, 1.0 mL/min, λ 220 nm, t(minor)=26.42 min, t(major)=31.04 min]. $[\alpha]_D^{20}$=−29.9 (c=0.90, CHCl$_3$). $^1$H NMR (400 MHz, CDCl$_3$) δ 7.99 (d, J=8.2 Hz, 2H), 7.34 (d, J=8.0 Hz, 2H), 5.03 (d, J=6.9 Hz, 1H), 4.69 (br, s, 1H), 3.90 (s, 3H), 3.65 (t, J=6.2 Hz, 2H), 1.95-1.45 (m, 4H), 1.40 (s, 9H). NMR (100 MHz, CDCl$_3$) δ 166.9, 155.3, 148.1, 129.9, 129.0, 126.3, 79.8, 62.2, 54.5, 52.1, 33.2, 29.0, 28.3. IR (CHCl$_3$) ν 3347, 3008, 2950, 2876, 1704, 1611, 1521, 1440, 1388, 1365, 1284, 1251, 1219, 1171, 1113, 1058, 1021, 860, 769, 709. HRMS (ESI/[M+Na]$^+$) Calcd. for C$_{17}$H$_{25}$NNaO$_5$ m/z 346.1630. found m/z 346.1623.

(+)-31Ge: 50% yield and 85% ee from a reaction catalyzed by CD-21c (2.5 mol %) in toluene/CH$_2$Cl$_2$ (2:1, 0.067M) at 0° C. for 8 h; CD-21c: [α]$_D^{20}$=+24.6 (c=0.54, CHCl$_3$).

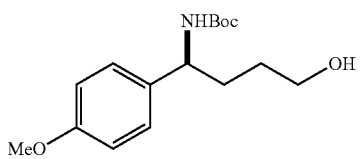

31He (−)-31He was obtained as a white solid in 45% yield after flash chromatography (Hexanes/ethyl acetate=20/1 to 2/1) and 95% ee from a reaction catalyzed by C-21c (5.0 mol %) in toluene (0.1M) at 0° C. for 18 h. The ee was determined by HPLC analysis [Chiralpak, AS-H, Hexanes/IPA=95/5, 1.0 mL/min, λ 220 nm, t(minor)=13.80 min, t(major)=17.91 min]. [α]$_D^{20}$=−37.8 (c=0.46, CHCl$_3$). $^1$H NMR (400 MHz, CDCl$_3$) δ 7.19 (d, J=8.3 Hz, 2H), 6.86 (d, J=8.5 Hz, 2H), 4.81 (br, s, 1H), 4.59 (br, s, 1H), 3.79 (s, 3H), 3.65 (t, J=6.1 Hz, 2H), 2.08-1.66 (m, 2H), 1.70-1.46 (m, 2H), 1.41 (s, 9H). $^{13}$C NMR (100 MHz, CDCl$_3$) δ 158.7, 155.4, 134.7, 127.5, 114.0, 79.4, 62.4, 55.3, 54.1, 33.2, 29.2, 28.4; IR (CHCl$_3$) ν 3371, 3004, 2971, 2936, 1690, 1612, 1514, 1452, 1367, 1297, 1247, 1172, 1037, 832, 763. HRMS (ESI/[M+Na]$^+$) Calcd. for C$_{16}$H$_{25}$NNaO$_4$ m/z 318.1681. found m/z 318.1678.

(+)-31He: 41% yield and 87% ee from a reaction catalyzed by CD-21c (5.0 mol %) in toluene (0.1M) at 0° C. for 18 h; [α]$_D^{20}$+36.1 (c=0.75, CHCl$_3$).

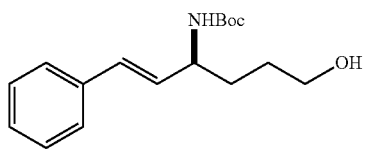

34Ae (−)-34Ae was obtained as a white solid in 51% yield after flash chromatography (Hexanes/ethyl acetate=20/1 to 2/1) and 92% ee from a reaction catalyzed by C-21c (2.5 mol %) in toluene (0.1M) at 0° C. for 16 h. The ee was determined by HPLC analysis [Chiralpak, AS-H, Hexanes/IPA=95/5, 1.0 mL/min, λ 220 nm, t(minor)=15.18 min, t(major)=20.57 min]. [α]$_D^{20}$=−34.6 (c=0.80, CHCl$_3$). $^1$H NMR (400 MHz, CDCl$_3$) δ 7.58-7.03 (m, 5H), 6.52 (d, J=15.9 Hz, 1H), 6.09 (dd, J=15.9, 6.4 Hz, 1H), 4.60 (br, s, 1H), 4.29 (br, s, 1H), 3.69 (m, 2H), 1.67 (m, 4H), 1.45 (s, 9H). $^{13}$C NMR (100 MHz, CDCl$_3$) δ 155.5, 136.7, 130.3, 128.5, 127.5, 126.4, 79.5, 62.5, 52.2, 32.0, 28.8, 28.4. IR (CHCl$_3$) ν 3345, 2975, 2937, 1691, 1519, 1510, 1450, 1390, 1367, 1248, 1170, 1058, 969, 769, 696. HRMS (ESI/[M+Na]$^+$) Calcd. for C$_{17}$H$_{25}$NNaO$_3$ m/z 314.1732. found m/z 314.1731.

(+)-34Ae: 47% yield and 86% ee from a reaction catalyzed by CD-21c (2.5 mol %) in toluene (0.1M) at 0° C. for 18 h; [α]$_D^{20}$=+32.0 (c=0.65, CHCl$_3$).

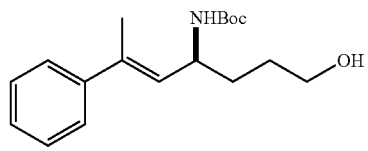

34Be (−)-34Be was obtained as a white solid in 50% yield after flash chromatography (Hexanes/ethyl acetate=20/1 to 2/1) and 92% ee from a reaction catalyzed by C-21c (2.5 mol %) in toluene (0.1M) at 0° C. for 16 h. The ee was determined by HPLC analysis [Chiralpak, AS-H, Hexanes/IPA=97/3, 1.0 mL/min, λ 220 nm, t(minor)=18.04 min, t(major)=28.19 min]. [α]$_D^{20}$=−37.1 (c=0.87, CHCl$_3$). $^1$H NMR (400 MHz, CDCl$_3$) δ 7.12-7.40 (m, 5H), 5.47 (d, J=8.7 Hz, 1H), 4.47 (m, 2H), 3.62 (t, J=5.9 Hz, 2H), 2.05 (s, 3H), 1.44-1.86 (m, 4H), 1.38 (s, 9H). $^{13}$C NMR (100 MHz, CDCl$_3$) δ 155.4, 143.0, 137.8, 128.6, 128.2, 127.2, 125.8, 79.4, 62.6, 49.1, 32.8, 28.7, 28.1, 16.4. IR (CHCl$_3$) ν 3348, 2975, 2936, 2873, 1691, 1520, 1501, 1448, 1387, 1368, 1246, 1220, 1170, 1058, 1020, 767, 698. HRMS (ESI/[M+Na]$^+$) Calcd. for C$_{18}$H$_{27}$NNaO$_3$ m/z 328.1889. found m/z 328.1887.

(+)-34Be: 45% yield and 86% ee from a reaction catalyzed by CD-21c (2.5 mol %) in toluene (0.1M) at 0° C. for 16 h; [α]$_D^{20}$=+32.3 (c=0.86, CHCl$_3$).

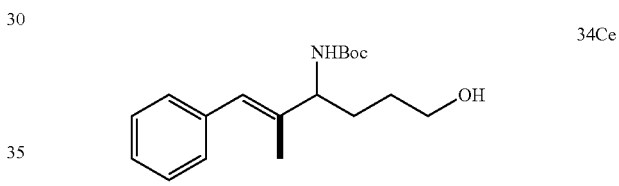

34Ce (−)-34Ce was obtained as a white solid in 46% yield after flash chromatography (Hexanes/ethyl acetate=20/1 to 2/1) and 95% ee from a reaction catalyzed by C-21c (2.5 mol %) in toluene (0.1M) at 0° C. for 24 h. The ee was determined by HPLC analysis [Chiralpak, AS-H, Hexanes/IPA=97/3, 1.0 mL/min, λ 220 nm, t(minor)=14.98 min, t(major)=22.86 min]. [α]$_D^{20}$=−14.2 (c=0.90, CHCl$_3$). $^1$H NMR (400 MHz, CDCl$_3$) δ 7.31-7.20 (m, 2H), 7.20-7.04 7.15 (m, 3H), 6.37 (s, 1H), 4.65 (br, s, 1H), 4.08 (br, s, 1H), 3.62 (br, s, 2H), 1.76 (s, 3H), 1.73-1.44 (m, 4H), 1.38 (s, 9H). $^{13}$C NMR (100 MHz, CDCl$_3$) δ 161.9, 155.5, 137.7, 128.9, 128.0, 126.3, 125.9, 79.4, 62.4, 57.7, 30.1, 29.2, 28.4, 14.5. IR (CHCl$_3$) ν 3359, 3019, 2973, 1694, 1500, 1448, 1387, 1368, 1247, 1219, 1170, 1060, 1004, 866, 769, 700. HRMS (ESI/[M+Na]$^+$) Calcd. for C$_{18}$H$_{27}$NNaO$_3$ m/z 328.1889. found m/z 328.1883.

(+)-34Ce: 43% yield and 92% ee from a reaction catalyzed by CD-21c (2.5 mol %) in toluene (0.1M) at 0° C. for 24 h; [α]$_D^{20}$=+11.3 (c=0.90, CHCl$_3$).

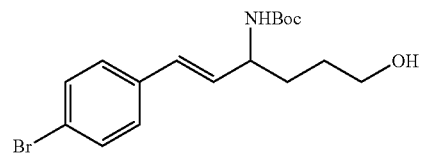

34De (−)-34De was obtained as a white solid in 44% yield after flash chromatography (Hexanes/ethyl acetate=20/1 to 2/1) and 92% ee from a reaction catalyzed by C-21c (2.5 mol %) in toluene (0.1M) at 0° C. for 12 h. The ee was determined by HPLC analysis [Chiralpak, AS-H, Hexanes/IPA=95/5, 1.0 mL/min, λ 220 nm, t(minor)=18.48 min, t(major)=22.99 min]. $[\alpha]_D^{20}$=−23.6 (c=0.90, CHCl$_3$). $^1$H NMR (400 MHz, CDCl$_3$) δ 7.42 (d, J=8.3 Hz, 2H), 7.21 (d, J=8.4 Hz, 2H), 6.45 (d, J=15.9 Hz, 1H), 6.08 (dd, J=15.9, 6.3 Hz, 1H), 4.63 (br.s, 1H), 4.29 (br, s, 1H), 3.69 (t, J=5.0 Hz, 2H), 1.67 (m, 4H), 1.45 (s, 9H). $^{13}$C NMR (100 MHz, CDCl$_3$) δ 155.4, 135.6, 131.6, 131.2, 129.1, 127.9, 121.3, 79.6, 62.4, 52.2, 31.9, 28.8, 28.4. IR (CHCl$_3$) ν 3347, 2972, 2937, 1690, 1519, 1492, 1449, 1393, 1365, 1248, 1220, 1170, 1058, 1010, 970, 856, 769. HRMS (ESI/[M+Na]$^+$) Calcd. for C$_{17}$H$_{24}$BrNNaO$_3$ m/z 392.0837. found m/z 392.0834.

(+)-34De: 40% yield and 85% ee from a reaction catalyzed by CD-21c (2.5 mol %) in toluene (0.1M) at 0° C. for 12 h; $[\alpha]_D^{20}$=+29.2 (c=0.54, CHCl$_3$).

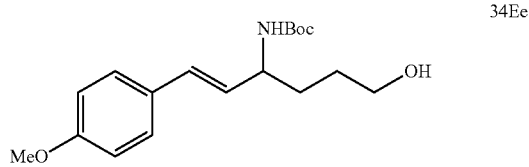 [SMILES: COc1ccc(/C=C/C(CCCO)NC(=O)OC(C)(C)C)cc1]

34Ee (−)-34Ee was obtained as a white solid in 41% yield after flash chromatography (Hexanes/ethyl acetate=20/1 to 2/1) and 90% ee from a reaction catalyzed by C-21c (5.0 mol %) in toluene (0.1M) at 0° C. for 24 h. The ee was determined by HPLC analysis [Chiralpak, AS-H, Hexanes/IPA=97/3, 1.0 mL/min, λ 220 nm, t(minor)=16.30 min, t(major)=20.14 min]. $[\alpha]_D^{20}$=−28.8 (c=0.76, CHCl$_3$). $^1$H NMR (400 MHz, CDCl$_3$) δ 7.28 (d, J=8.7 Hz, 2H), 6.84 (d, J=8.7 Hz, 2H), 6.46 (d, J=15.9 Hz, 1H), 5.94 (dd, J=6.6, 15.9 Hz, 1H), 4.60 (br, s, 1H), 4.27 (br, s, 1H), 3.80 (s, 3H), 3.69 (m, 2H), 1.66 (m, 4H), 1.45 (s, 9H). $^{13}$C NMR (100 MHz, CDCl$_3$) δ 159.1, 155.4, 129.8, 129.5, 128.0, 127.5, 114.0, 79.5, 62.5, 55.3, 52.3, 32.1, 28.8, 28.4; IR (CHCl$_3$) ν 3336, 3008, 2973, 2938, 1692, 1607, 1513, 1390, 1365, 1348, 1249, 1220, 1170, 1058, 969, 769. HRMS (ESI/[M+Na]$^+$) Calcd. for C$_{18}$H$_{27}$NNaO$_4$ m/z 344.1838. found m/z 344.1834.

(+)-34Ee: 38% yield and 85% ee from a reaction catalyzed by CD-21c (5.0 mol %) in toluene (0.1M) at 0° C. for 36 h; $[\alpha]_D^{20}$=+23.8 (c=0.45, CHCl$_3$).

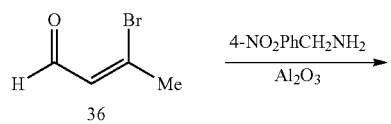

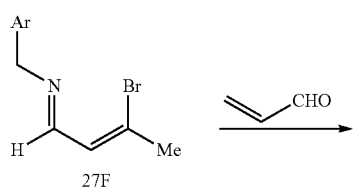

27F

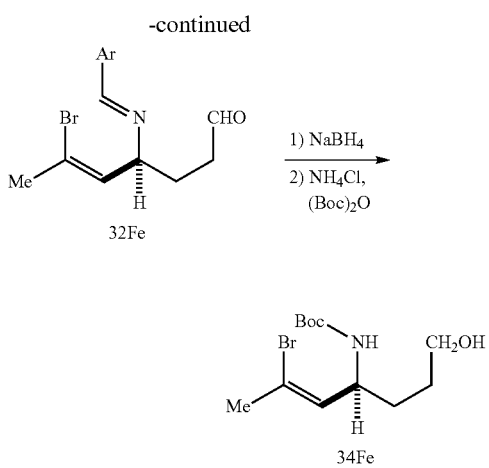

(−)-34Fe was obtained as a white solid in 37% yield (overall yield for a four-step transformation of 36 to 34Fe) after flash chromatography (Hexanes/ethyl acetate=20/1 to 2/1) and 90% ee from a reaction catalyzed by C-21c (5.0 mol %) in toluene (0.1M) at 0° C. for 6 h. The ee was determined by HPLC analysis [Chiralpak, AD-H, Hexanes/IPA=97/3, 1.0 mL/min, λ 220 nm, t(minor)=11.00 min, t(major)=18.69 min]. $[\alpha]_D^{20}$=−34.4 (c=0.73, CHCl$_3$). $^1$H NMR (400 MHz, CDCl$_3$) δ 5.67 (dq, J=9.4, 1.3 Hz, 1H), 4.56 (br, s, 1H), 4.17 (br, s, 1H), 3.66 (t, J=5.4 Hz, H), 2.32 (s, 3H), 1.94-1.46 (m, 4H), 1.43 (s, 9H). $^{13}$C NMR (100 MHz, CDCl$_3$) δ 155.1, 132.7, 123.4, 79.6, 62.3, 49.6, 32.18, 28.5, 28.3, 24.0; IR (CHCl$_3$) ν 3334, 2974, 2934, 1692, 1522, 1385, 1369, 1311, 1249, 1219, 1170, 1058, 1012, 771, 667. HRMS (ESI/[M+Na]$^+$) Calcd. for C$_{12}$H$_{22}$BrNNaO$_3$ m/z 330.0681. found m/z 330.0680.

(+)-34Fe: 32% yield and 80% ee from a reaction catalyzed by CD-21c (5.0 mol %) in toluene (0.1M) at 0° C. for 6 h; $[\alpha]_D^{20}$=+28.8 (c=0.40, CHCl$_3$).

Example 6: Gram Scale Umpolung Reaction of Imine 1A with Crotonaldehyde 8a

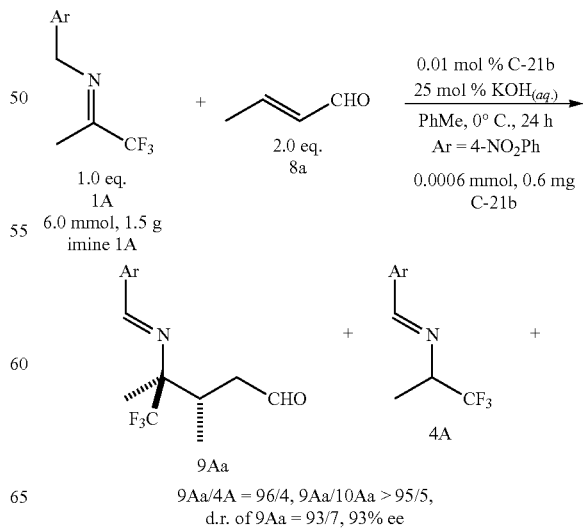

9Aa/4A = 96/4, 9Aa/10Aa > 95/5, d.r. of 9Aa = 93/7, 93% ee

-continued

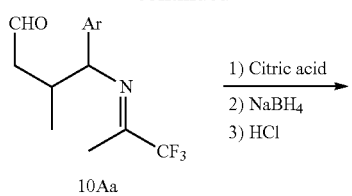

10Aa

1) Citric acid
2) NaBH₄
3) HCl

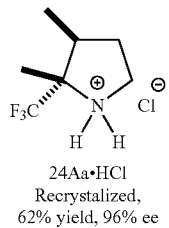

24Aa·HCl
Recrystalized,
62% yield, 96% ee

At 0° C., to the solution of imine 1A (1.5 g, 6.0 mmol), aldehyde 8a (1.0 mL, 12.0 mmol) and catalyst C-21b (0.6 mg, 0.0006 mmol, 0.01 mol %) in PhMe (60.0 mL) was added dropwise KOH (50 wt % aq., 25 mol %, 150 μL). The mixture was stirred vigorously for 24 h. An aliquot (50λ) was taken out to determine the conversion (>95% conv.), chemo-, regio-, diastereo- and enantio-selectivity. The reaction was quenched by adding citric acid (15% aq., 30.0 mL) and THF (30.0 mL) and moved to room temperature to be stirred for 1h. The aqueous layer was then separated and extracted with CH₂Cl₂ (10.0 mL×3). The organic layers were combined and cooled to 0° C. MeOH (30.0 mL) was added followed by portion wise addition of NaBH₄ (1.2 g, 30.0 mmol). The mixture was stirred overnight. NaOH (1.0 wt % aq., 30 mL) was added to quench the reaction. The aqueous layer was separated and extracted with CH₂Cl₂ (20 mL×3). The organic extracts were combined, washed with H₂O (30 mL) and extracted with 6N HCl (20 mL×4). The HCl extracts were collected and evaporated under vacuum. The brown residue was recrystallized with iPrOH/Heptane (twice) to afford the pyrrolidine. HCl (−)-24Aa. HCl as a white solid (0.747 g, 62% yield).

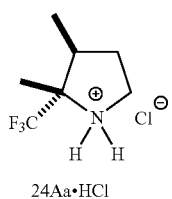

24Aa·HCl $[\alpha]_D^{20}$=−5.9 (c=0.64, CH₃OH). ¹H NMR (400 MHz, CD₃OD) δ 3.52 (ddd, J=11.8, 9.0, 3.1 Hz, 1H), 3.41-3.32 (m, 1H), 2.75-2.61 (m, 1H), 2.44-2.32 (m, 1H), 1.97-1.83 (m, 1H), 1.54 (s, 3H), 1.17 (d, J=6.8 Hz, 3H). ¹³C NMR (100 MHz, CD3OD) δ 126.6 (q, $J_{C-F}$=282.2 Hz), 70.4 (q, $J_{C-F}$=29.0 Hz), 45.3, 38.4, 31.9, 13.7, 13.6 (q, $J_{C-F}$=1.9 Hz). ¹⁹F NMR (376 MHz, CD3OD) δ=−78.7 (s). IR ν 3122, 3012, 2803, 2626, 2557, 2453, 1660, 1558, 1395, 1310, 1193, 1145, 1100, 976, 775 cm⁻¹. HRMS (ESI/[M−Cl]⁺) Calcd. for C₇H₁₃NF₃ m/z 168.1000. found m/z 168.0999.

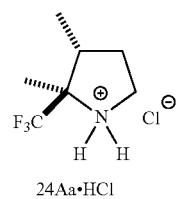

24Aa·HCl

Following the same procedure, pyrrolidine. HCl (+)-24Aa. HCl was obtained as a white solid (0.5 mmol scale reaction, 57.0 mg, 57% yield, recrystallized once from iPrOH/Heptane). $[\alpha]_D^{20}$=+5.7 (c=0.50, CH₃OH).

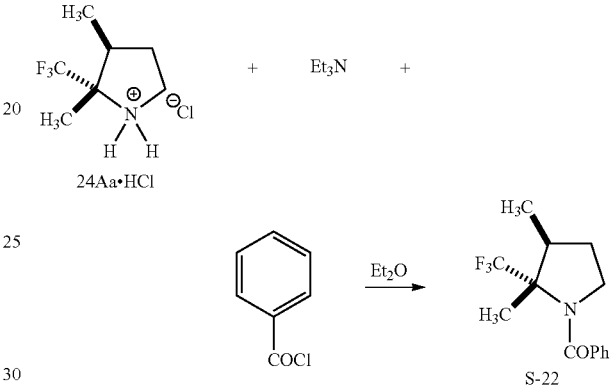

Under N₂, to the suspension of (−)-24Aa. HCl (20.4 mg, 0.1 mmol) in Et₂O (2.0 mL) was added Et₃N (23.3 mg, 0.23 mmol). The mixture was stirred at room temperature for 5 mins. Then PhCOCl (32.3 mg, 0.23 mmol) was added dropwise with a water bath. The white suspension was allowed to stir overnight. NaHCO₃ (2.0 mL) was added to quench the reaction and the aqueous layer was extracted with CH₂Cl₂ (3.0 mL×3). The organic extracts were combined, dried over Na₂SO₄ and concentrated under vacuum. The residue was applied to column (Hex/EA=50/1 to Hex/EA=10/1) to afford compound (−)-S22 as a white solid (25.1 mg, 93% yield). The compound was determined to be 96% ee by HPLC analysis. HPLC conditions: Daicel Chiralpak AS-H, Hex/IPA=92/8, 1.0 mL/min, 220 nm, 50 bar, 25 C. t(major)=8.36 min, t(minor)=7.05 min. $[\alpha]_D^{20}$=−74.5 (c=1.01, CHCl₃). ¹H NMR (400 MHz, CDCl₃) δ 7.41-7.32 (m, 5H), 3.46-3.32 (m, 2H), 2.64-2.51 (m, 1H), 1.94-1.84 (m, 1H), 1.73 (s, 3H), 1.46 (qd, J=11.5, 7.7 Hz, 1H), 1.12 (d, J=6.8 Hz, 3H). ¹³C NMR (100 MHz, CDCl₃) δ 170.6, 138.5, 129.8, 128.5, 127.5 (q, $J_{C-F}$=286.4 Hz), 126.5, 68.3 (q, $J_{C-F}$=28.2 Hz), 51.6, 39.9, 31.6, 15.0, 14.1. ¹⁹F NMR (376 MHz, CDCl₃) δ=−74.9 (s). IR (CHCl₃) ν 2981, 2884, 1655, 1474, 1446, 1377, 1295, 1188, 1148, 1117, 945, 722, 659 cm⁻¹. HRMS (ESI/[M+H]⁺) Calcd. for C₁₄H₁₇NOF₃ m/z 272.1262. found m/z 272.1262.

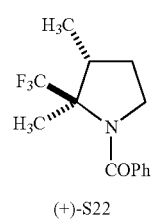

(+)-S22

Following the same procedure, the opposite enantiomer (+)-S22 was obtained as a white solid (23.6 mg, 87% yield). The compound was determined to be 91% ee by HPLC analysis. $[\alpha]_D^{20}=+69.6$ (c=1.09, CHCl$_3$).

Example 7: Assignment of Relative and Absolute Configuration of 9Aa

A single crystal of 24Aa·HCl was obtained via recrystallization in CH$_3$CN. The relative and absolute configuration of the corresponding amine 9Aa could thus be deduced by analysis of the crystallographic structure of 24Aa·HCl. The two methyl groups are in syn position. And both chiral centers are S configuration. All operations were performed on a Bruker-Nonius Kappa Apex2 diffractometer, using graphite-monochromated MoKα radiation. All diffractometer manipulations, including data collection, integration, scaling, and absorption corrections were carried out using the Bruker Apex2 software. Preliminary cell constants were obtained from three sets of 12 frames. Data collection was carried out at 120K, using a frame time of 10 sec and a detector distance of 60 mm. The optimized strategy used for data collection consisted of two phi and three omega scan sets, with 0.5° steps in phi or omega; completeness was 99.0%. A total of 1041 frames were collected. Final cell constants were obtained from the xyz centroids of 3064 reflections after integration.

From the systematic absences, the observed metric constants and intensity statistics, space group P2$_1$2$_1$2$_1$ was chosen initially; subsequent solution and refinement confirmed the correctness of this choice. The structure was solved using SuperFlip, and refined (full-matrix–least squares) using the Oxford University Crystals for Windows program. The asymmetric unit contains one molecule of the complex (Z=4; Z'=1). All non-hydrogen atoms were refined using anisotropic displacement parameters. After location of H atoms on electron-density difference maps, the H atoms were initially refined with soft restraints on the bond lengths and angles to regularize their geometry (C—H in the range 0.93-0.98 Å and U$_{iso}$ (H) in the range 1.2-1.5 times U$_{eq}$ of the parent atom), after which the positions were refined with riding constraints. The absolute structure was established by using Flack parameter refinement (x=0.06(6)). The final least-squares refinement converged to R$_1$=0.0285 (I>2σ(I), 2361 data) and wR2=0.0643 (F$^2$, 2761 data, 117 parameters).

Example 8: Asymmetric Synthesis of Unprotected Aminoalcohol 23Aa

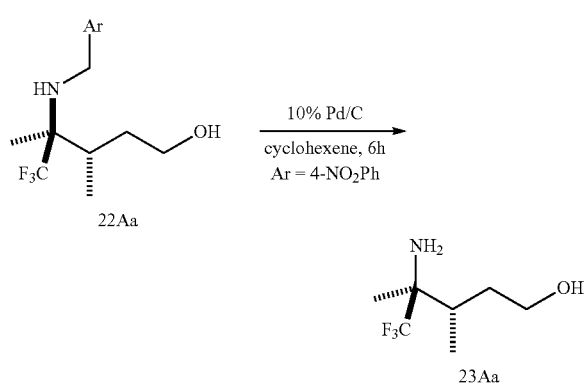

Under N$_2$, to the suspension of 22Aa (29.5 mg, 0.092 mmol) and 10% Pd/C (9.8 mg, 0.0092 mmol) in cyclohexene (0.74 mL) was added MeOH (0.50 mL). The black suspension was then stirred at reflux. After 6 h, the reaction was completed as determined by $^{19}$F NMR. Next the suspension was filtered through a pad of Celite and washed with MeOH (0.50 mL×2). The filtrates were combined and concentrated under vacuum. The residue was applied to silica column chromatography (CH$_2$Cl$_2$ to CH$_2$Cl$_2$/MeOH=5/1) to afford 23Aa as a light yellow liquid (16.6 mg, 97% yield). $[\alpha]_D^{20}=-20.1$ (c=0.77, CHCl$_3$). $^1$H NMR (400 MHz, CDCl$_3$) δ 3.76-3.68 (m, 1H), 3.61-3.51 (m, 1H), 2.32 (s, 3H), 1.96 (ddd, J=14.6, 10.0, 5.3 Hz, 1H), 1.85-1.74 (m, 1H), 1.43-1.31 (m, 1H), 1.15 (s, 3H), 0.98 (dd, J=6.9, 1.6 Hz, 3H). $^{13}$C NMR (100 MHz, CDCl$_3$) δ 128.5 (q, J$_{C-F}$=286.6 Hz), 61.5, 58.7 (q, J$_{C-F}$=24.8 Hz), 37.0, 35.8, 16.5 (q, J$_{C-F}$=2.6 Hz), 16.4 (q, J$_{C-F}$=1.8 Hz). $^{19}$F NMR (376 MHz, CDCl$_3$) δ=−77.8 (s). IR (CHCl$_3$) ν 2981, 2884, 1655, 1474, 1446, 1377, 1295, 1188, 1148, 1117, 945, 722, 659 cm$^{-1}$. HRMS (ESI/[M+H]$^+$) Calcd. for C$_7$H$_{15}$NOF$_3$ m/z 186.1106. found m/z 186.1107.

Example 9: Assignment of Absolute Configuration of 9Ge is Shown in FIG. 5B

The solution of trifluoromethyl imine 1G (203.1 mg, 0.66 mmol) and catalyst C-21b (1.4 mg, 0.00132 mmol, 0.2 mol %) in toluene (5.7 mL) was cooled to −20° C. KOH (50 wt % aq., 0.066 mmol, 6.0 μL) was added right after a solution of acrolein (74.0 mg, 1.32 mmol) in PhMe (1.0 mL) started being added with a syringe pump (0.33 mL/h). After the completion of the reaction, THF (3.3 mL) and Citric acid (15 wt % aq., 3.3 mL) were added sequentially. The mixture was moved to room temperature and stirred overnight. The process of the hydrolysis was monitored by $^1$H NMR. Then the aqueous layer was separated and extracted with CH$_2$Cl$_2$ (5.0 mL×3). The organic extracts were combined and concentrated under vacuum. MeOH (3.0 mL) was added. At 0° C., NaBH$_4$ (3.3 mmol, 125 mg) was added portion wise. The mixture was warmed room temperature and stirred for 2h. NaOH (1.0 wt % aq., 3 mL) was added to quench the reaction. The organic layer was separated and the aqueous layer was extracted with CH$_2$Cl$_2$ (5 mL×3). The organic extracts were combined, washed over brine, dried over Na$_2$SO$_4$ and concentrated under vacuum. The residue was applied to column chromatography (Hexanes/CH$_2$Cl$_2$=10/1 to 2/1) to afford the pyrrolidine 24Ge as a light yellow liquid (105.4 mg, 74% yield).

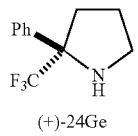

(+)-24Ge (+)-24Ge was prepared by C-21b catalyzed reaction. The compound was determined to be 95% ee by HPLC analysis (Daicel Chiralpak OJ-H, Hex/IPA=95/5, 1.0 mL/min, 210 nm, 45 bar, 25° C. t(major)=20.29 min, t(minor)=14.90 min). $[\alpha]_D^{20}=+30.3$ (c=1.08, CHCl$_3$). $^1$H NMR (400 MHz, CDCl$_3$) δ 7.49 (d, J=7.7 Hz, 2H), 7.38-7.27 (m, 3H), 3.24-3.04 (m, 2H), 2.60-2.48 (m, 1H), 2.35-2.16 (m, 2H), 2.05-1.91 (m, 1H), 1.88-1.72 (m, 1H). $^{13}$C NMR (100 MHz, CDCl$_3$) δ 140.1, 128.3, 128.2, 127.5 (q, J$_{C-F}$=284.7 Hz), 127.4, 70.1 (q, J$_{C-F}$=26.3 Hz), 47.0, 34.5, 25.4. $^{19}$F NMR (376 MHz, CDCl$_3$) δ=−76.7 (s). IR (CHCl$_3$) ν 2987, 2893, 1494, 1448, 1282, 1154, 1092, 986, 762, 703 cm$^{-1}$. HRMS (ESI/[M+H]$^+$) Calcd. for C$_{11}$H$_{13}$NF$_3$ m/z 216.1000. found m/z 216.0990.

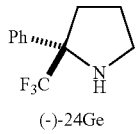

(−)-24Ge (−)-24Ge was prepared by CD-21b catalyzed reaction (0.2 mmol scale reaction, 28.9 mg, 68% yield). The compound was determined to be 86% ee by HPLC analysis. [α]$_D^{20}$=−27.9 (c=1.00, CHCl$_3$).

A single crystal of 24Ge.HCl was obtained through recrystallizing acidified (+)-24Ge in iPrOH/Heptane and subjected to X-ray crystallographic analysis. The absolute configuration of the corresponding amine 9Ge was deduced. The chiral center is in the R configuration.

All operations were performed on a Bruker-Nonius Kappa Apex2 diffractometer, using graphite-monochromated MoKα radiation. All diffractometer manipulations, including data collection, integration, scaling, and absorption corrections were carried out using the Bruker Apex2 software. Preliminary cell constants were obtained from three sets of 12 frames. Data collection was carried out at 120K, using a frame time of 20 sec and a detector distance of 60 mm. The optimized strategy used for data collection consisted of six phi scan sets, with 0.5° steps in phi; completeness was 100.0%. A total of 3626 frames were collected. Final cell constants were obtained from the xyz centroids of 6976 reflections after integration.

From the systematic absences, the observed metric constants and intensity statistics, space group P2$_1$ was chosen initially; subsequent solution and refinement confirmed the correctness of this choice. The structure was solved using SIR-92, and refined (full-matrix–least squares) using the Oxford University Crystals for Windows program. The asymmetric unit contains one molecule of the compound (Z=2; Z'=1). All non-hydrogen atoms were refined using anisotropic displacement parameters. After location of H atoms on electron-density difference maps, the H atoms were initially refined with soft restraints on the bond lengths and angles to regularize their geometry (C—H in the range 0.93-0.98 Å and U$_{iso}$ (H) in the range 1.2-1.5 times U$_{eq}$ of the parent atom), after which the positions were refined with riding constraints. The absolute structure was established by using Flack parameter refinement (x=−0.03(4)). The final least-squares refinement converged to R$_1$=0.0229 (I>26(I), 2694 data) and wR$_2$=0.0584 (F2, 2791 data, 153 parameters).

Example 10: Assignment of Absolute Configuration of 31Ae

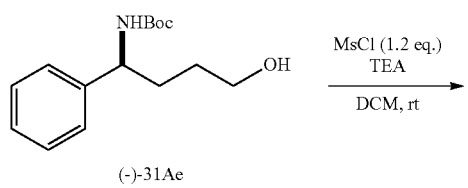

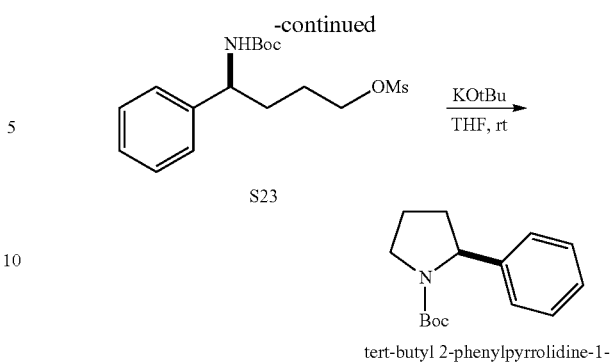

tert-butyl 2-phenylpyrrolidine-1-carboxylate, S24

To a solution of (−)-31Ae (0.109 mmol, 29.0 mg) and Et$_3$N (0.131 mmol, 18 μL) in anhydrous CH$_2$Cl$_2$ (1.0 mL) was added dropwise methanesulfonyl chloride (0.131 mmol, 10 μL) at room temperature. After being stirred at room temperature for additional 30 min, the reaction mixture was quenched with H$_2$O (2.0 mL) and extracted with CH$_2$Cl$_2$ (3.0 mL×3). The combined organic layers were dried over anhydrous Na$_2$SO$_4$ and concentrated. The crude product S23 was used for the next step directly.

S23 was dissolved in anhydrous THF (1.0 mL) and potassium tert-butoxide (0.33 mL 1.0 M solution in THF, 0.327 mmol) was dropwise added at rt. After stirring at rt for additional 12 h, the reaction mixture was quenched with H$_2$O (2.0 mL) and extracted with CH$_2$Cl$_2$ (3.0 mL×3). The combined organic layers were dried over anhydrous Na$_2$SO$_4$ and concentrated. The residue was purified on silica column chromatography to give N-Boc-2-phenylpyrrolidine S24 as a white solid (24.0 mg, 89% yield for 2 steps).

The absolute configuration of S24 was determined to be S isomer by comparing the specific optical rotation with Campos, et al., 2006, J. Am. Chem. Soc. 128:3538-3539. [α]$_D^{25}$=−72.6 (c=1.8, acetone); [lit. [α]$_D^{25}$=+85.3 (c=1.9, acetone) for the R isomer of S24].

Example 11: Synthesis of Chiral Aliphatic Amine 35Ae

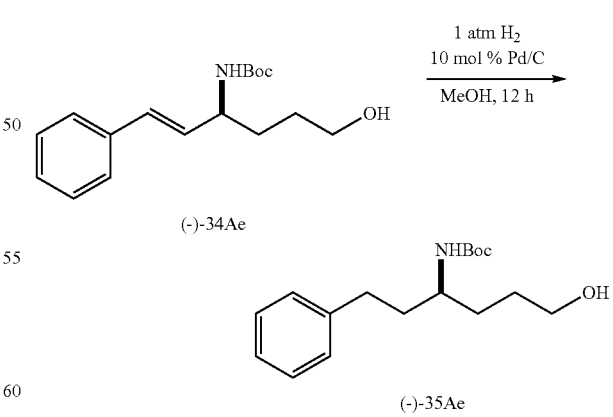

To a solution of N-Boc amino-alcohol (−)-34Ae (16.0 mg, 0.055 mmol) in MeOH (2 mL) was added 10% Pd/C (5.8 mg, 0.0055 mmol). The black suspension was stirred under 1 atm H$_2$ at room temperature for 12 h. Then the reaction mixture was filtered through a short pad of Celite and concentrated. The crude product was purified by flash chromatography (Hexanes/ethyl acetate=5:1) to afford (−)-35Ae as a yellow liquid (15.0 mg, 94% yield) with 92% ee as determined by HPLC analysis [Chiralpak, AS-H, Hexanes/IPA=95/5, 1.0 mL/min, λ 220 nm, t(minor)=12.56 min, t(major)=14.15 min]. [α]$_D^{20}$=−3.8 (c=0.51, CHCl$_3$). $^1$H NMR (400 MHz, CDCl3) δ 7.35-7.23 (m, 2H), 7.18 (t, J=5.8 Hz, 3H), 4.38 (d, J=9.1 Hz, 1H), 3.66 (t, J=5.1 Hz, 2H), 2.87-2.41 (m, 2H), 2.00-1.51 (m, 6H), 1.45 (s, 9H). $^{13}$C NMR (100 MHz, CDCl$_3$) δ 155.9, 141.9, 128.4, 128.3, 125.8, 79.2, 62.6, 50.3, 37.7, 32.3, 32.4, 28.8, 28.4. IR (CHCl$_3$) ν 3340, 3005, 2933, 2863, 1690, 1519, 1452, 1367, 1248, 1172, 1061, 754. HRMS (ESI/[M+Na]$^+$) Calcd. for C$_{17}$H$_{27}$NNaO$_3$ m/z 316.1889. found m/z 316.1888.

(+)-35Ae was obtained starting from (+)-34Ae following the same procedure as above (0.045 mmol scale reaction, 12.1 mg, 92% yield). The ee was determined to be 88% by HPLC analysis. [α]$_D^{20}$+3.3 (c=0.60, CHCl$_3$).

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound, or a salt, N-oxide, tautomer, enantiomer or diastereoisomer thereof, of formula (I):

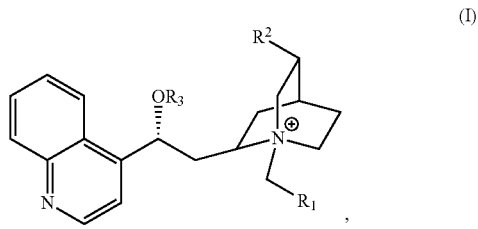

(I)

wherein:
R$^1$ is

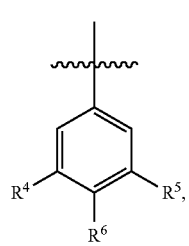

R$^4$ and R$^5$ are independently selected from the group consisting of alkyl, alkoxy and aryl
R$^6$ is selected from the group consisting of H, alkyl, alkoxy, aryloxy, —S(alkyl), —S(aryl), —OSiR$_3$ and —NR$_2$; and each occurrence of R is independently selected from alkyl and aryl;
R$^2$ is selected from the group consisting of optionally substituted alkyl, optionally substituted C$_2$-C$_6$ alkenyl and optionally substituted C$_2$-C$_6$ alkynyl, where each optional substituent is independently selected from the group consisting of alkyl, alkoxy, aryloxy, —S— alkyl, —S(aryl), —OSiR$_3$ and —NR$_2$; and R$^3$ is selected from the group consisting of optionally substituted aryl and optionally substituted heteroaryl, where each optional substituent is independently selected from the group consisting of alkyl, alkoxy, chloro, phenyl, and acyl.

2. The compound of claim 1, wherein R$^4$ is aryl.

3. The compound of claim 1, wherein at least one selected from the group consisting of R$^4$ and R$^5$ is aryl, which is independently optionally substituted with at least one substituent selected from alkyl, alkoxy, —S(alkyl), and —OSiR$_3$.

4. The compound of claim 3, wherein R$^4$ and R$^5$ are both independently aryl, each of which is independently optionally substituted with at least one substituent selected from alkyl, alkoxy, —S(alkyl), and —OSiR$_3$.

5. The compound of claim 1, wherein R$^6$ is selected from the group consisting of alkyl, alkoxy, aryloxy, —S(alkyl), —S(aryl), —OSiR$_3$ and —NR$_2$.

6. The compound of claim 5, wherein R$^6$ is selected from the group consisting of alkoxy and —OSiR$_3$.

7. The compound of claim 5, wherein each occurrence of R is independently alkyl.

8. The compound of claim 1, wherein R$^1$ is selected from the group consisting of 3,5-dimethoxyphenyl, 3,5-diphenyl-phenyl, 3,5-(4-methoxyphenyl)-phenyl, 3,5-diphenyl-4-methoxy-phenyl and 3,5-diphenyl-4-(t-butyldimethylsiloxy)-phenyl.

9. The compound of claim 1, wherein R$^2$ is selected from the group consisting of unsubstituted alkyl, unsubstituted alkenyl and unsubstituted alkynyl.

10. The compound of claim 9, wherein R$^2$ is selected from the group consisting of unsubstituted alkyl and unsubstituted alkenyl.

11. The compound of claim 10, wherein R$^2$ is selected from the group consisting of vinyl and ethyl.

12. The compound of claim 1, wherein R$^3$ is selected from the group consisting of optionally substituted phenyl, optionally substituted pyrimidinyl, and optionally substituted phenanthryl.

13. The compound of claim 12, wherein R$^3$ is selected from the group consisting of 4-chloro-2,5-diphenyl-pyridin-6-yl and phenanthr-9-yl.

14. The compound of claim 1, which is selected from the group consisting of:

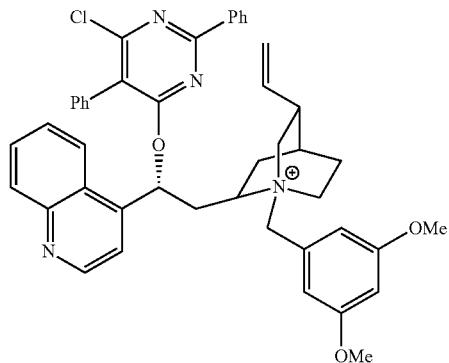 [SMILES: C=CC1C[N+]2(Cc3cc(OC)cc(OC)c3)CCC1CC2C[C@@H](Oc1nc(-c2ccccc2)nc(Cl)c1-c1ccccc1)c1ccnc2ccccc12]

(1S,2R,4S,5R)-2-((S)-((6-chloro-2,5-diphenylpyrimidin-4-yl)oxy)(quinolin-4-yl)methyl)-1-(3,5-dimethoxybenzyl)-5-vinylquinuclidin-1-ium (C-16);

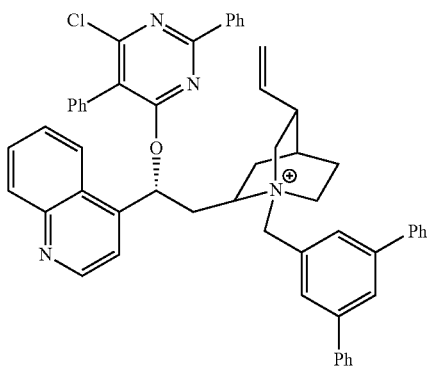 [SMILES: C=CC1C[N+]2(Cc3cc(-c4ccccc4)cc(-c4ccccc4)c3)CCC1CC2C[C@@H](Oc1nc(-c2ccccc2)nc(Cl)c1-c1ccccc1)c1ccnc2ccccc12]

(1S,2R,4S,5R)-1-([1,1':3',1"-terphenyl]-5'-ylmethyl)-2-((S)-((6-chloro-2,5-diphenylpyrimidin-4-yl)oxy)(quinolin-4-yl)methyl)-5-vinylquinuclidin-1-ium (C-18);

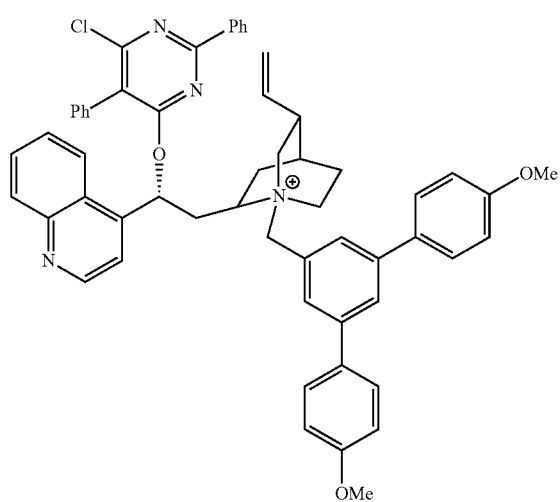 [SMILES: C=CC1C[N+]2(Cc3cc(-c4ccc(OC)cc4)cc(-c4ccc(OC)cc4)c3)CCC1CC2C[C@@H](Oc1nc(-c2ccccc2)nc(Cl)c1-c1ccccc1)c1ccnc2ccccc12]

(1S,2R,4S,5R)-2-((S)-((6-chloro-2,5-diphenylpyrimidin-4-yl)oxy)(quinolin-4-yl)methyl)-1-((4,4"-dimethoxy-[1,1':3',1"-terphenyl]-5'-yl)methyl)-5-vinylquinuclidin-1-ium (C-20);

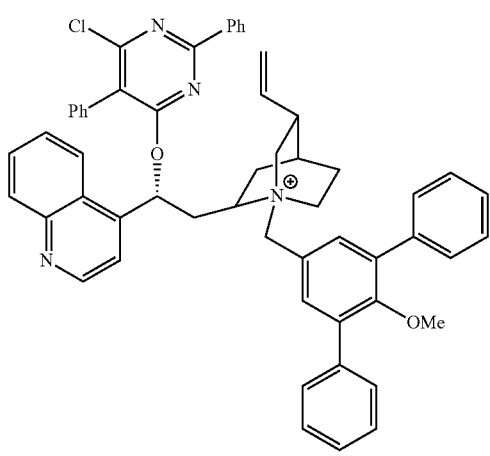 [SMILES: C=CC1C[N+]2(Cc3cc(-c4ccccc4)c(OC)c(-c4ccccc4)c3)CCC1CC2C[C@@H](Oc1nc(-c2ccccc2)nc(Cl)c1-c1ccccc1)c1ccnc2ccccc12]

(1S,2R,4S,5R)-2-((S)-((6-chloro-2,5-diphenylpyrimidin-4-yl)oxy)(quinolin-4-yl)methyl)-1-((2'-methoxy-[1,1':3',1"-terphenyl]-5'-yl)methyl)-5-vinylquinuclidin-1-ium (C-21a);

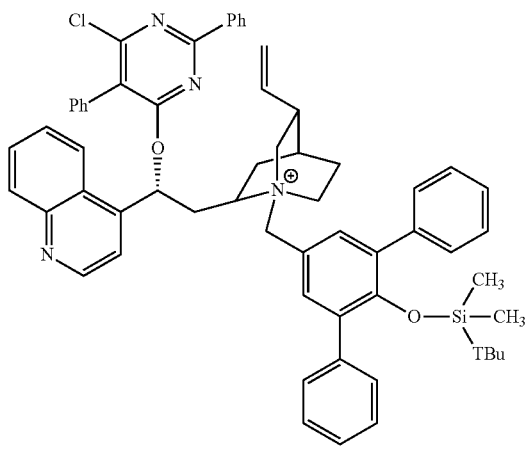

(1S,2R,4S,5R)-1-((2'-((tert-butyldimethylsilyl)oxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21b); and

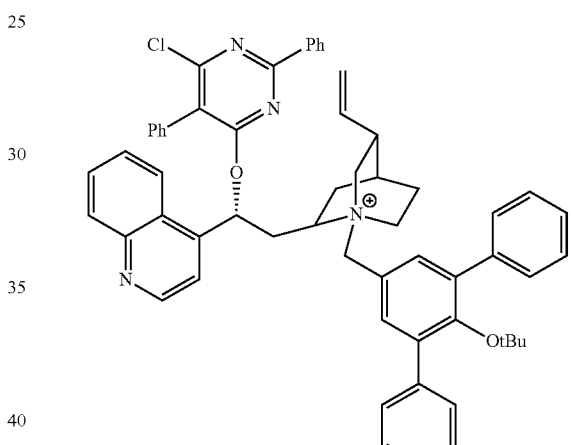

(1S,2R,4S,5R)-1-((2'-(tert-butoxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21c).

15. A method of promoting an asymmetric coupling reaction between an imine and a Michael acceptor substrate, the method comprising contacting the imine, the Michael acceptor substrate and at least one compound of any one of claims 1-14, wherein the imine comprises formula (II):

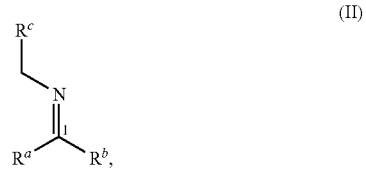

(II)

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S— alkyl, —S(aryl), —OSiR$_3$ and —NR$_2$; or (b) R$^a$ is H, and R$^b$ is selected from the group consisting of optionally substituted aryl, optionally substituted heteroaryl, optionally substituted vinyl, and optionally substituted alkynyl; where each optional substituent is independently selected from the group consisting of alkyl, alkoxy, aryloxy, —S-alkyl, —S(aryl), —OSiR$_3$ and —NR$_2$; and R$^c$ is selected from the group consisting of optionally substituted alkyl, optionally substituted alkenyl, optionally substituted aryl, and optionally substituted heteroaryl, where each optional substituent is independently selected from the group consisting of alkyl, alkoxy, aryloxy, —S-alkyl, —S(aryl), —OSiR$_3$ and —NR$_2$.

16. The method of claim 15, wherein the Michael acceptor substrate comprises at least one selected from the group consisting of an optionally substituted α,β-unsaturated aldehyde, an optionally substituted α,β-unsaturated ketone, an optionally substituted enone, an optionally substituted α,β-unsaturated carboxylic acid, an optionally substituted α,β-unsaturated carboxylic ester, an optionally substituted α,β-unsaturated amide, an optionally substituted α,β-unsaturated sulfone, and an optionally substituted α,β-unsaturated sulfoxide.

17. The method of claim 16, wherein a carbon-carbon bond is between carbon '1' in (II) and the β-carbon in the Michael acceptor substrate.

18. The method of claim 15, wherein the at least one compound is selected from the group consisting of:
(1S,2R,4S, 5R)-2-((S)-((6-chloro-2, 5-diphenylpyrimidin-4-yl)oxy)(quinolin-4-yl)methyl)-1-(3,5-dimethoxybenzyl)-5-vinylquinuclidin-1-ium (C-16);
(1S,2R,4S,5R)-1-([1,1':3',1"-terphenyl]-5'-ylmethyl)-2-((S)-((6-chloro-2,5-diphenylpyrimidin-4-yl)oxy)(quinolin-4-yl)methyl)-5-vinylquinuclidin-1-ium (C-18);
(1S,2R,4S,5R)-2-((S)-((6-chloro-2,5-diphenylpyrimidin-4-yl)oxy)(quinolin-4-yl)methyl)-1-((4,4"-dimethoxy-[1,1':3',1"-terphenyl]-5'-yl)methyl)-5-vinylquinuclidin-1-ium (C-20);
(1S,2R,4S,5R)-2-((S)-((6-chloro-2,5-diphenylpyrimidin-4-yl)oxy)(quinolin-4-yl)methyl)-1-((2'-methoxy-[1,1':3',1"-terphenyl]-5'-yl)methyl)-5-vinylquinuclidin-1-ium (C-21a);
(1S,2R,4S,5R)-1-((2'-((tert-butyl dimethyl silyl)oxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21b); and
(1S,2R,4S,5R)-1-((2'-(tert-butoxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21c).

19. A method of isomerizing an imine of formula (II):

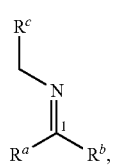

(II)

wherein:
(a) R$^a$ is trifluoromethyl, and R$^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S— alkyl, —S(aryl), —OSiR$_3$ and —NR$_2$, or (b) R$^a$ is H, and R$^b$ is selected from the group consisting of optionally substituted aryl, optionally substituted heteroaryl, and optionally substituted vinyl, where each optional substituent is independently selected from the group consisting of alkyl, alkoxy, aryloxy, —S— alkyl, —S(aryl), —OSiR$_3$ and —NR$_2$, and R$^c$ is selected from the group consisting of optionally substituted alkyl, optionally substituted alkenyl, optionally substituted aryl, and optionally substituted heteroaryl, where each optional substituent is independently selected from the group consisting of alkyl, alkoxy, aryloxy, —S-alkyl, —S(aryl), —OSiR$_3$ and —NR$_2$; the method comprising contacting the imine of formula (II) with at least one compound of any one of claims 1-16, thus forming a compound of formula (III):

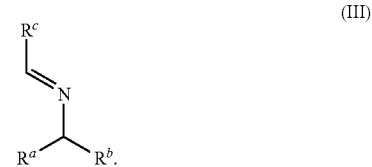

(III)

20. The method of claim 19, wherein the at least one compound is selected from the group consisting of:
(1S,2R,4S,5R)-2-((S)-((6-chloro-2,5-diphenylpyrimidin-4-yl)oxy)(quinolin-4-yl)methyl)-1-(3,5-dimethoxybenzyl)-5-vinylquinuclidin-1-ium (C-16);
(1S,2R,4S,5R)-1-([1,1':3',1"-terphenyl]-5'-ylmethyl)-2-((S)-((6-chloro-2,5-diphenylpyrimidin-4-yl)oxy)(quinolin-4-yl)methyl)-5-vinylquinuclidin-1-ium (C-18);
(1S,2R,4S,5R)-2-((S)-((6-chloro-2,5-diphenylpyrimidin-4-yl)oxy)(quinolin-4-yl)methyl)-1-((4,4"-dimethoxy-[1,1':3',1"-terphenyl]-5'-yl)methyl)-5-vinylquinuclidin-1-ium (C-20);
(1S,2R,4S,5R)-2-((S)-((6-chloro-2,5-diphenylpyrimidin-4-yl)oxy)(quinolin-4-yl)methyl)-1-((2'-methoxy-[1,1':3',1"-terphenyl]-5'-yl)methyl)-5-vinylquinuclidin-1-ium (C-21a);
(1S,2R,4S,5R)-1-((2'-((tert-butyldimethylsilyl)oxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21b); and
(1S,2R,4S,5R)-1-((2'-(tert-butoxy)-[1,1':3',1"-terphenyl]-5'-yl)methyl)-2-((S)-((6-chloro-2,5-diphenylpyrimidin-4-yl)oxy)(quinolin-4-yl)methyl)-5-vinylquinuclidin-1-ium (C-21c).

21. A kit comprising at least one compound of claim 1, and instructions for using the at least one compound to catalyze an asymmetric coupling reaction between an imine of formula (II) and a Michael acceptor substrate, and/or to catalyze the enantioselective or diastereoselective isomerization of an imine of formula (II):

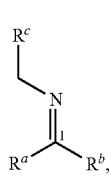

(II)

wherein:
(a) $R^a$ is trifluoromethyl, and $R^b$ is selected from the group consisting of optionally substituted alkyl, optionally substituted aryl, optionally substituted heteroaryl, optionally substituted alkenyl, and optionally substituted alkynyl, where each optional substituent is independently selected from the group consisting of alkyl, alkoxy, aryloxy, —S— alkyl, —S(aryl), —OSiR$_3$ and —NR$_2$; or
(b) $R^a$ is H, and $R^b$ is selected from the group consisting of optionally substituted aryl, optionally substituted heteroaryl, optionally substituted vinyl, and optionally substituted alkynyl, where each optional substituent is independently selected from the group consisting of alkyl, alkoxy, aryloxy, —S-alkyl, —S(aryl), —OSiR$_3$ and —NR$_2$; and $R^c$ is selected from the group consisting of optionally substituted alkyl, optionally substituted alkenyl, optionally substituted aryl and optionally substituted heteroaryl, where each optional substituent is independently selected from the group consisting of alkyl, alkoxy, aryloxy, —S-alkyl, —S(aryl), —OSiR$_3$ and —NR$_2$.

\* \* \* \* \*